(12) United States Patent
Machin et al.

(10) Patent No.: US 12,202,816 B2
(45) Date of Patent: Jan. 21, 2025

(54) COMPOUNDS AS NADPH OXIDASE INHIBITORS

(71) Applicant: CALLIDITAS THERAPEUTICS SUISSE SA, Plan-les-Ouates (CH)

(72) Inventors: Peter Machin, London (GB); Mark Chambers, Essex (GB); Alastair Hodges, Cambridgeshire (GB); Andrew Sharpe, Essex (GB); Grant Wishart, Essex (GB); Benjamin Perry, Collonges sous Saleve (FR); Sylvain Celanire, Reignier-Esery (FR); Freddy Heitz, Bernex (CH)

(73) Assignee: CALLIDITAS THERAPEUTICS SUISSE SA, Plan-les-Ouates (CH)

( * ) Notice: Subject to any disclaimer, the term of this patent is extended or adjusted under 35 U.S.C. 154(b) by 877 days.

(21) Appl. No.: 17/278,489

(22) PCT Filed: Sep. 27, 2019

(86) PCT No.: PCT/EP2019/076273
§ 371 (c)(1),
(2) Date: Mar. 22, 2021

(87) PCT Pub. No.: WO2020/065048
PCT Pub. Date: Apr. 2, 2020

(65) Prior Publication Data
US 2022/0033379 A1    Feb. 3, 2022

(30) Foreign Application Priority Data
Sep. 28, 2018 (EP) .................................... 18197787

(51) Int. Cl.
C07D 401/14    (2006.01)
A61K 45/06    (2006.01)
(Continued)

(52) U.S. Cl.
CPC ............. *C07D 401/14* (2013.01); *A61P 1/16* (2018.01); *C07D 405/14* (2013.01);
(Continued)

(58) Field of Classification Search
None
See application file for complete search history.

(56) References Cited

U.S. PATENT DOCUMENTS

2007/0105866 A1    5/2007    Hutchinson et al.

FOREIGN PATENT DOCUMENTS

WO    WO 2001/14371    3/2001
WO    WO 2008/116926    10/2008
(Continued)

OTHER PUBLICATIONS

Wynn TA, Ramalingam TR. Mechanisms of fibrosis: therapeutic translation for fibrotic disease. Nat Med. Jul. 6, 2012;18(7):1028-40 (Year: 2012).*

(Continued)

*Primary Examiner* — Jeffrey S Lundgren
*Assistant Examiner* — Anthony Joseph Seitz
(74) *Attorney, Agent, or Firm* — Ballard Spahr LLP

(57) ABSTRACT

Disclosed herein are new compounds, pharmaceutical composition thereof and to their use for the treatment and/or prophylaxis of disorders or conditions related to Nicotinamide adenine dinucleotide phosphate oxidase (NADPH Oxidase).

21 Claims, 3 Drawing Sheets

(51) Int. Cl.
  *A61P 1/16* (2006.01)
  *C07D 405/14* (2006.01)
  *C07D 417/14* (2006.01)
  *C07D 491/107* (2006.01)
  *C07D 491/20* (2006.01)
  *C07D 498/04* (2006.01)

(52) U.S. Cl.
  CPC ....... *C07D 417/14* (2013.01); *C07D 491/107* (2013.01); *C07D 491/20* (2013.01); *C07D 498/04* (2013.01); *A61K 45/06* (2013.01)

(56) References Cited

FOREIGN PATENT DOCUMENTS

| WO | WO-2008116926 A1 * | 10/2008 | ........... A61K 31/404 |
|---|---|---|---|
| WO | WO 2010/045188 | 4/2010 | |
| WO | US-20110071150 A1 * | 3/2011 | ........... C07D 417/04 |
| WO | WO 2011/036130 | 3/2011 | |
| WO | WO 2011/151619 | 12/2011 | |
| WO | WO 2012/173952 | 12/2012 | |
| WO | WO 2013/010904 | 1/2013 | |
| WO | WO 2013/064468 | 5/2013 | |
| WO | WO 2014/106649 | 7/2014 | |
| WO | WO 2014/153227 | 9/2014 | |
| WO | WO 2015/138273 | 9/2015 | |
| WO | WO 2019/086579 | 5/2019 | |
| WO | WO 2019/126253 | 6/2019 | |

OTHER PUBLICATIONS

Duan et al., J Am Chem Soc., 2016, vol. 138, No. 51, pp. 16686-16695.
He et al., ACS Nano, 2015, vol. 9, p. 991.
Thabut et al., 2002, J. Biol. Chem., 277:22814-22821.
Brigham, 1986, Chest, 89(6): 859-863.
Djordjevic et al., 2005, Arterioscler. Thromb. Vasc. Biol., 25, 519-525.
Liu et al., 2004, Am. J. Physiol. Lung, Cell. Mol. Physiol., 287:L111-118.
Yang et al., 2002, J. Cell. Chem. 84, 645-654.
Ellis et al., 2000, Free Rad. Biol. Med., 28:91-101.
Pillarisetti et al., 2004, Expert Opin. Ther. Targets, 8(5):401-408.
Cai et al., 2003, Trends Pharmacol. Sci., 24:471-478.
Shi et al., 2001, Throm. Vasc. Biol., 2001, 21, 739-745.
Nunomura et al., 2001, J. Neuropathol. Exp. Neurol., 60:759-767.
Girouard, 2006, J. Appl. Physiol. 100:328-335.
Vernet et al., Biol. Reprod., 2001, 65:1102-1113.
Lambeth et al. 2008, Semin. Immunopathol., 2008, 30, 339-363.
Garrido-Urbani, 2011, PLoS ONE, 6(2).
Leto et al., 2006, Antioxid. Redox Signal, 8(9-10):1549-61.
Cheng et al., 2001, Gene, 16; 269(1-2):131-40.
Rynayhossani et al., 2013, J. Bio. Chem., 288(51):36437-50.
Gianni et al., 2010, ACS Chem. Biol., 5(10):981:93.
Wilkinson-Berka et al., 2014, Antioxid. Redox Signal, 20(17):2726-40.
Carnesecchi et al., 2009, American Journal of Respiratory and Critical Care Medicine; 180(10):972-981.
Philip J. Kocienski, in "Protecting Groups", Georg Thieme Verlag Stuttgart, 2005.
Theodora W. Greene and Peter G. M. Wuts in "Protective Groups in Organic Synthesis", Wiley Interscience, 4th Edition 2006.
Palicz et al., 2001, J. Biol. Chem, 76, 3090.
Bartlett et al., 2013, Molecular Cancer 2, 12:10 PCT Spec.
Fukuhara et al., 2016, Cancer Sci, 107(10), 1373-1379.
Perica et al., 2015, Rambam Maimonides Med J 6(1), e0004.
Iwai et al., 2017, Journal of Biomedical Science, 24:26.
Mishra, 2017, Future Oncol. doi: 10.2217/fon-2017-0115.
Soto Chervin et al., 2016, F1000Research 2016, 5(F1000 Faculty Rev):803.
Mertens et al., "Nonsteroidal Cardiotonics. 3. New 4,5-Dihydro-6-(1H-Indol-5-YL)Pyridazin-3(2H)-Ones and related compounds with positive inotropic activities" J of Med Chem, Am Chem Soc, vol. 33, No. 10, Jan. 1, 1990.
International Search Report and Written Opinion were mailed on Jan. 2, 2020 by the International Searching Authority for International Application No. PCT/EP2019/076273, filed on Sep. 27, 2019 and published as WO 2020/065048 on Apr. 2, 2020 (Applicant—Genkyotex Suisse SA) (15 Pages).
Bobko, Mark, et al. "Synthesis of 2, 5-disubstituted-3-cyanoindoles" Tetrahedron Letters, Elsevier, Amsterdam, The Netherlands, vol. 53, No. 2, Nov. 3, 2011, pp. 200-202.

* cited by examiner

COMPOUNDS AS NADPH OXIDASE INHIBITORS

CROSS-REFERENCE TO RELATED APPLICATIONS

This application is a U.S. National Phase Application of International Application No. PCT/EP2019/076273, filed Sep. 27, 2019, which claims priority to European Application No. 18197787.7, filed Sep. 28, 2018, each of which are hereby incorporated by reference in their entirety.

FIELD OF THE INVENTION

The present invention relates to novel derivatives of Formula (I), pharmaceutical composition thereof and to their use for the preparation of a medicament for the treatment and/or prophylaxis of Nicotinamide adenine dinucleotide phosphate oxidase (NADPH Oxidase) related disorders such as fibrotic disorders, cardiovascular diseases, neurodegenerative diseases, inflammatory disorders and cancers. Specifically, the present invention is related to novel derivatives useful for the preparation of a pharmaceutical formulation for the modulation, notably the inhibition of the activity or function of the Nicotinamide adenine dinucleotide phosphate oxidase (NADPH Oxidase).

BACKGROUND OF THE INVENTION

NADPH oxidases (NOX) are proteins that transfer electrons across biological membranes. In general, the electron acceptor is oxygen and the product of the electron transfer reaction is superoxide. The biological function of NOX enzymes is therefore the generation of reactive oxygen species (ROS) from oxygen. Reactive oxygen species (ROS) are oxygen-derived small molecules, including oxygen radicals (super-oxide anion [$^•O_2^-$], hydroxyl [HO$^•$], peroxyl [ROO$^•$], alkoxyl [RO$^•$] and hydroperoxyl [HOO$^•$]) and certain non-radicals that are either oxidizing agents and/or are easily converted into radicals. Nitrogen-containing oxidizing agents, such as nitric oxide are also called reactive nitrogen species (RNS). ROS generation is generally a cascade of reactions that starts with the production of superoxide. Superoxide rapidly dismutates to hydrogen peroxide either spontaneously, particularly at low pH or catalyzed by superoxide dismutase. Other elements in the cascade of ROS generation include the reaction of superoxide with nitric oxide to form peroxynitrite, the peroxidase-catalyzed formation of hypochlorous acid from hydrogen peroxide, and the iron-catalyzed Fenton reaction leading to the generation of hydroxyl radical.

ROS avidly interact with a large number of molecules including other small inorganic molecules as well as DNA, proteins, lipids, carbohydrates and nucleic acids. This initial reaction may generate a second radical, thus multiplying the potential damage. ROS are involved not only in cellular damage and killing of pathogens, but also in a large number of reversible regulatory processes in virtually all cells and tissues. However, despite the importance of ROS in the regulation of fundamental physiological processes, ROS production can also irreversibly destroy or alter the function of the target molecule. Consequently, ROS have been increasingly identified as major contributors to damage in biological organisms, so-called "oxidative stress".

During inflammation, NADPH oxidase is one of the most important sources of ROS production in vascular cells under inflammatory conditions (Thabut et al., 2002, *J. Biol. Chem.*, 277:22814-22821).

In the lung, tissues are constantly exposed to oxidants that are generated either endogenously by metabolic reactions (e.g. by mitochondrial respiration or activation of recruited inflammatory cells) or exogenously in the air (e.g. cigarette smoke or air pollutants). Further, the lungs, constantly exposed to high oxygen tensions as compared to other tissues, have a considerable surface area and blood supply and are particularly susceptible to injury mediated by ROS (Brigham, 1986, *Chest*, 89(6): 859-863). NADPH oxidase-dependent ROS generation has been described in pulmonary endothelial cells and smooth muscle cells. NADPH oxidase activation in response to stimuli has been thought to be involved in the development of respiratory disorders such as pulmonary hypertension and enhancement of pulmonary vasoconstriction (Djordjevic et al., 2005, *Arterioscler. Thromb. Vasc. Biol.*, 25, 519-525; Liua et al., 2004, *Am. J. Physiol. Lung, Cell. Mol. Physiol.*, 287: L111-118). Further, pulmonary fibrosis has been characterized by lung inflammation and excessive generation of ROS.

Osteoclasts, which are macrophage-like cells that play a crucial role in bone turn-over (e.g. bone resorption), generate ROS through NADPH oxidase-dependent mechanisms (Yang et al., 2002, *J. Cell. Chem.* 84, 645-654).

Diabetes is known to increase oxidative stress (e.g. increased generation of ROS by auto-oxidation of glucose) both in humans and animals and increased oxidative stress has been said to play an important role in the development of diabetic complications. It has been shown that increased peroxide localization and endothelial cell dysfunction in the central retina of diabetic rats coincides with the areas of NADPH oxidase activity in the retinal endothelial cells (Ellis et al., 2000, *Free Rad. Biol. Med.*, 28:91-101). Further, it has been suggested that controlling oxidative stress (ROS) in mitochondria and/or inflammation may be a beneficial approach for the treatment of diabetes (Pillarisetti et al., 2004, *Expert Opin. Ther. Targets*, 8(5):401-408).

ROS are also strongly implicated in the pathogenesis of atherosclerosis, cell proliferation, hypertension and reperfusion injury cardiovascular diseases in general (Cai et al., 2003, *Trends Pharmacol. Sci.*, 24:471-478). Not only is superoxide production, for example in the arterial wall, increased by all risk factors for atherosclerosis, but ROS also induce many "proatherogenic" in vitro cellular responses. An important consequence of the formation of ROS in vascular cells is the consumption of nitric oxide (NO). NO inhibits the development of vascular diseases, and loss of NO is important in the pathogenesis of cardiovascular diseases. The increase in NADPH oxidase activity in vascular wall after balloon injury has been reported (Shi et al., 2001, *Throm. Vasc. Biol.*, 2001, 21, 739-745)

It is believed that oxidative stress or free radical damage is also a major causative factor in neurodegenerative diseases. Such damages may include mitochondrial abnormalities, neuronal demyelination, apoptosis, neuronal death and reduced cognitive performance, potentially leading to the development of progressive neurodegenerative disorders (Nunomura et al., 2001, *J. Neuropathol. Exp. Neurol.*, 60:759-767; Girouard, 2006, *J. Appl. Physiol.* 100:328-335).

Further, the generation of ROS by sperm has been demonstrated in a large number of species and has been suggested to be attributed to an NADPH oxidase within spermatozoa (Vernet et al., *Biol. Reprod.*, 2001, 65:1102-1113). Excessive ROS generation has been suggested to be implicated in sperm pathology, including male infertility and also in some penile disorders and prostate cancer.

Oxidative stress through reactive oxygen species generation by an NADPH oxidase has been shown to be responsible of neuropathological alterations in a rat model of chronic psychosocial stress and involved in psychotic disorders and social isolation processes.

Further, ROS have been shown to be associated with increased mitotic rate, angiogenesis, migration of adenocarcinoma cells and cell differentiation Lambeth et al. 2008, *Semin. Immunopathol.*, 2008, 30, 339-363) and NOX inhibitors have been shown able to reduce tumour vascularization (tumour angiogenesis) and tumour growth in a curative model in a similar extent to that of an anti-VEGFR2 antibody (DC101) (Garrido-Urbani, 2011, *PLoS ONE*, 6(2)).

NADPH oxidases are multi-subunit enzymes made up of a membrane-bound cytochrome b558 domain and three cytosolic protein subunits, p47phox, p67phox and a small GTPase, Rac. Seven isoforms of NOX enzymes have been identified including NOX1, NOX2, NOX3, NOX4, NOX5, DUOX1 and DUOX2 (Leto et al., 2006, *Antioxid. Redox Signal*, 8(9-10):1549-61; Cheng et al., 2001, *Gene*, 16; 269 (1-2):131-40).

In particular, excessive vascular and colon epithelial ROS production by Nox1 isoform has been found as being implicated in the development and progression of a wide spectrum of diseases a number of disease states, including cardiovascular disorders and in particular hypertension and atherosclerosis, neurodegenerative diseases, liver fibrosis, cancer, in particular in colon cancer, ischemic conditions, in particular ischemic retinopathies and neoplasia.

It has been found that ROS generation by the Nox1 member of the Nox family is necessary for the formation of extracellular matrix (ECM)-degrading, actin-rich cellular structures known as invadopodia. A peptide mimicking a putative activation domain of the NOX1 activator NOXA1 was developed as Nox-1 inhibitor and was described as being able to attenuate endothelial cell migration (Rynayhossani et al., 2013, *J. Bio. Chem.*, 288(51):36437-50). A subset of phenothiazines, 2-acetylphenothiazine (referred to as ML171 and its related 2-(trifluoromethyl)-phenothiazine) have been found to be Nox1 inhibitors that potently block Nox1-dependent ROS generation. ML171 also blocks the ROS-dependent formation of ECM-degrading invadopodia in colon cancer cells (Gianni et al., 2010, *ACS Chem. Biol.*, 5(10):981:93). Further, NOX1 selective inhibition has been found to be a potential strategy for treatment for a range of ischemic retinopathies (Wilkinson-Berka et al., 2014, *Antioxid. Redox Signal*, 20(17):2726-40) since NOX1 has been reported to mediate vascular injury in ischemic retinopathy. Very recently, peptidic inhibitors of NOX1 have been developed (WO 2014/106649) for treating and/or preventing cancer, atherosclerosis, angiogenesis, and aging and other Nox1 inhibitors have been developed for the protection of pancreatic beta cells (WO 2014/153227). Further, it was recently determined that NOX1 is an important contributor to ROS production and cell death of the alveolo-capillary barrier in acute lung injury and that NOX1 silencing prevented ROS generation and cell death in lung epithelial cells (Carnesecchi et al., 2009, *American Journal of Respiratory and Critical Care Medicine;* 180(10):972-981).

Thus, ROS derived from NOX1 contribute to the pathogenesis of numerous diseases, and therefore, it would be highly desirable to develop new active agents clinically useful inhibitors of the Nox enzymes, in particular selective for Nox1.

SUMMARY OF THE INVENTION

The present invention is directed towards new molecules useful in the treatment and/or prophylaxis of Nicotinamide adenine dinucleotide phosphate oxidase (NADPH Oxidase) related disorders such as cardiovascular diseases, neurodegenerative diseases, kidney diseases, liver disorders, inflammatory disorders, cancers, fibrotic disorders, psychotic disorders, angiogenesis, infectious diseases, and angiogenesis-dependent conditions. Notably, the invention is related to new molecules useful in the inhibition or reduction of ROS production in cells.

A first aspect of the invention provides a derivative according to Formula (I), as well as tautomers, geometrical isomers, optically active forms, pharmaceutically acceptable salts and pharmaceutically active derivative thereof.

Another aspect of the invention relates to a derivative according to the invention for use as a medicament.

Another aspect of the invention relates to a pharmaceutical composition containing at least one derivative according to the invention.

Another aspect of the invention resides in a use of a derivative according to the invention as tautomers, geometrical isomers, optically active forms, pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, diseases or disorders of the gastrointestinal system, angiogenesis and angiogenesis-dependent and/or other diseases and disorders associated with Nicotinamide adenine dinucleotide phosphate oxidase (NADPH Oxidase).

Another aspect of the invention relates to a method for treating a patient suffering from a disease or condition selected from cardiovascular disorders, respiratory disorders, metabolic disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase). The method comprises administering a derivative according to the invention or a formulation thereof in a patient in need thereof.

Another aspect of the invention relates to a derivative according to the invention for the treatment of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase).

Another aspect of the invention provides a process for the preparation of compounds of Formula (I) or a pharmaceutically acceptable salt thereof.

Another aspect of the invention provides an intermediate of compounds of Formula (I) according to the invention.

Other features and advantages of the invention will be apparent from the following detailed description.

DETAILED DESCRIPTION OF THE INVENTION

Figure 1A:
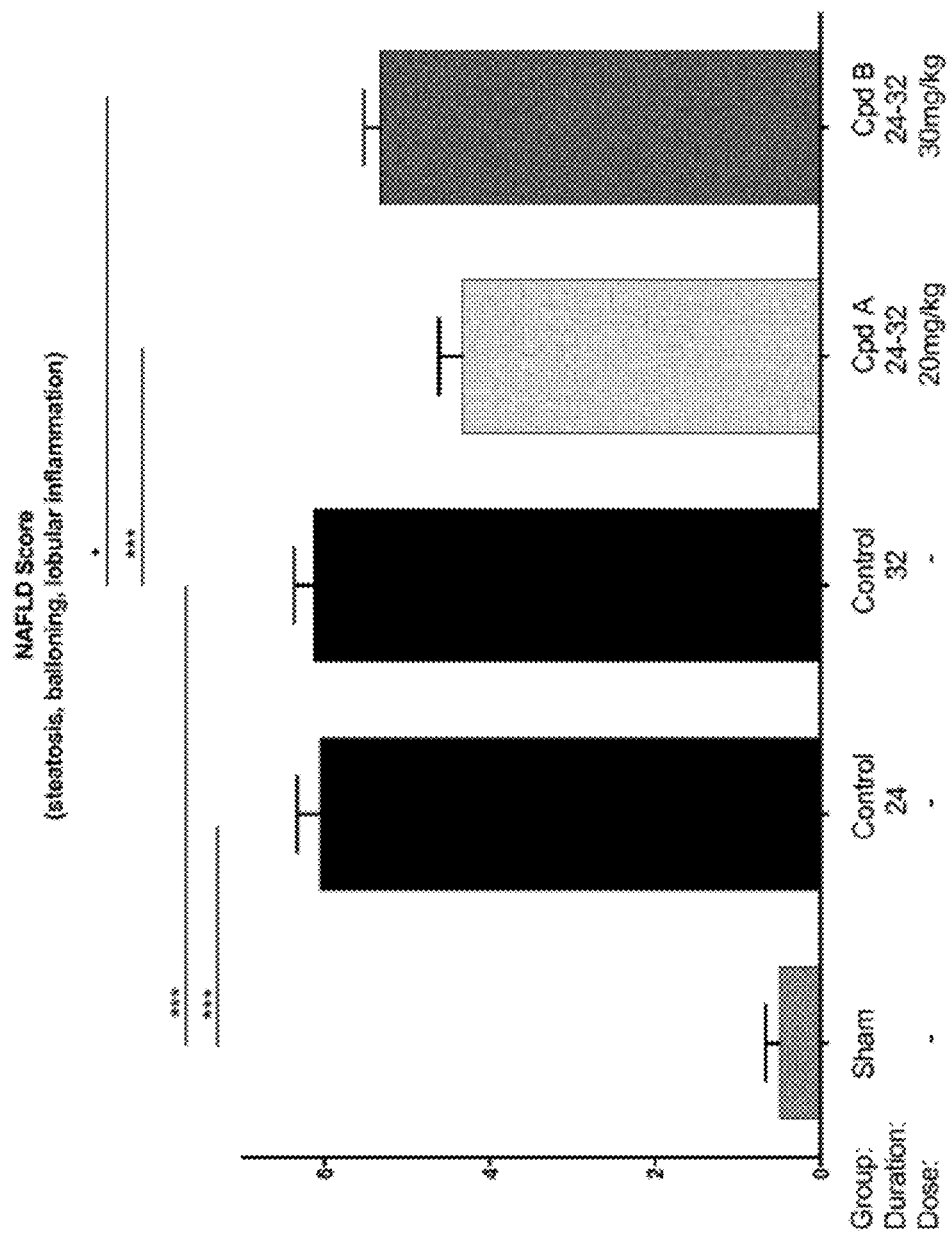
FIG. 1 shows the Non-Alcoholic Fatty Liver Disease (NAFLD) score (A) and the metabolic marker plasma aspartate aminotransferase (AST) (B) as measured in a non alcoholic steatohepatitis (NASH) model as described in Example 125 in presence of a compound (A or B) of the invention compared to control.

The following paragraphs provide definitions of the various chemical moieties that make up the compounds according to the invention and are intended to apply uniformly through-out the specification and claims, unless an otherwise expressly set out definition provides a broader definition.

The term "alkyl" when used alone or in combination with other terms, comprises a straight chain or branched $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refer respectively to monovalent alkyl groups having 1 to 9 carbon atoms, monovalent alkyl groups having 1 to 6 carbon atoms and monovalent alkyl groups having 1 to 4 carbon atoms. Particularly, those include $C_1$-$C_6$ alkyl.

The term "alkenyl" when used alone or in combination with other terms, comprises a straight chain or branched $C_2$-$C_{20}$ alkenyl. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3, 7, 11, 15-tetramethyl-1-hexadecenyl, and the like. Preferably, these include $C_2$-$C_8$ alkenyl, more preferably $C_2$-$C_6$ alkenyl. Among others, especially preferred are vinyl or ethenyl (—CH═CH$_2$), n-2-propenyl (allyl, —CH$_2$CH═CH$_2$), iso-propenyl, 1-propenyl, 2-methyl-1-propenyl, 1-butenyl, 2-butenyl, and 3-methyl-2-butenyl and the like.

The term "alkynyl" when used alone or in combination with other terms, comprises a straight chain or branched $C_2$-$C_{20}$ alkynyl. It may have any available number of triple bonds in any available positions. This term is exemplified by groups such as alkynyl groups that may have a carbon number of 2-20, and optionally a double bond, such as ethynyl (—C≡CH), 1-propynyl, 2-propynyl (propargyl: —CH$_2$C≡CH), 2-butynyl, 2-pentene-4-ynyl, and the like. Particularly, these include $C_2$-$C_8$ alkynyl, more preferably $C_2$-$C_6$ alkynyl and the like. Preferably those include $C_2$-$C_6$ alkynyl which refers to groups having 2 to 6 carbon atoms and having at least 1 or 2 sites of alkynyl unsaturation.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "$C_1$-$C_6$ alkyl aryl" refers to aryl groups having a $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b] pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_1$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include azetidinyl, pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl) methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "$C_1$-$C_6$ alkyl," preferably "$C_1$-$C_6$alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl", "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to $C_1$-$C_6$ alkyl groups having an acyloxy substituent, including 2-(ethylcarbonyloxy) ethyl and the like.

The term "alkoxy" refers to the group —O—R where R includes "$C_1$-$C_6$ alkyl", "aryl", "heteroaryl", "aryl $C_1$-$C_6$ alkyl" or "heteroaryl $C_1$-$C_6$ alkyl". Preferred alkoxy groups include for example, methoxy, ethoxy, phenoxy and the like.

The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R' and R" are independently H, "$C_1$-$C_6$ alkyl," "$C_2$-$C_6$ alkenyl," "alkynyl," "$C_3$-$C_8$-cycloalkyl," "heterocycloalkyl," "$C_1$-$C_6$ aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$ alkyl groups having an ureido substituent, including 2-(N'-methylureido) ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "amino alkyl" refers to alkyl groups having an amino substituent, including 2-(1-pyrrolidinyl)ethyl and the like.

The term "ammonium" refers to a positively charged group —N$^+$RR'R" where R, R' and R" are independently "$C_1$-$C_6$ alkyl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "ammonium alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "$C_1$-$C_6$ alkyl," "$C_1$-$C_6$ alkyl" substituted with halogens, e.g., an —OSO$_2$—CF$_3$ group, "$C_2$-$C_6$ alkenyl," "alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl alkyl".

The term "sulfonyloxy $C_1$-$C_6$ alkyl" refers to alkyl groups having a sulfonyloxy substituent, including 2-(methylsulfonyloxy) ethyl and the like.

The term "sulfonyl" refers to group "—SO$_2$—R" wherein R is selected from "aryl," "heteroaryl," "$C_1$-$C_6$ alkyl," "$C_1$-$C_6$ alkyl" substituted with halogens, e.g., an —SO$_2$—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl) ethyl and the like.

The term "sulfinyl" refers to a group "—S(O)—R" wherein R is selected from "alkyl," "alkyl" substituted with halogens, e.g., a —SO—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl alkyl" refers to alkyl groups having a sulfinyl substituent, including 2-(methylsulfinyl) ethyl and the like.

The term "sulfanyl" refers to groups —S—R where R includes H, "$C_1$-$C_6$ alkyl," "$C_1$-$C_6$ alkyl" substituted with halogens, e.g., a —S—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "cycloalkyl $C_1$-$C_6$ alkyl," or "heterocycloalkyl $C_1$-$C_6$ alkyl". Preferred sulfanyl groups include methylsulfanyl, ethylsulfanyl, and the like.

The term "sulfanyl $C_1$-$C_6$ alkyl" refers to $C_1$-$C_5$-alkyl groups having a sulfanyl substituent, including 2-(ethylsulfanyl) ethyl and the like.

The term "sulfonylamino" refers to a group —NRSO$_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino) ethyl and the like.

The term "aminosulfonyl" refers to a group —SO$_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, all the above substituents should be understood as being all optionally substituted.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl cycloalkyl," "$C_1$-$C_6$ alkyl heterocycloalkyl," "cycloalkyl $C_1$-$C_6$ alkyl," "heterocycloalkyl $C_1$-$C_6$ alkyl," "amino," "aminosulfonyl," "ammonium," "alkoxy," "acyl amino," "amino carbonyl," "aryl," "aryl $C_1$-$C_6$ alkyl," "heteroaryl," "heteroaryl $C_1$-$C_6$ alkyl," "sulfinyl," "sulfonyl," "sulphonamide," "alkoxy," "alkoxy carbonyl," "carbamate," "sulfanyl," "halogen," "carboxy," trihalomethyl, cyano, hydroxy, mercapto, nitro, and the like.

The term "pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition such as salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compound according to the invention and presenting NADPH oxidase inhibiting activity that has a chemically or metabolically decomposable group, and a compound that may be converted into a pharmaceutically active compound in vivo by solvolysis under physiological conditions. The invention further encompasses any tautomers of the compounds according to the invention.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, myocardial infarction, hypertension, formation of atherosclerotic plaques, platelet aggregation, angina pectoris, aneurysm, aortic dissection, ischemic heart disease, ischemic retinopathies, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD). The term "infectious disorder or disease" includes a disorder caused by organisms such as bacteria, viruses or parasites. Many organisms live in and on our bodies. It includes but is not limited to infectious diseases of the lung, influenza and other conditions caused by virus infections.

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease" or disorder" includes psoriasis, eczema, scleroderma, xeroderma pigmentosum, skin cancers, melanoma, erythropoietic protoporphyria, discoid lupus erythematosus, solar urticaria, polymorphous light eruption, dermatitis, wound healing and scar formation.

The term "bone disorder" includes osteoporosis, osteoarthritis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuro-inflammatory and demyelinating states or diseases such as leukoencephalopathies, and leukodystrophies.

The term "demyelinating" is referring to a state or a disease of the CNS comprising the degradation of the myelin around the axons. In the context of the invention, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury.

Preferably, the condition is multiple sclerosis.

The term "psychotic disorder" includes disorders also known as behavioural disorders or mood disorders and refers to a group of disorders characterized by dramatic changes or extremes of mood which can be for example diagnosed as described in Diagnostic and Statistical Manual of Mental Disorders-5th Edition Text Revision (DMS-V-TR), American Psychiatric Press, 2013. It includes schizophrenia, schizoaffective disorder, schizophreniform disorder, delusional disorder, psychotic depression, or mania with psychosis.

The term "kidney disease or disorder" includes diabetic nephropathy, renal failure, glomerulonephritis, nephrotoxicity of aminoglycosides and platinum compounds and hyperactive bladder. In a particular embodiment, the term according to the invention includes chronic kidney diseases or disorders.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathies like Glaucoma, Aged-related Macular degeneration (AMD), Dry eye syndrome and allergic conjonctivits.

The term "conditions affecting the inner ear" includes presbycusis, tinnitus, Meniere's disease and other balance problems, utriculolithiasis, vertigo, vestibular migraine, and noise-induced hearing loss and drug-induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutic effective dose of a compound expressed by Formula (I) in a sufficient dose to inhibit NADPH oxidase. Those include skin inflammation such as psoriasis, atopic dermitis, pruritis, joint inflammation such rheumatoid arthritis, psoriatic arthritis, reactive artithris, Bechet's disease, ankylosing spondylarthitis, osteoarthritis, liver inflammation such as viral hepatitis, autoimmune hepatitis and entral nervous system inflammation such as multiple sclerosis.

The term "liver diseases or disorders" include liver fibrosis, alcohol induced fibrosis, steatosis and non alcoholic steatohepatitis (NASH).

The term "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by Formula (I) in a sufficient dose to inhibit NADPH oxidase.

The term "pain" includes hyperalgesia associated with inflammatory pain and neurogenic pain. Neuropathic pain includes diabetic neuropathy, spinal or nerve injury related pain, amputation, drug induced pain, multiple sclerosis, multiple myeloma, shingles, Lyme disease, Herpes Zoster infection, cancer related pain, HIV-related pain, trigeminal neuralgia. Inflammatory pain includes pelvic pain including endometriosis, fibromyalgia, joint pain associated with inflammatory disorders, burn related pain, trauma-induced pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer, melanoma), neoplasia or the related diseases which require the administration to a mammal in a therapeutic effective dose of a compound expressed by the Formula (I) in a sufficient dose to inhibit NADPH oxidase. In particular, disorders induced by the toxicity of some drugs such as cancer therapies (e.g. Doxorubicin).

The term "disease or disorders of the gastrointestinal system", includes gastric mucosa disorders ischemic bowel disease management, enteritis/colitis/Crohn's Disease, cancer chemotherapy, or neutropenia.

The term "angiogenesis" includes sprouting angiogenesis, intussusceptive angiogenesis, vasculogenesis, arteriogenesis and lymphangiogenesis. Angiogenesis is the formation of new blood vessels from pre-existing capillaries or post-capillary venules and occurs in pathological conditions such as cancers, arthritis and inflammation. A large variety of tissues, or organs comprised of organized tissues, can support angiogenesis in disease conditions including skin, muscle, gut, connective tissue, joints, bones and the like tissue in which blood vessels can invade upon angiogenic stimuli. As used herein, the term "angiogenesis-dependent condition" is intended to mean a condition where the process of angiogenesis or vasculogenesis sustains or augments a pathological condition. Vasculogenesis results from the formation of new blood vessels arising from angioblasts which are endothelial cell precursors. Both processes result in new blood vessel formation and are included in the meaning of the term angiogenesis-dependent conditions. Similarly, the term "angiogenesis" as used herein is intended to include de novo formation of vessels such as those arising from vasculogenesis as well as those arising from branching and sprouting of existing vessels, capillaries and venules. Angiogenic disorders include solid tumors, endometriosis, benign and malignant vascular tumors and proliferative retinopathies.

The term "angiogenesis inhibitory" means, which is effective in the decrease, in the extent, amount, or rate of neovascularization. Effecting a decrease in the extent, amount, or rate of endothelial cell proliferation or migration in the tissue is a specific example of inhibiting angiogenesis. Angiogenesis inhibitory activity is particularly useful in the treatment of any cancers as it targets tumor growth process and in the absence of neovascularization of tumor tissue, the tumor tissue does not obtain the required nutrients, slows in growth, ceases additional growth, regresses and ultimately becomes necrotic resulting in killing of the tumor. Further, an angiogenesis inhibitory activity is particularly useful in the treatment of any cancers as it is particularly effective against the formation of metastases because their formation also requires vascularization of a primary tumor so that the metastatic cancer cells can exit the primary tumor and their establishment in a secondary site requires neovascularization to support growth of the metastases.

The term "fibrotic disease or disorder" refers to diseases or disorders characterized by the development of excess fibrous connective tissue as a reparative response to injury or damage and includes pulmonary fibrosis, kidney fibrosis, liver fibrosis, retinal fibrosis, skin fibrosis, retroperitoneal fibrosis and heart fibrosis. Liver fibrosis includes non-alcoholic steatohepatitis, alcoholic steatohepatitis, primary biliary cholangitis, primary sclerosing cholangitis, autoimmune hepatitis, viral hepatitis, progressive familial intrahepatic cholestasis. Lung fibrosis includes idiopathic pulmonary fibrosis, chronic obstructive lung disease, severe asthma, pulmonary hypertension, systemic sclerosis. Kidney fibrosis includes hypertensive kidney disease, diabetic kidney disease, focal segmental glomerulosclerosis, IgA nephropathy. Skin fibrosis includes systemic sclerosis, burn-induced skin fibrosis, trauma-induced skin fibrosis. Corneal fibrosis includes corneal surgery-induced fibrosis, trauma-induced corneal fibrosis, dry eye syndrome, Sjögren's syndrome.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions. Treatment can be as single agent or in combination with other therapies.

The term "subject" as used herein refers to mammals. For examples, mammals contemplated by the present invention include human, primates, domesticated animals such as cattle, sheep, pigs, horses and the like.

The term "inhibitor" used in the context of the invention is defined as a molecule that inhibits completely or partially the activity of NADPH oxidase and/or inhibit or reduce the generation of reactive oxygen species (ROS).

Compounds According to the Invention

In one embodiment, the invention provides a compound according to Formula (I):

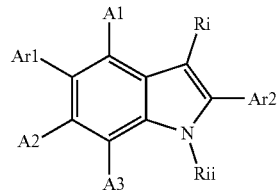

Formula (I)

Wherein $A_1$, $A_2$ and $A_3$ groups are independently selected from hydrogen, halogen (e.g. fluoro, chloro), CN, $CF_3$, $CHF_2$, an optionally substituted radical selected from $C_1$-$C_6$ alkyl (e.g. methyl), $C_3$-$C_8$ cycloalkyl, heteroalkyl, heterocycloalkyl, alkoxy (e.g. methoxy), amino, carboxy, alkoxycarbonyl; $R^i$ is selected from the group of hydrogen, halogen (e.g. chloro), CN, $CF_3$, $CHF_2$, an optionally substituted radical selected from $C_1$-$C_6$ alkyl, $C_3$-$C_8$ cycloalkyl, heteroalkyl, heterocycloalkyl, carboxy; $R^{ii}$ is hydrogen or an optionally substituted $C_1$-$C_6$ alkyl (e.g. methyl, ethyl, iso-propyl, cyclopropylmethyl, dimethyl acetamide methyl, oxetan-3-yl methyl, benzyl, acetamide), an optionally substituted $C_3$-$C_8$ cycloalkyl (e.g. cyclopropyl), an optionally substituted halo $C_1$-$C_6$ alkyl, an optionally substituted halo $C_3$-$C_8$ cycloalkyl, an optionally substituted aryl $C_1$-$C_6$ alkyl (e.g. benzyl), an optionally substituted hereroaryl $C_1$-$C_6$ alkyl, an optionally substituted heteroalkyl, an optionally substituted heterocycloalkyl, an optionally substituted heterocycloalkyl $C_1$-$C_6$ alkyl (e.g. oxetan-3-yl methyl), an optionally substituted hydroxy $C_1$-$C_6$ alkyl (e.g. ethanol), an optionally substituted alkoxy $C_1$-$C_6$ alkyl (e.g. 2-methoxy ethyl), an optionally substituted alkoxycarbonyl $C_1$-$C_6$ alkyl (e.g., methyl acetate), an optionally substituted aminocarbonyl $C_1$-$C_6$ alkyl (e.g. acetamide methyl, dimethyl acetamide methyl), an optionally substituted aryl $C_3$-$C_8$ cycloalkyl, an optionally substituted hereroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted halo $C_3$-$C_8$ cycloalkyl; $Ar^1$ is selected from:

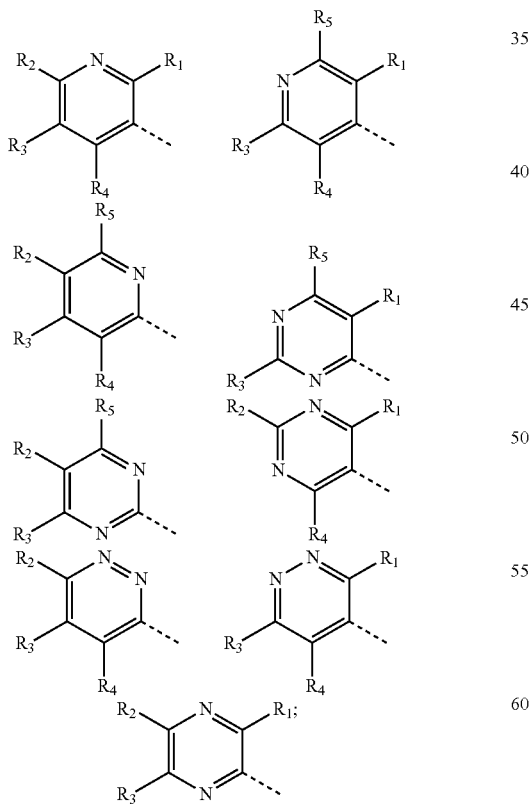

$R^1$ and $R^4$ are independently hydrogen, halogen, CN, $CF_3$, $CHF_2$, $NH_2$, an optionally substituted $C_1$-$C_6$ alkyl (e.g. methyl), an optionally substituted $C_3$-$C_8$ cycloalkyl, alkoxy (e.g. methoxy), amino, an optionally substituted heterocycloalkyl, carboxy, an optionally substituted alkoxy $C_1$-$C_6$ alkyl, an optionally substituted alkoxy $C_3$-$C_8$ cycloalkyl, an optionally substituted amino $C_1$-$C_6$ alkyl, an optionally substituted amino $C_3$-$C_8$ cycloalkyl, an optionally substituted amino heterocycloalkyl $C_1$-$C_6$ alkyl, an optionally substituted carboxy $C_3$-$C_8$ cycloalkyl, an optionally substituted aminocarbonyl $C_1$-$C_6$ alkyl;

$R^2$ is selected from hydrogen, halogen (e.g. fluoro, chloro), $CF_3$, $CHF_2$, $NH_2$, an optionally substituted $C_1$-$C_6$ alkyl (e.g. methyl), an optionally substituted $C_3$-$C_8$ cycloalkyl (e.g. cyclopropyl), an optionally substituted alkoxy (e.g. methoxy, ethoxy, cyclopropyloxy, iso-propyloxy, cyclopropylmethyloxy, benzyloxy), amino (e.g. amino, methylamino, dimethyl amino), an optionally substituted heterocycloalkyl (e.g. morpholinyl, 1-methylpiperazine), carboxy, an optionally substituted alkoxy $C_1$-$C_6$ alkyl (e.g. methoxymethyl), an optionally substituted alkoxy $C_3$-$C_8$ cycloalkyl, an optionally substituted amino $C_1$-$C_6$ alkyl, an optionally substituted amino $C_3$-$C_8$ cycloalkyl, an optionally substituted amino heterocycloalkyl $C_1$-$C_6$ alkyl, an optionally substituted $C_3$-$C_8$ carboxy cycloalkyl, an optionally substituted aminocarbonyl $C_1$-$C_6$ alkyl; $R^3$ is selected from hydrogen, halogen (e.g. fluoro, chloro), $CF_3$, $CHF_2$, $NH_2$, an optionally substituted $C_1$-$C_6$ alkyl (e.g. methyl), an optionally substituted $C_3$-$C_8$ cycloalkyl (e.g. cyclopropyl), an optionally substituted alkoxy (e.g. methoxy, ethoxy, cyclopropyloxy, iso-propyloxy, cyclopropylmethyloxy), amino (e.g. amino, methylamino, dimethyl amino), an optionally substituted heterocycloalkyl (e.g. morpholinyl, 1-methylpiperazine), carboxy, an optionally substituted alkoxy $C_1$-$C_6$ alkyl (e.g. methoxymethyl), an optionally substituted alkoxy $C_3$-$C_8$ cycloalkyl, an optionally substituted amino $C_1$-$C_6$ alkyl, an optionally substituted amino $C_3$-$C_8$ cycloalkyl, an optionally substituted amino heterocycloalkyl $C_1$-$C_6$ alkyl, an optionally substituted $C_3$-$C_8$ carboxy cycloalkyl, an optionally substituted aminocarbonyl $C_1$-$C_6$ alkyl; $R^5$ is selected from hydrogen, halogen, $CF_3$, $CHF_2$, $NH_2$, an optionally substituted $C_1$-$C_6$ alkyl (e.g. methyl), an optionally substituted $C_3$-$C_8$ cycloalkyl (e.g. cyclopropyl), an optionally substituted alkoxy (e.g. methoxy, cyclopropyloxy), amino (e.g. amino, methylamino, dimethyl amino), an optionally substituted heterocycloalkyl (e.g. morpholinyl, 1-methylpiperazine), carboxy, an optionally substituted alkoxy $C_1$-$C_6$ alkyl, an optionally substituted alkoxy $C_3$-$C_8$ cycloalkyl, an optionally substituted amino $C_1$-$C_6$ alkyl, an optionally substituted amino $C_3$-$C_8$ cycloalkyl, an optionally substituted amino heterocycloalkyl $C_1$-$C_6$ alkyl, an optionally substituted $C_3$-$C_8$ carboxy cycloalkyl, an optionally substituted aminocarbonyl $C_1$-$C_6$ alkyl; wherein when one from $R^1$, $R^2$, $R^3$ and $R^4$ is not H, the other from this group are H or any of R, $R^2$, $R^3$, $R^4$ and $R^5$ can be linked together to form an optionally substituted bicyclic heteroaryl (e.g. 3,4-dihydro-2H-pyrido[3,2-b][1,4]oxazine, thieno[2,3-c] pyridine-4-yl); $Ar^1$ is also selected from an optionally substituted bicyclic heteroaryl, in particular from the group consisting of:

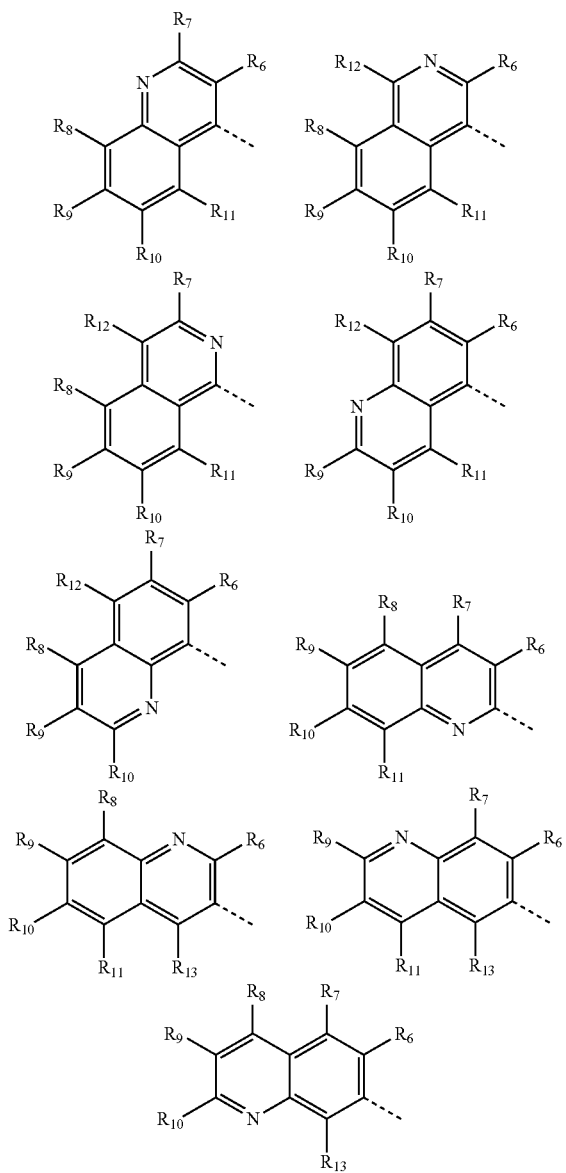

wherein $R^6$, $R^7$, $R^8$, $R^9$, $R^{10}$, $R^{11}$, $R^{12}$ and $R^{13}$ are each independently selected from hydrogen, halogen, hydroxy, CN, $CF_3$, $CHF_2$, $NH_2$, alkoxy, amino, carboxy, aminocarbonyl, alkoxy carbonyl, or an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl, acylamino, ureido, sulfonyl, sulfonylamino; $R^{14}$ is selected from hydrogen, aminocarbonyl, alkoxy carbonyl, or an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, carboxy $C_1$-$C_6$ alkyl, an optionally substituted aminocarbonyl $C_1$-$C_6$ alkyl, an optionally substituted heterocycloalkyl $C_3$-$C_8$ cycloalkyl, aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl; $Ar^2$ is selected from the following group:

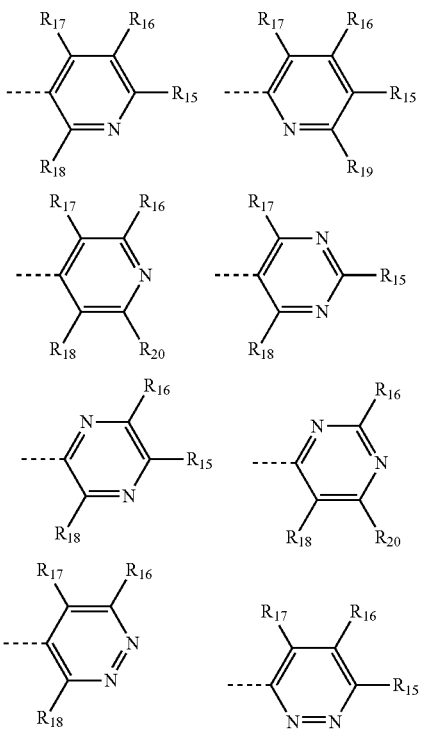

or from the following group:

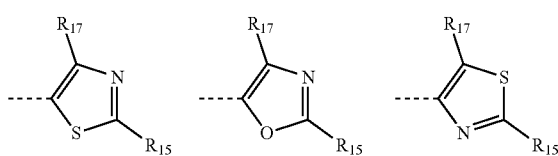

-continued

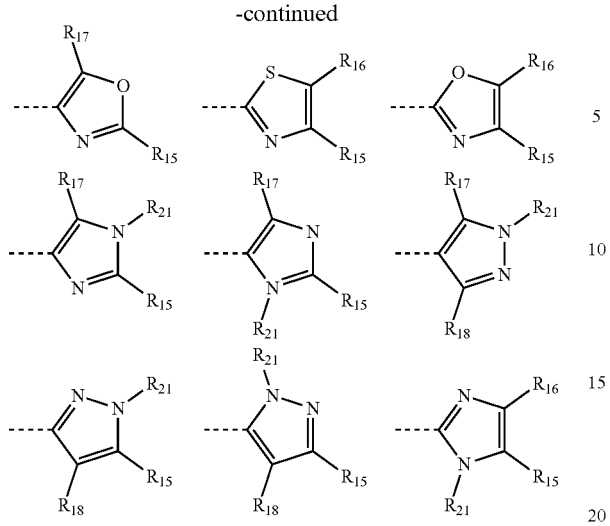

or from the following group:

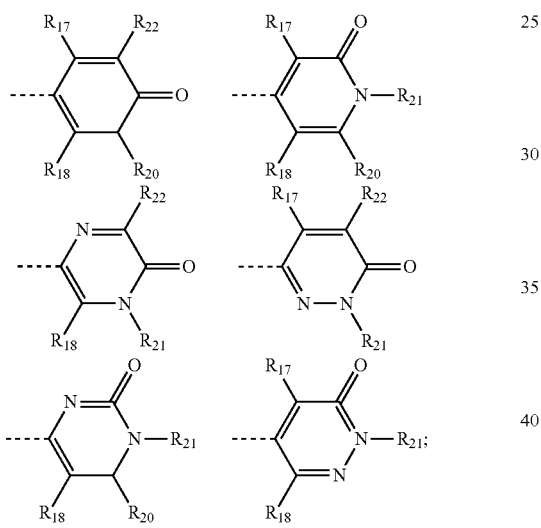

Wherein $R^{15}$, $R^{16}$ and $R^{19}$ are independently selected from hydrogen, halogen (e.g. fluoro), hydroxy, CN, $CF_3$, $CHF_2$, $NH_2$, alkoxy (e.g. methoxy), amino (e.g. dimethylamino), carboxy, aminocarbonyl, alkoxy carbonyl, an optionally substituted $C_1$-$C_6$ alkyl (e.g. methyl), an optionally substituted $C_3$-$C_8$ cycloalkyl (e.g. cyclopropyl), an optionally substituted alkenyl, alkynyl, an optionally substituted haloalkyl, an optionally substituted heteroalkyl, an optionally substituted heterocycloalkyl (e.g. 4,4-difluoropiperidin-1-yl, morpholinyl, thiomorpholinyl 1,1-dioxide, optionally substituted piperazinyl such as piperazin-1-yl pyridine-3-yl or 4-ethylpiperazinyl, 1-methylpiperazine-2one), an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl, acylamino, ureido and sulfonyl, or selected from the groups listed below:

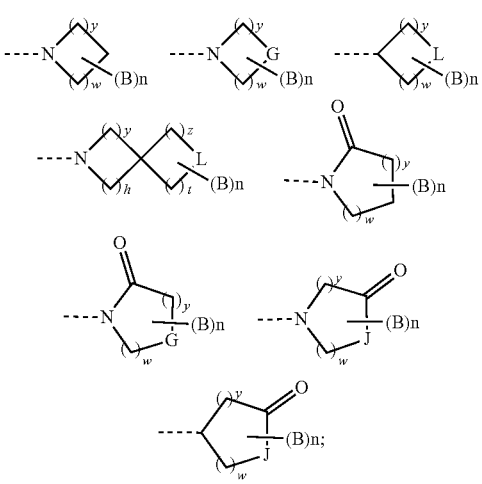

Wherein y, w, z and t are independently an integer ranging from 1 to 3; h is an integer ranging from 0 to 3; n is an integer ranging from 0 to 4; G is selected from N—$R^{23}$, O, S and $SO_2$; J is selected from C(B)n and N—$R^{23}$; L is C—(B)n, N—$R^{23}$, O, S, $SO_2$; $R^{23}$ is selected from hydrogen, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, alkoxy $C_1$-$C_6$ alkyl, an optionally substituted amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl and aminosulfonyl; B is selected from hydrogen, halogen, hydroxy, CN, $CF_3$, $CHF_2$, $NH_2$, alkoxy, amino, carboxy, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl, acylamino, ureido, sulfonyl and sulfonylamino; $R^{17}$ and $R^{18}$ are independently selected from hydrogen, halogen (e.g. fluoro), CN, $CF_3$, $CHF_2$, alkoxy, amino, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted $C_3$-$C_8$ cycloalkyl $C_1$-$C_6$ alkyl, an optionally substituted heterocycloalkyl $C_1$-$C_6$ alkyl, an optionally substituted alkoxy $C_1$-$C_6$ alkyl, an optionally substituted amino $C_1$-$C_6$ alkyl, an optionally substituted heterocycloalkyl $C_3$-$C_8$ cycloalkyl, an optionally substituted alkoxy $C_3$-$C_8$ cycloalkyl, an optionally substituted amino $C_3$-$C_8$ cycloalkyl, acylamino, ureido, sulfonyl, aminosulfonyl and sulfonylamino; $R^{20}$ and $R^{22}$ are independently selected from hydrogen, halogen, CN, $CF_3$, $CHF_2$, alkoxy, amino, an optionally substituted $C_1$-$C_6$ alkyl (e.g. methyl, cyclopentyl methyl), an optionally substituted $C_3$-$C_8$ cycloalkyl, an optionally substituted haloalkyl, an optionally substituted heteroalkyl, an optionally substituted heterocycloalkyl, an optionally substituted $C_3$-$C_8$ cycloalkyl $C_1$-$C_6$ alkyl (e.g. cyclopentyl methyl), an optionally substituted heterocycloalkyl $C_1$-$C_6$ alkyl, an optionally substituted alkoxy $C_1$-$C_6$ alkyl, an optionally substituted amino $C_1$-$C_6$ alkyl, an optionally substituted heterocycloalkyl $C_3$-$C_8$ cycloalkyl, an optionally substituted alkoxy $C_3$-$C_8$ cycloalkyl and an optionally substituted amino $C_3$-$C_8$ cycloalkyl; $R^{21}$ is selected from hydrogen, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl and an optionally substituted aminocarbonyl $C_3$-$C_8$ cycloalkyl; $R^{15}$ and $R^{16}$ can be linked together to form an optionally substituted bicyclic heteroaryl of formula

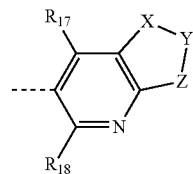

(e.g. furo[3,4-b]pyridine, 3,4-dihydro-2H-pyrido[3,2-b][1,4]oxazine), wherein X, Y and Z and each independently $C(R^{24}R^{25})$, $CH_2C(R^{24}R^{25})$, $C(=O)$, O and $N-R^{26}$; $R^{24}$ and $R^{25}$ are each independently selected from hydrogen, halogen, hydroxy, CN, $CF_3$, $CHF_2$, $NH_2$, alkoxy, amino, carboxy, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl, acylamino, ureido, sulfonyl and sulfonylamino; $R^{24}$ and $R^{25}$ can be linked together to form an optionally substituted $C_3$-$C_8$ cycloalkyl or an optionally substituted heterocycloalkyl (e.g. azetidine); $R^{26}$ is selected from hydrogen, aminocarbonyl, alkoxy carbonyl, an optionally substituted $C_1$-$C_6$ alkyl (e.g. methyl), an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl and an optionally substituted aminocarbonyl $C_3$-$C_8$ cycloalkyl, aminosulfonyl; $R^{15}$ and $R^{19}$ can be linked together to form an optionally substituted bicyclic heteroaryl; $R^{15}$ and $R^{21}$ can be linked together to form an optionally substituted bicyclic heteroaryl; $R^{17}$ and $R^{21}$ can be linked together to form an optionally substituted bicyclic heteroaryl; $R^{20}$ and $R^{21}$ can be linked together to form an optionally substituted bicyclic heteroaryl as well as tautomers, geometrical isomers, optically active forms, pharmaceutically acceptable salts thereof.

According to a particular embodiment, Ar1 is selected from the following groups:

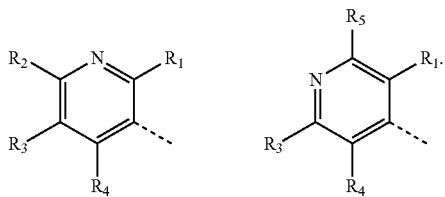

According to a particular embodiment, $R^2$ is selected from H, an optionally substituted $C_1$-$C_6$ alkyl (e.g. methyl) and $R^3$ is selected from an optionally substituted alkoxy (e.g. methoxy, ethoxy, cyclopropyloxy, iso-propyloxy, cyclopropylmethyloxy, benzyloxy), in particular methoxy.

According to a particular embodiment, Ar2 is selected from the following groups:

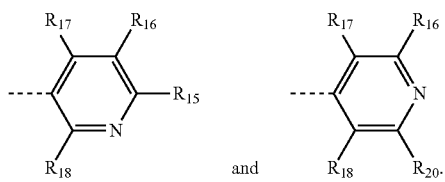

According to a particular aspect, is provided a compound according to Formula (I), with the proviso that the compound is not 2,5-di(pyridin-4-yl)-1H-indole-3-carbonitrile or 5-(pyridin-3-yl)-2-(pyridin-4-yl)-1H-indole-3-carbonitrile, as represented hereafter:

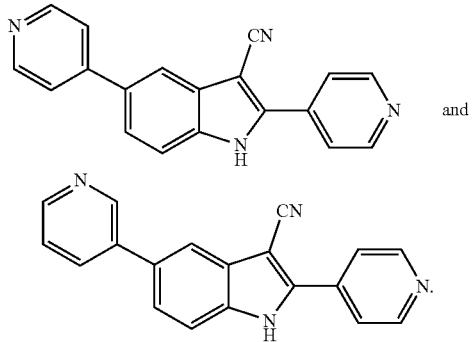

According to a particular aspect, is provided a compound according to Formula (I), with the proviso that the compound is not 2,5-di(pyridin-4-yl)-1H-indole-3-carbonitrile or 5-(pyridin-3-yl)-2-(pyridin-4-yl)-1H-indole-3-carbonitrile or 2,5-di(pyridin-3-yl)-1H-indole-3-carbonitrile.

According to a particular aspect, $R^i$ is H.

According to a particular aspect, $R^i$ is halogen, in particular chloro.

According to another particular aspect, $R^{ii}$ is H.

In another particular embodiment, $R^{ii}$ is optionally substituted $C_1$-$C_6$ alkyl such as optionally substituted methyl (e.g. methyl), optionally substituted ethyl (e.g. ethyl, methanol), optionally substituted isopropyl (e.g. 1-isopropyl), $C_1$-$C_6$ alkyl optionally substituted with alkoxy such as methoxy ethyl or with optionally substituted $C_2$-$C_8$ heterocycloalkyl such as oxetan methyl (e.g. oxetan-3-yl methyl) or with optionally substituted $C_3$-$C_8$ cycloalkyl (e.g. methyl cyclopropyl) or with optionally substituted aryl $C_1$-$C_6$ alkyl (e.g. benzyl), or with an optionally substituted amide $C_1$-$C_6$ alkyl (e.g. acetamide methyl, dimethyl acetamide methyl) or with optionally substituted acyl (e.g. methoxy carbonyl methyl). In another particular embodiment, $R^{ii}$ is optionally substituted $C_3$-$C_8$ cycloalkyl, such as an optionally substituted cyclopropyl.

According to a particular aspect, $A^1$, $A^2$ and $A^3$ are H.

In a particular embodiment, a compound of the invention is according to Formulae (Ia):

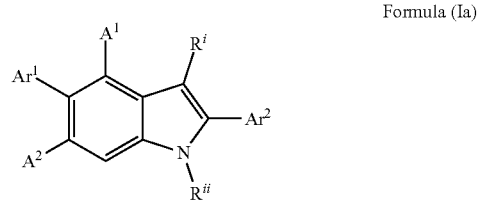

Formula (Ia)

wherein $Ar^1$, $Ar^2$, $R^i$; $R^{ii}$, $A^1$ and $A^2$; are as defined in the detailed description, wherein at least one $A_1$ and $A_2$ is not H.

In another particular embodiment, a compound of the invention is according to Formulae (Ib):

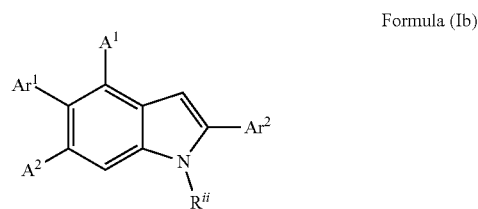

Formula (Ib)

wherein $Ar^1$, $Ar^2$, $R^{ii}$, $A_1$ and $A^2$; are as defined in the detailed description.

In another particular embodiment, a compound of the invention is according to according to Formulae (II):

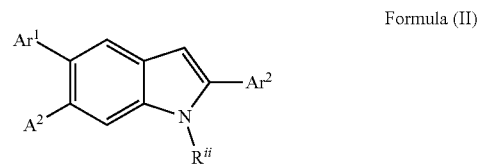

Formula (II)

wherein $Ar^1$, $Ar^2$, $R^{ii}$ and $A^2$; are as defined in the detailed description.

In another particular embodiment, a compound of the invention is according to according to Formulae (III):

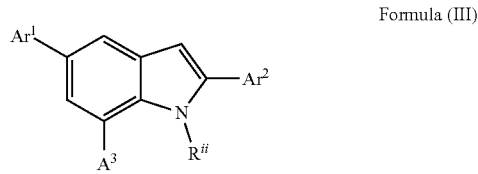

Formula (III)

wherein $Ar^1$, $Ar^2$, $R^{ii}$ and $A^3$; are as defined in the detailed description.

In a particular embodiment, $A^1$, $A^2$ and $A^3$ groups are independently selected from hydrogen, halogen (e.g. chloro, fluoro) and optionally substituted $C_1$-$C_6$ alkyl (e.g. methyl).

In a particular embodiment, $A^1$ is halogen, in particular chloro.

In another particular embodiment, $A^1$ is substituted $C_1$-$C_6$ alkyl, in particular methyl.

In a particular embodiment, $A^2$ is halogen, in particular chloro or fluoro.

In another particular embodiment, $A^1$ and $A^2$ groups are halogens, in particular fluoro.

In a particular embodiment, $A^3$ is halogen, in particular chloro.

In a further particular embodiment, $Ar^1$ is an optionally substituted pyridin-3-yl, such as pyridin-3-yl, a pyridin-3-yl substituted by one or more groups selected from optionally substituted $C_1$-$C_6$ alkyl (e.g. methyl), halogen (e.g. chloro, fluoro), optionally substituted $C_1$-$C_6$ alkoxy (e.g. methoxy, ethoxy, isopropyloxy, cyclopropyloxy, cyclopropylmethoxy, benzyloxy), $NH_2$, optionally substituted amino (e.g. dimethyl amino), optionally substituted $C_3$-$C_8$ cycloalkyl (e.g. cyclopropyl), optionally substituted alkoxy $C_1$-$C_6$ alkyl (e.g. methoxymethyl) and optionally substituted heterocycloalkyl (e.g. optionally substituted morpholinyl).

In another further particular embodiment, $Ar^1$ is an optionally substituted pyridin-3-yl, further fused to an optionally substituted aryl, such as an optionally substituted phenyl (e.g. to form a quinolyl or an isoquinolyl ring.

In another further particular embodiment, $Ar^1$ is an optionally substituted pyridin-3-yl, further fused to an optionally substituted heteroaryl, such as an optionally substituted thiophenyl (e.g. to form a thieno[2,3-c]pyridin-3-yl).

In another further particular embodiment, $Ar^1$ is an optionally substituted pyridin-3-yl, further fused to an optionally substituted heterocycloalkyl, such as an optionally substituted oxazine.

In a further particular embodiment, $Ar^1$ is an optionally substituted pyridin-4-yl such as a pyridinyl-4-yl, optionally further fused to another ring system selected from an optionally substituted aryl (e.g. phenyl).

In a further particular embodiment, $Ar^1$ is an optionally substituted pyridin-4-yl such as pyridin-4-yl, a pyridin-4-yl substituted by one or more groups selected from optionally substituted $C_1$-$C_6$ alkyl (e.g. methyl, dimethyl), optionally substituted $C_1$-$C_6$ alkoxy (e.g. methoxy, cyclopropyloxy), hydroxyl, optionally substituted amino (e.g. $NH_2$, methyl amino, dimethyl amino), optionally substituted $C_3$-$C_8$ cycloalkyl (e.g. cyclopropyl), and optionally substituted heterocycloalkyl (e.g. optionally substituted morpholinyl, optionally substituted pyperazinyl such as 4-methyl piperazinyl).

In a further particular embodiment, $Ar^1$ is an optionally substituted pyridin-4-yl further fused to an optionally substituted aryl (e.g. phenyl, phenyl optionally substituted by halogen such as fluoro).

In a further particular embodiment, $Ar^1$ is an optionally substituted pyridin-2-yl such as pyridin-2-yl, a pyridin-2-yl substituted by one or more groups selected from optionally substituted $C_1$-$C_6$ alkoxy (e.g. methoxy).

In another embodiment, $Ar^1$ is the following group

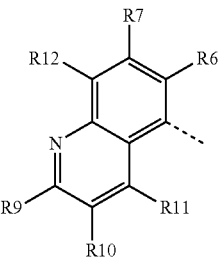

wherein $R^6$, $R^7$, $R^9$, $R^{10}$, $R^1$ and $R^{12}$ are as defined in the detailed description.

In a further particular embodiment $R^6$, $R^7$, $R^9$, $R^{10}$, $R^{11}$ and $R^{12}$ are H.

In another further particular embodiment $R^6$, $R^7$, $R^{10}$, $R^{11}$ and $R^{12}$ are H.

In another further particular embodiment $R^9$ is alkoxy, such as $C_1$-$C_6$ alkoxy (e.g. methoxy) or hydroxyl.

In another particular embodiment, $Ar^1$ is an optionally substituted pyrimidin-5-yl, such as pyrimidin-5-yl.

In another embodiment, $Ar^1$ is selected from the following group

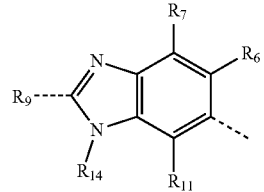

wherein $R^6$, $R^7$, $R^9$, $R^{10}$, $R^{11}$ and $R^{14}$ are as defined in the detailed description.

In a further particular embodiment $R^6$, $R^7$, $R^{10}$, $R^{11}$ and $R^{12}$ are H, and $R^9$ is selected from an optionally substituted $C_1$-$C_6$ alkyl (e.g. methyl).

In a particular embodiment, $Ar^2$ is optionally substituted pyridin-4-yl, such as a pyridin-4-yl, a pyridin-4-yl substituted by one or more groups selected from optionally substituted $C_1$-$C_6$ alkyl (e.g. methyl, dimethyl), optionally substituted $C_1$-$C_6$ alkoxy (e.g. methoxy), $NH_2$, optionally substituted amino (e.g. dimethyl amino, methyl amino, amino), halogen (e.g. fluoro), optionally substituted $C_3$-$C_8$ cycloalkyl (e.g. cyclopropyl), optionally substituted heterocycloalkyl (e.g. optionally substituted morpholinyl, optionally substituted, optionally substituted azetidinyl such as azetidinyl-3-ol, optionally substituted 6-oxa-1-azaspiro[3.3]heptane, optionally substituted 2-oxa-6-azaspiro[3.3]heptane, optionally substituted 7-oxa-2-azaspiro[3.5]nonane, optionally substituted piperidinyl such as 4,4-difluoropiperidin-1-yl, optionally substituted pyrrolidinyl, optionally substituted oxetanyl, optionally substituted piperazinyl, optionally substituted pyrrolidinone, optionally substituted piperidinone, optionally substituted piperazinone and optionally substituted amide.

In another particular embodiment, $Ar^2$ is an optionally substituted pyridin-3-yl, optionally further fused to another ring system selected from an optionally substituted aryl, optionally substituted heteroaryl, optionally substituted $C_3$-$C_8$ cycloalkyl and optionally substituted heterocycloalkyl.

In a further particular embodiment, $Ar^2$ is an optionally substituted pyridin-3-yl such as a pyridin-3-yl, a pyridin-3- yl substituted by one or more groups selected from optionally substituted $C_1-C_6$ alkyl (e.g. methyl, dimethyl, propan-1-ol), optionally substituted heterocycloalkyl $C_1-C_6$ alkyl (e.g. (oxetan-3-yl)methanol, 3-(methoxymethyl)oxetane) optionally substituted $C_1-C_6$ alkoxy (e.g. methoxy), $NH_2$, optionally substituted amino (e.g. dimethyl amino, methyl amino, N-methyl-N-(oxetan-3-ylmethyl)amino), halogen (e.g. chloro, fluoro), optionally substituted $C_3-C_8$ cycloalkyl (e.g. cyclopropyl), optionally substituted heterocycloalkyl (e.g. optionally substituted morpholinyl, optionally substituted thiomorpholine, optionally substituted thiomorpholine 1,1-dioxide, optionally substituted azetidinyl such as azetidinyl-3-ol, 3-methylazetidin-3-ol, azetidin-3-ylmethoxy, (azetidin-3-yl)methanol, 3,3-difluoroazetidin-1-yl, azetidine-3-carboxylic acid, azetidine-3-carboxamide, optionally substituted 6-oxa-1-azaspiro[3.3]heptane, optionally substituted 2-oxa-6-azaspiro[3.3]heptane, optionally substituted 7-oxa-2-azaspiro[3.5]nonane, optionally substituted piperidinyl such as 4,4-difluoropiperidin-1-yl, 2-methoxy-1-(piperidin-1-yl)ethan-1-one, optionally substituted pyrrolidinyl such as 3-methoxypyrrolidin-1-yl, pyrrolidin-2-ylmethanol, pyrrolidin-3-methanesulfonamide, optionally substituted oxetan-3-yl, optionally substituted pyperazinyl such as 4-ethyl piperazinyl, 4-(oxetan-3-yl)piperazin-1-yl, optionally substituted piperazinone such as 1-methylpiperazin-2-one, optionally substituted pyrrolidinone such as 5-(hydroxymethyl)pyrrolidin-2-one), and optionally substituted amide In another further particular embodiment, $Ar^2$ is an optionally substituted pyridin-3-yl, further fused to an optionally substituted heterocycloalkyl (e.g. optionally substituted oxazine forming an optionally substituted bicyclic heteroaryl such as optionally substituted 3,4-dihydro-2H-pyrido[3,2-b][1,4]oxazine, in particular 4-methyl-3,4-dihydro-2H-pyrido[3,2-b][1,4]oxazine, optionally substituted tetrahydrofuran, forming an optionally substituted bicyclic heteroaryl such as optionally substituted furo[3,4-b]pyridine, in particular 1-methyl-5'H-spiro[azetidine-3,7'-furo[3,4-b]pyridine]).

In another particular embodiment, $Ar^2$ is an optionally substituted pyridin-2-yl, optionally further fused to another ring system selected from an optionally substituted aryl, optionally substituted heteroaryl, optionally substituted $C_3-C_8$ cycloalkyl and optionally substituted heterocycloalkyl.

In a further particular embodiment, $Ar^2$ is an optionally substituted an optionally substituted pyridin-2-yl.

In a further particular embodiment, $Ar^2$ is an optionally substituted pyrimidin-4-yl such as pyrimidin-4-yl or a pyrimidin-4-yl substituted by one or more $C_1-C_6$ alkyl (e.g. methyl). In another embodiment, $Ar^2$ is the following group

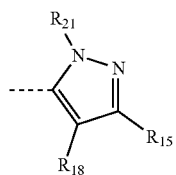

wherein $R^{15}$, $R^{18}$, and $R^{21}$ are as defined in the detailed description.

In a further particular embodiment, $Ar^2$ is an optionally substituted pyrazol-4-yl, such as a pyrazol-4-yl, a pyrazol-4-yl substituted by one or more optionally substituted $C_1-C_6$ alkyl (e.g. methyl).

In another embodiment, $Ar^2$ is selected from the following groups:

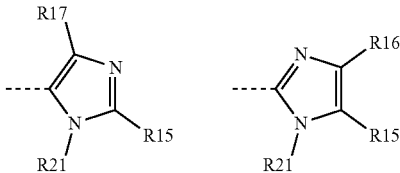

wherein $R^{15}$, $R^{16}$, $R^{17}$, and $R^{21}$ are as defined in the detailed description.

In a particular embodiment, $R^{15}$, $R^{16}$ and $R^{17}$ are H.

In another particular embodiment, $R^{21}$ is an optionally substituted $C_1-C_6$ alkyl (e.g. methyl).

In another embodiment, $Ar^2$ is the following group:

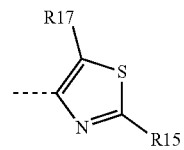

wherein $R^{15}$ and $R^{17}$ are as defined in the detailed description

In another particular embodiment, $R^{15}$ is an optionally substituted $C_1-C_6$ alkyl (e.g. methyl).

In another embodiment, $Ar^2$ is the following group:

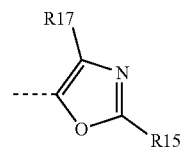

wherein $R^{15}$ and $R^{17}$ are as defined in the detailed description.

In another particular embodiment, $R^{17}$ is H.

In another particular embodiment, $R^{15}$ is H.

In a further particular embodiment, $Ar^2$ is selected from the groups:

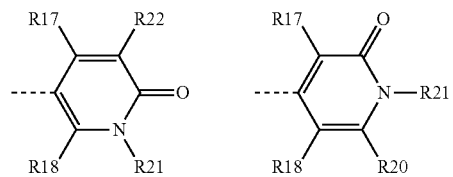

wherein $R^{17}$, $R^{18}$, $R^{20}$, $R^{21}$ and $R^{22}$ are as defined in the detailed description.

In another particular embodiment, $R^{17}$, $R^{18}$, $R^{20}$ and $R^{22}$ are H.

In another particular embodiment, $R^{16}$ is alkoxy (e.g. methoxy).

In another particular embodiment, $R^{16}$ is an optionally substituted $C_1-C_6$ alkyl (e.g. methyl).

In another particular embodiment, $R^{16}$ is an amino (e.g. dimethylamino).

In another particular embodiment, $R^{15}$ or $R^{16}$ is the following group:

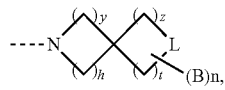

in particular 6-oxa-1-azaspiro[3,3]heptane or 7-oxa-2-azaspiro[3,5]heptane.

In another particular embodiment, $R^{15}$ or $R^{16}$ is the following group

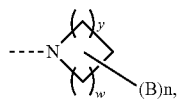

in particular 3-methylazetidine-3-ol, 3,3-difluoroazetidine-1-yl, 2-yl azetidine-3-caeboxamide, 2-yl-azetidin-3-yl, 3-methoxypyrrolidin, pyrrolidin-3yl-methanesulfonamide, pyridine-2-yl pyrrolidin-2yl-methanol, hydroxymethyl pyrrolidinone.

In another particular embodiment, $R^{15}$ is an optionally substituted heterocycloalkyl (e.g. morpholine, optionally substituted piperazinyl such as piperazin-1yl pyridine-3-yl or 4-ethylpiperazinyl, 1-methylpiperazine-2one). In another particular embodiment, $R^{21}$ is optionally substituted $C_1$-$C_6$ alkyl (e.g. methyl, cyclopropyl methyl) or an optionally substituted $C_3$-$C_8$ cycloalkyl $C_1$-$C_6$ alkyl (e.g. cyclopropyl methyl).

In a further particular embodiment, compounds of the present invention include in particular those selected from the following group:

5-(2-methoxypyridin-4-yl)-2-(2-methylpyridin-4-yl)-1H-indole;
2,5-bis(2-methylpyridin-4-yl)-1H-indole;
4-(2-(2-methylpyridin-4-yl)-1H-indol-5-yl)pyridin-2-amine;
5-(5-fluoropyridin-3-yl)-2-(2-methylpyridin-4-yl)-1H-indole;
5-(5-chloropyridin-3-yl)-2-(2-methylpyridin-4-yl)-1H-indole;
5-(5-isopropoxypyridin-3-yl)-2-(2-methylpyridin-4-yl)-1H-indole;
N,N-dimethyl-5-(2-(2-methylpyridin-4-yl)-1H-indol-5-yl)pyridin-3-amine;
5-(6-methylpyridin-3-yl)-2-(2-methylpyridin-4-yl)-1H-indole;
2-(2-methylpyridin-4-yl)-5-(pyrimidin-5-yl)-1H-indole;
2-methyl-5-(2-(2-methylpyridin-4-yl)-1H-indol-5-yl)-1H-benzo[d]imidazole;
2-(2-(azetidin-1-yl)pyridin-4-yl)-5-(5-methoxypyridin-3-yl)-1H-indole;
5-(5-methoxypyridin-3-yl)-2-(2-methoxypyridin-4-yl)-1H-indole;
2-(2,6-dimethylpyridin-4-yl)-5-(5-methoxypyridin-3-yl)-1H-indole;
5-(5-methoxypyridin-3-yl)-2-(2-methylpyrimidin-4-yl)-1H-indole;
5-(5-methoxypyridin-3-yl)-2-(1-methyl-1H-imidazol-5-yl)-1H-indole;
4-(5-(5-methoxypyridin-3-yl)-1H-indol-2-yl)-2-methylthiazole;
2-(2-cyclopropylpyridin-4-yl)-5-(5-methoxypyridin-3-yl)-1H-indole;
1-(4-(5-(5-methoxypyridin-3-yl)-1H-indol-2-yl)pyridin-2-yl)azetidin-3-ol;
1-(4-(5-(5-methoxypyridin-3-yl)-1H-indol-2-yl)pyridin-2-yl)-6-oxa-1-azaspiro[3.3]heptane;
2-(2-(4,4-difluoropiperidin-1-yl)pyridin-4-yl)-5-(5-methoxypyridin-3-yl)-1H-indole;
4-(4-(5-(5-methoxypyridin-3-yl)-1H-indol-2-yl)pyridin-2-yl)morpholine;
2-(5-fluoropyridin-3-yl)-5-(5-methoxypyridin-3-yl)-1H-indole;
5-(5-methoxypyridin-3-yl)-2-(6-methoxypyridin-3-yl)-1H-indole;
4-(5-(5-(5-methoxypyridin-3-yl)-1H-indol-2-yl)pyridin-2-yl)morpholine;
5-(5-methoxypyridin-3-yl)-2-(6-(oxetan-3-yl)pyridin-3-yl)-1H-indole;
1-(5-(5-(5-methoxypyridin-3-yl)-1H-indol-2-yl)pyridin-2-yl)-6-oxa-1-azaspiro[3.3]heptane;
N,N-dimethyl-5-(5-(2-methylpyridin-4-yl)-1H-indol-2-yl)pyridin-2-amine;
4-(5-(5-methoxypyridin-3-yl)-1H-indol-2-yl)-N,N-dimethylpyridin-2-amine;
N,N-dimethyl-4-(5-(quinolin-4-yl)-1H-indol-2-yl)pyridin-2-amine;
1-(5-(6-chloro-5-(5-methoxypyridin-3-yl)-1H-indol-2-yl)pyridin-2-yl)-6-oxa-1-azaspiro[3.3]heptane;
1-(4-(6-chloro-5-(5-methoxypyridin-3-yl)-1H-indol-2-yl)pyridin-2-yl)-6-oxa-1-azaspiro[3.3]heptane;
1-(4-(6-chloro-5-(2-methylpyridin-4-yl)-1H-indol-2-yl)pyridin-2-yl)-6-oxa-1-azaspiro[3.3]heptane;
6-(5-(6-chloro-5-(5-methoxypyridin-3-yl)-1H-indol-2-yl)pyridin-2-yl)-2-oxa-6-azaspiro[3.3]heptane;
2-(5-(6-chloro-5-(5-methoxypyridin-3-yl)-1H-indol-2-yl)pyridin-2-yl)-7-oxa-2-azaspiro[3.5]nonane;
1-(5-(6-chloro-5-(5-methoxypyridin-3-yl)-1H-indol-2-yl)pyridin-2-yl)-3-methylazetidin-3-ol;
6-chloro-2-(6-(3,3-difluoroazetidin-1-yl)pyridin-3-yl)-5-(5-methoxypyridin-3-yl)-1H-indole
1-(5-(6-chloro-5-(5-methoxypyridin-3-yl)-1H-indol-2-yl)pyridin-2-yl)azetidine-3-carboxylic acid;
1-(5-(6-chloro-5-(5-methoxypyridin-3-yl)-1H-indol-2-yl)pyridin-2-yl)azetidine-3-carboxamide;
(1-(5-(6-chloro-5-(5-methoxypyridin-3-yl)-1H-indol-2-yl)pyridin-2-yl)azetidin-3-yl) methanol;
6-chloro-5-(5-methoxypyridin-3-yl)-2-(6-(3-methoxypyrrolidin-1-yl)pyridin-3-yl)-1H-indole;
N-(1-(5-(6-chloro-5-(5-methoxypyridin-3-yl)-1H-indol-2-yl)pyridin-2-yl)pyrrolidin-3-yl) methanesulfonamide;
(1-(5-(6-chloro-5-(5-methoxypyridin-3-yl)-1H-indol-2-yl)pyridin-2-yl)pyrrolidin-2-yl) methanol;
1-(5-(6-chloro-5-(5-methoxypyridin-3-yl)-1H-indol-2-yl)pyridin-2-yl)-5-(hydroxymethyl) pyrrolidin-2-one;
4-(5-(6-chloro-5-(5-methoxypyridin-3-yl)-1H-indol-2-yl)-3-fluoropyridin-2-yl) morpholine;
6-chloro-5-(5-methoxypyridin-3-yl)-2-(6-(4-(oxetan-3-yl)piperazin-1-yl)pyridin-3-yl)-1H-indole;
6-chloro-2-(6-(4-ethylpiperazin-1-yl)pyridin-3-yl)-5-(5-methoxypyridin-3-yl)-1H-indole
4-(5-(6-chloro-5-(5-methoxypyridin-3-yl)-1H-indol-2-yl)pyridin-2-yl)thiomorpholine 1,1-dioxide;
6-chloro-2-(6-(4,4-difluoropiperidin-1-yl)pyridin-3-yl)-5-(5-methoxypyridin-3-yl)-1H-indole;
4-(5-(6-chloro-5-(5-methoxypyridin-3-yl)-1H-indol-2-yl)pyridin-2-yl)-1-methylpiperazin-2-one;

3'-(6-chloro-5-(5-methoxypyridin-3-yl)-1H-indol-2-yl)-1-methyl-5'H-spiro[azetidine-3,7'-furo[3,4-b]pyridine];
7-(6-chloro-5-(5-methoxypyridin-3-yl)-1H-indol-2-yl)-4-methyl-3,4-dihydro-2H-pyrido [3,2-b][1,4]oxazine;
(5-(6-chloro-5-(5-methoxypyridin-3-yl)-1H-indol-2-yl) pyridin-2-yl)(oxetan-3-yl) methanol;
6-chloro-2-(6-(methoxy(oxetan-3-yl)methyl)pyridin-3-yl)-5-(5-methoxypyridin-3-yl)-1H-indole;
2-(5-(6-chloro-5-(5-methoxypyridin-3-yl)-1H-indol-2-yl) pyridin-2-yl)propan-1-ol;
5-(6-chloro-5-(5-methoxypyridin-3-yl)-1H-indol-2-yl)-1-methylpyridin-2(1H)-one;
4-(6-chloro-5-(5-methoxypyridin-3-yl)-1H-indol-2-yl)-1-(cyclopropylmethyl)pyridin-2(1H)-one;
4-(5-(7-chloro-5-(5-methoxypyridin-3-yl)-1H-indol-2-yl) pyridin-2-yl)morpholine;
4-(5-(4,6-difluoro-5-(5-methoxypyridin-3-yl)-1H-indol-2-yl)pyridin-2-yl)morpholine;
4-(5-(6-chloro-5-(quinolin-5-yl)-1H-indol-2-yl)pyridin-2-yl)morpholine;
4-(5-(6-chloro-5-(5-chloropyridin-3-yl)-1H-indol-2-yl)pyridin-2-yl)morpholine;
4-fluoro-5-(5-methoxypyridin-3-yl)-2-(2-methylpyridin-4-yl)-1H-indole;
6-fluoro-5-(5-methoxypyridin-3-yl)-2-(2-methylpyridin-4-yl)-1H-indole;
4-chloro-5-(5-methoxypyridin-3-yl)-2-(2-methylpyridin-4-yl)-1H-indole;
6-chloro-5-(5-methoxypyridin-3-yl)-2-(2-methylpyridin-4-yl)-1H-indole;
5-(5-methoxypyridin-3-yl)-4-methyl-2-(2-methylpyridin-4-yl)-1H-indole;
5-(5-methoxypyridin-3-yl)-6-methyl-2-(2-methylpyridin-4-yl)-1H-indole;
4-methyl-2,5-di(pyridin-4-yl)-1H-indole;
6-methyl-2,5-di(pyridin-4-yl)-1H-indole;
4-(5-(4-chloro-5-(5-methoxypyridin-3-yl)-1H-indol-2-yl) pyridin-2-yl)morpholine;
4-(5-(6-chloro-5-(5-methoxypyridin-3-yl)-1H-indol-2-yl) pyridin-2-yl)morpholine;
4-chloro-2,5-di(pyridin-4-yl)-1H-indole
6-chloro-2,5-di(pyridin-4-yl)-1H-indole;
N,N-dimethyl-4-(2-(2-methylpyridin-4-yl)-1H-indol-5-yl) pyridin-2-amine;
5-(6-cyclopropylpyridin-3-yl)-2-(2-methylpyridin-4-yl)-1H-indole;
5-(6-methoxypyridin-3-yl)-2-(2-methylpyridin-4-yl)-1H-indole;
5-(6-(methoxymethyl)pyridin-3-yl)-2-(2-methylpyridin-4-yl)-1H-indole;
5-(5-ethoxypyridin-3-yl)-2-(2-methylpyridin-4-yl)-1H-indole;
5-(5-cyclopropoxypyridin-3-yl)-2-(2-methylpyridin-4-yl)-1H-indole;
5-(5-(cyclopropylmethoxy)pyridin-3-yl)-2-(2-methylpyridin-4-yl)-1H-indole;
5-(5-cyclopropylpyridin-3-yl)-2-(2-methylpyridin-4-yl)-1H-indole;
7-(2-(2-methylpyridin-4-yl)-1H-indol-5-yl)-3,4-dihydro-2H-pyrido[3,2-b][1,4]oxazine;
3-(2-(2-methylpyridin-4-yl)-1H-indol-5-yl)quinoline;
N-methyl-4-(2-(2-methylpyridin-4-yl)-1H-indol-5-yl)pyridin-2-amine;
4-(4-(2-(2-methylpyridin-4-yl)-1H-indol-5-yl)pyridin-2-yl) morpholine;
5-(6-chloro-2-(6-morpholinopyridin-3-yl)-1H-indol-5-yl) quinolin-2-ol;
4-(5-(6-chloro-5-(thieno[2,3-c]pyridin-4-yl)-1H-indol-2-yl) pyridin-2-yl)morpholine;
4-(5-(6-chloro-5-(6-fluoroquinolin-4-yl)-1H-indol-2-yl) pyridin-2-yl)morpholine;
4-(5-(6-chloro-5-(2-methoxyquinolin-5-yl)-1H-indol-2-yl) pyridin-2-yl)morpholine;
4-(5-(6-fluoroquinolin-4-yl)-1H-indol-2-yl)-N,N-dimethylpyridin-2-amine;
4-(5-(isoquinolin-4-yl)-1H-indol-2-yl)-N,N-dimethylpyridin-2-amine;
N,N-dimethyl-4-(5-(quinolin-5-yl)-1H-indol-2-yl)pyridin-2-amine;
3-chloro-2,5-di(pyridin-4-yl)-1H-indole;
2-(2-methylpyridin-4-yl)-5-(pyridin-4-yl)-1H-indole;
5-(5-methoxypyridin-3-yl)-2-(2-methylpyridin-4-yl)-1H-indole;
5-(5-methoxypyridin-3-yl)-2-(pyridin-4-yl)-1H-indole;
5-(5-methoxypyridin-3-yl)-2-(pyridin-3-yl)-1H-indole;
4-(2-(pyridin-4-yl)-1H-indol-5-yl)quinoline;
4-(2-(pyridin-3-yl)-1H-indol-5-yl)quinoline;
2,5-di(pyridin-4-yl)-1H-indole;
2-(pyridin-3-yl)-5-(pyridin-4-yl)-1H-indole;
2,5-di(pyridin-3-yl)-1H-indole;
2-(1-methyl-1H-pyrazol-5-yl)-5-(pyridin-4-yl)-1H-indole;
5-(2-(4-methylpiperazin-1-yl)pyridin-4-yl)-2-(pyridin-4-yl)-1H-indole;
5-(5-methoxypyridin-3-yl)-2-(pyridin-2-yl)-1H-indole;
5-(5-methoxypyridin-3-yl)-2-(pyrimidin-4-yl)-1H-indole;
2-(3-fluoropyridin-4-yl)-5-(5-methoxypyridin-3-yl)-1H-indole;
1-isopropyl-5-(5-methoxypyridin-3-yl)-2-(2-methylpyridin-4-yl)-1H-indole;
4-(5-(6-chloro-5-(5-methoxypyridin-3-yl)-1-methyl-1H-indol-2-yl)pyridin-2-yl) morpholine;
1-(2-methoxyethyl)-2,5-di(pyridin-4-yl)-1H-indole;
1-(2-methoxyethyl)-5-(5-methoxypyridin-3-yl)-2-(2-methylpyridin-4-yl)-1H-indole;
1-methyl-5-(5-methoxypyridin-3-yl)-2-(2-methylpyridin-4-yl)-1H-indole;
1-ethyl-5-(5-methoxypyridin-3-yl)-2-(2-methylpyridin-4-yl)-1H-indole;
1-(cyclopropylmethyl)-5-(5-methoxypyridin-3-yl)-2-(2-methylpyridin-4-yl)-1H-indole;
1-(benzyl)-5-(5-methoxypyridin-3-yl)-2-(2-methylpyridin-4-yl)-1H-indole;
7-(4-chloro-5-(5-methoxypyridin-3-yl)-1-methyl-1H-indol-2-yl)-4-methyl-3,4-dihydro-2H-pyrido[3,2-b][1,4] oxazine;
7-(6-chloro-5-(5-methoxypyridin-3-yl)-1-methyl-1H-indol-2-yl)-4-methyl-3,4-dihydro-2H-pyrido[3,2-b][1,4] oxazine;
1-cyclopropyl-5-(5-methoxypyridin-3-yl)-2-(2-methylpyridin-4-yl)-1H-indole;
1-methyl-2,5-di(pyridin-4-yl)-1H-indole; and
5-(5-methoxypyridin-3-yl)-2-(3-methylpyridin-4-yl)-1H-indole.

Compositions

The invention provides pharmaceutical or therapeutic agents as compositions and methods for treating a patient, preferably a mammalian patient, and most preferably a human patient who is suffering from a medical disorder, and in particular a disorder mediated by NADPH oxidase, such as a cardiovascular disorder or disease, a respiratory disorder or disease, a disease or disorder affecting the metabolism, a skin disorder, a bone disorder, a neuroinflammatory disorder, a neurodegenerative disorder, a kidney disease, a reproduction disorder, a disease or disorder affecting the eye and/or the lens, a condition affecting the inner ear, an inflammatory disorder or disease, a liver disease, pain, a cancer, a fibrotic disorder, a psychotic disorder, infectious diseases, angiogenesis, angiogenesis-dependent conditions and/or a disease or disorders of the gastrointestinal system.

Pharmaceutical compositions of the invention can contain one or more amino thiadiazole derivative in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. According to one aspect compositions according to the invention are oral compositions.

Compositions of this invention may also be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia.

Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as formulation processing techniques and the like are set out in Part 5 of Part 5 of Remington's *The Science and Practice of Pharmacy*, 22nd Edition, 2012, University of the Sciences in Philadelphia, Lippincott Williams & Wilkins the content of which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate.

Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, transdermally, transtympanically, rectally, transmucosally, topically, via inhalation, via buccal or intranasal administration, or combinations thereof. Parenteral administration includes, but is not limited to, intravenous, intra-arterial, intraperitoneal, subcutaneous, intramuscular, intra-thecal, and intra-articular. The compositions of this invention may also be administered in the form of an implant, which allows slow release of the compositions as well as a slow controlled i.v. infusion. In a particular embodiment, compounds according to the invention are to be administered orally.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination According to one embodiment of the invention, the compounds according to the invention and pharmaceutical formulations thereof can be administered alone or in combination with a co-agent useful in the treatment of a disease.

According to a particular aspect, the compounds according to the invention and pharmaceutical formulations thereof can be administered alone or in combination with a co-agent useful in the treatment of cancer, such as substances used in conventional chemotherapy directed against solid tumors and for control of establishment of metastases or substances used in hormonotherapy or any other molecule that act by triggering programmed cell death, for example a co-agent selected from the category of drugs that stop the synthesis of pre DNA molecule building blocks such as methotrexate (Abitrexate™), fluorouracil (Adrucil™), hydroxyurea (Hydrea™), and mercaptopurine (Purinethol™), for example a co-agent selected from the category of drugs that directly damage the DNA in the nucleus of the cell such as cisplatin (Platinol®) and antibiotics—daunorubicin (Cerubidine™), doxorubicin (Adriamycin™), and etoposide (VePesid™), for example a co-agent selected from the category of drugs that effect the synthesis or breakdown of the mitotic spindles such as Vinblastine (Velban™), Vincristine (Oncovin™) and Pacitaxel (Taxol™).

According to another embodiment of the invention, the compounds according to the invention and pharmaceutical formulations thereof can be administered in combination with agents targeting cell-surface proteins such as gene transfer of cytokine receptor chain and receptor-targeted cytotoxin administration According to another embodiment of the invention, the compounds according to the invention and pharmaceutical formulations thereof can be administered in combination with radiation therapy.

According to another embodiment of the invention, the compounds according to the invention and pharmaceutical formulations thereof can be administered in combination with immune check-point inhibitors (such as at least one PD-1, PD-L1 or CTLA4 inhibitors) or anti-angiogenic inhibitors as described in WO 2019/086579.

According to another embodiment of the invention, the compounds according to the invention and pharmaceutical formulations thereof can be administered in combination with a vaccine, in particular an anti-cancer vaccine such oncolytic or anti-Herpes simplex virus vaccines such as described in Bartlett et al., 2013, *Molecular Cancer* 2, 12:103 (e.g. talimogene laherparepvec (Imlygic)) or in Fukuhara et al., 2016, *Cancer Sci*, 107(10), 1373-1379, adoptive cellular immunotherapy such as described in Perica et al., 2015, *Rambam Maimonides Med J* 6(1), e0004, immune checkpoint inhibitors such as PD-1 inhibitors like those described in Iwai et al., 2017, *Journal of Biomedical Science*, 24:26 or Mishra, 2017, *Future Oncol*. doi: 10.2217/fon-2017-0115 or Soto Chervin et al., 2016, *F1000Research* 2016, 5 (F1000 *Faculty Rev*): 803 (e.g. such as Pembrolizumab (Keytruda™), Nivolumab (Opdivo™), or PD-L1 inhibitors like Atezolizumab (Tecentriq™), Avelumab (Bavencio™), Durvalumab (Imfinzi™) or CTLA-4 inhibitors such as Ipilimumab (Yervoy™) or LAG-3 inhibitors such as Relatlimab. The invention encompasses the administration of a compound according to the invention or of a pharmaceutical formulation thereof, wherein the compound according to the invention or the pharmaceutical formulation thereof is administered to an individual prior to, simultaneously or sequentially with other therapeutic regimens or co-agents useful in the treatment of cancers (e.g. multiple drug regimens), in a therapeutically effective amount. Compounds according to the invention or the pharmaceutical formulations thereof that are administered simultaneously with said co-agents can be administered in the same or different composition(s) and by the same or different route (s) of administration.

In another particular embodiment, compounds of the invention and pharmaceutical formulations thereof can be administered in combination with immune checkpoint inhibitor such as PD1 inhibitor like Pembrolizumab (Keytruda™).

In another particular embodiment, the compounds according to the invention and pharmaceutical formulations thereof can be administered in combination with an Indoleamine 2,3-dioxygenase (IDO) inhibitor such as described in Marshall and Djamgoz, 2018, *Frontiers in Oncology*, doi: 10.3389/fonc.2018.00315. (e.g. such as indoximod or epacadostat).

In another particular embodiment, compounds of the invention and pharmaceutical formulations thereof can be administered in combination with Adoptive T-cell Therapy such as scFv-anti-Her-2 CAR T-cells.

In another particular embodiment, compounds of the invention and pharmaceutical formulations thereof can be administered in combination with other small molecule inhibitors used as targeted therapy such as (but not restricted to) axitinib (anti-VEGF), dabrafenib (anti-BRAF), trametinib (anti-MAPK/ERK), pazopanib (tyrosine kinase inhibitor), abermaciclib (CDK4/6 inhibitor) and entinostat (HDAC inhibitor).

In another particular embodiment, compounds of the invention and pharmaceutical formulations thereof can be administered in combination with agonists of co-stimulatory receptors. These receptors include 4-1BB/CD137 (e.g. Utomilumab), GITR (glucocorticoid-induced TNFR family-related protein) (e.g. MK-4166) and OX40 (e.g. MEDI6383), that promote proliferation and survival of T-cells, CD27 (e.g. Varlilumab), that is involved in long-term immunological memory of T-, B- and NK-cells and CD40 (e.g. CP-870,893), that mediates antigen-presenting cell activation).

In another particular embodiment, compounds of the invention and pharmaceutical formulations thereof can be administered in combination with nanoparticules such as nanoscale coordination polymer (NCP)-based core-shell nanoparticles (e.g. NCP@pyrolipid) such as described in He et al., 2015, *ACS Nano*, 9, 991 or Zn-pyrophosphate (ZnP) nanoparticles loaded with the photosensitizer pyrolipid (e.g. ZnP@pyro) such as described in Duan et al., 2016, *J Am Chem Soc.*, 138(51): 16686-16695).

In another particular embodiment, the compounds and methods of the invention are contemplated for use in the treatment of cancers wherein the administration of a compound according to the invention is typically conducted during or after chemotherapy, hormonotherapy or radiotherapy.

In another particular embodiment, the compounds and methods of the invention are contemplated for use in the treatment of cancers wherein the administration of a compound according to the invention is typically conducted after a regimen of chemotherapy, hormonotherapy or radiotherapy at times where the tumor tissue will be responding to the toxic assault by inducing angiogenesis to recover by the provision of a blood supply and nutrients to the tumor tissue.

In another embodiment, the administration of a compound according to the invention is performed after surgery where solid tumors have been removed as a prophylaxis against metastases.

Patients

In an embodiment, patients according to the invention are patients suffering from a cardiovascular disorder or disease, in particular of hypertension, atherosclerosis and ischemic conditions.

In another embodiment, patients according to the invention are patients suffering from a respiratory disorder or disease.

In another embodiment, patients according to the invention are patients suffering from a disease or disorder affecting the metabolism, in particular diabetic disorders.

In another embodiment, patients according to the invention are patients suffering from a skin disorder.

In another embodiment, patients according to the invention are patients suffering from a bone disorder.

In another embodiment, patients according to the invention are patients suffering from a neuroinflammatory disorder and/or a neurodegenerative disorder, in particular Parkinson's disease.

In another embodiment, patients according to the invention are patients suffering from a kidney disease.

In another embodiment, patients according to the invention are patients suffering from a reproduction disorder.

In another embodiment, patients according to the invention are patients suffering from a disease or disorder affecting the eye and/or the lens and/or a condition affecting the inner ear.

In another embodiment, patients according to the invention are patients suffering from an inflammatory disorder or disease.

In another embodiment, patients according to the invention are patients suffering from a liver disease.

In another embodiment, patients according to the invention are patients suffering from pain, such as inflammatory pain.

In another embodiment, patients according to the invention are patients suffering from a cancer, in particular colon cancer.

In another embodiment, patients according to the invention are patients suffering from a fibrotic disorder, in particular liver fibrosis.

In another embodiment, patients according to the invention are patients suffering from a psychotic disorder.

In another embodiment, patients according to the invention are patients suffering from an infectious disease, in particular a viral lung infection or influenza.

In another embodiment, patients according to the invention are suffering from angiogenesis or an angiogenesis-dependent condition.

In another embodiment, patients according to the invention are patients suffering from allergic disorders.

In another embodiment, patients according to the invention are patients suffering from traumatisms.

In another embodiment, patients according to the invention are patients suffering from septic, hemorrhagic and anaphylactic shock.

In another embodiment, patients according to the invention are patients suffering from a disease or disorders of the gastrointestinal system.

Use According to the Invention

In another embodiment, the invention provides a compound of the invention for use as a medicament.

In another embodiment, the invention provides a use of a compound of the invention, as well as tautomers, geometrical isomers, optically active forms, pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

In another embodiment, the invention provides a compound of the invention, as well as tautomers, geometrical isomers, optically active forms, pharmaceutically acceptable salts and pharmaceutically active derivative thereof for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

In another embodiment, the invention provides a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, fibrotic disorders, psychotic disorders, infectious diseases, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase). The method comprises administering a compound according to Formula (I) in a patient in need thereof.

In another particular embodiment, the compounds and methods of the invention are contemplated for use in the prevention and/or treatment of fibrotic disorders, in particular pulmonary fibrosis (such as idiopathic pulmonary fibrosis), kidney fibrosis, liver fibrosis (such as NASH), corneal fibrosis, skin fibrosis (such as scleroderma) and cancers with a fibrotic stromal component. In another further particular embodiment, the compounds and methods of the invention are contemplated for use in the prevention and/or treatment of lung fibrosis, including but not limiting to, idiopathic pulmonary fibrosis, chronic obstructive lung disease, severe asthma, pulmonary hypertension, systemic sclerosis.

In another further particular embodiment, the compounds and methods of the invention are contemplated for use in the prevention and/or treatment of liver fibrosis, including but not limiting to, non-alcoholic steatohepatitis, alcoholic steatohepatitis, primary biliary cholangitis, primary sclerosing cholangitis, auto-immune hepatitis, viral hepatitis, progressive familial intra-hepatic cholestasis.

In another further particular embodiment, the compounds and methods of the invention are contemplated for use in the prevention and/or treatment of treating kidney fibrosis, including but not limiting to, hypertensive kidney disease, diabetic kidney disease, focal segmental glomerulosclerosis, IgA nephropathy.

In another further particular embodiment, the compounds and methods of the invention are contemplated for use in the prevention and/or treatment of skin fibrosis, including but not limiting to, systemic sclerosis, burn-induced skin fibrosis, trauma-induced skin fibrosis.

In another further particular embodiment, the compounds and methods of the invention are contemplated for use in the prevention and/or treatment of treating corneal fibrosis, including but not limiting to, corneal surgery induced fibrosis, trauma-induced corneal fibrosis, dry eye syndrome, Sjögren's syndrome.

In another further particular embodiment, the compounds and methods of the invention are contemplated for use in the prevention and/or treatment of inflammatory disorders like skin inflammation (including, but not limiting to, psoriasis, atopic dermitis, pruritis), joint inflammation (including, but not limiting to, rheumatoid arthritis, psoriatic arthritis, reactive artithitis, Behcet's disease, ankylosing spondylarthitis, osteoarthritis), liver inflammation (including, but not limiting to, viral hepatitis, autoimmune hepatitis), central nervous system inflammation (including, but not limiting to, multiple sclerosis, Alzheimer's disease, Parkinson's disease, amytrophic lateral sclerosis, Huntington's disease, prion disease, ataxia diseases and other neurodegenerative diseases).

In another further particular embodiment, the compounds and methods of the invention are contemplated for use in the prevention and/or treatment of pain disorders like skin neuropathic pain (including, but not limiting to, diabetic neuropathy, spinal or nerve injury related pain, amputation, drug induced pain, multiple sclerosis, multiple myeloma, shingles, Lyme disease, Herpes Zoster infection, cancer related pain, HIV-related pain, trigeminal neuralgia), inflammatory pain (including, but not limiting to, pelvic pain including endometriosis, fibromyalgia, joint pain associated with inflammatory disorders, burn related pain, trauma-induced pain).

In another further particular embodiment, the compounds and methods of the invention are contemplated for use in the prevention and/or treatment of angiogenic disorders (where angiogenic disorders include, but not limiting to, solid tumors, endometriosis, benign and malignant vascular tumors and proliferative retinopathies).

In another embodiment, the invention provides a method for inhibiting angiogenesis in a patient in need thereof, wherein the method comprises administering an angiogenesis inhibiting dose of a compound of Formula (I) in a patient in need thereof.

In another embodiment, the invention provides a method of inhibiting tumor neovascularization by inhibiting tumor angiogenesis according to the present methods. Similarly, the invention provides a method for inhibiting tumor growth by practicing the angiogenesis-inhibiting methods. In a particular embodiment, the compounds and methods of the invention are contemplated for use in treatment of a tumor tissue of a patient with a tumor, solid tumor, a metastasis, a cancer, a melanoma, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present compounds and methods include, but are not limited to, tumors of the skin, melanoma, lung, pancreas, breast, colon, laryngeal, ovarian, prostate, colorectal, head, neck, testicular, lymphoid, marrow, bone, sarcoma, renal, sweat gland, and the like tissues. Further examples of cancers treated are glioblastomas. According to a particular aspect, the compounds and methods of the invention are contemplated for use in treatment of cancer selected from head and neck cancer, breast cancer, colorectal cancer, melanoma, lung cancer and glioblastoma.

In another particular embodiment, the compounds and methods of the invention are contemplated for use in treatment of an inflamed tissue and the angiogenesis to be inhibited is inflamed tissue angiogenesis where there is neovascularization of inflamed tissue. In this case, the compound and method according to the invention contemplate the inhibition of angiogenesis in arthritic tissues, such as in a patient with chronic articular rheumatism, in immune or non-immune inflamed tissues, in psoriatic tissue and the like.

In embodiments, the invention contemplates inhibition of angiogenesis in a tissue. The extent of angiogenesis in a tissue, and therefore the extent of inhibition achieved by the present methods, can be evaluated by a variety of methods, such as those which are described herein.

According to an embodiment of the invention, the disease or condition is a cancer.

According to an embodiment of the invention, the compound according to the invention is to be administered in combination with a co-agent useful in the treatment of cancer.

According to an embodiment of the invention, the compound according to the invention is to be administered in combination with radiation therapy.

In another embodiment, the invention provides a pharmaceutical composition containing at least one compound of the invention and a pharmaceutically acceptable carrier, diluent or excipient thereof.

The compounds of invention have been named according the IUPAC standards used in the ChemDraw (product version 17.0.0.206).

Compounds according to the present invention comprise a compound according to Formula (I), its tautomers, its geometrical isomers, its optically active forms as enantiomers, diastereomers and its racemate forms, as well as pharmaceutically acceptable salts thereof.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

The invention having been described, the following examples are presented by way of illustration, and not limitation.

Synthesis of Compounds of the Invention:

The novel derivatives according to Formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approaches for obtaining compounds of Formula (I) is depicted in Schemes 1 to 12 below.

Compound of Formula I, Ia, Ib, II and III ($R^{ii}$=H) may be prepared according to Scheme 1 described hereafter, starting from compounds of Formula 1-I:

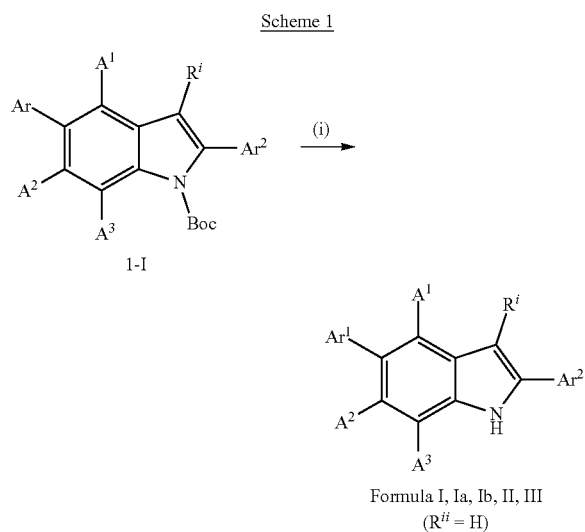

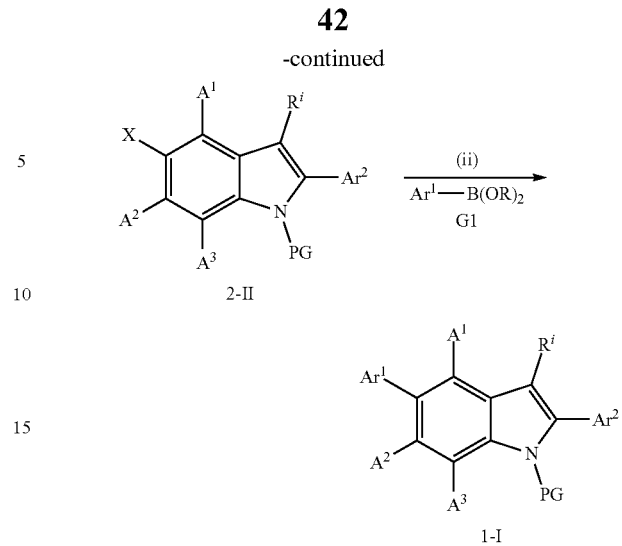

Compounds of Formula 2-I (X=Cl, Br, I) may be protected by a group (PG=Protecting Group) such as t-butyl carbonate group, by reacting with $Boc_2O$ in the presence of a base such as $Et_3N$ or pyridine, in a solvent such as DCM at room temperature, or methyl sulfonyl group, by reacting with methanesulfonyl chloride in the presence of a base such as pyridine in DCM, to provide compounds of Formula 2-II (Step i). A coupling reaction between halo derivatives of Formula 2-II (X=Cl, Br, I) and, for example, a boronic acid or ester $Ar^1$—$B(OR)_2$ of Formula G1 (OR=OH, OMe, pinacolyl) in the presence of a catalyst, such as Pd(dppf) $Cl_2 \cdot CH_2Cl_2$, in the presence of a base such as $Cs_2CO_3$ in a solvent such as dioxane/$H_2O$ at the appropriate temperature may provide compounds of Formula 1-I (Step ii).

Compounds of Formula 2-II may also be prepared according to Scheme 3 described hereafter, starting from compounds of Formula 3-I:

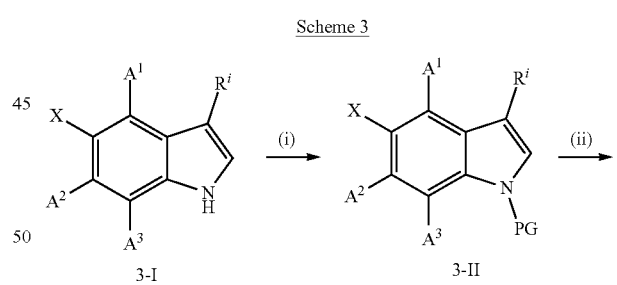

Compounds of Formula 1-I may be treated with a deprotecting agent to release the tert-butoxy carboxylate group using, for example, trifluoroacetic acid, HCl or formic acid, in a solvent such as MeOH, at the appropriate temperature (Step i) to provide Compound of Formula I, Ia, Ib, II and III ($R^2$=H).

Compound of Formula 1-I, may be prepared according to Scheme 2 described hereafter, starting from compounds of Formula 2-I via compounds of Formula 2-II:

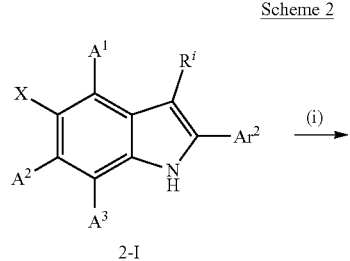

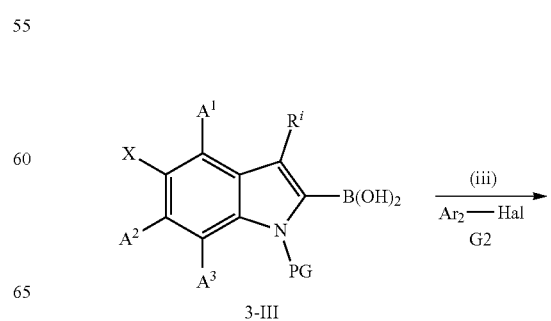

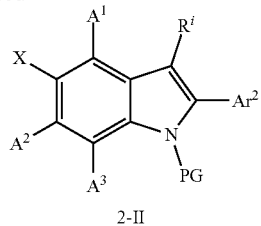

Compounds of Formula 3-I (X=Cl, Br, I) may be commercially available or prepared by the man skilled in the art, such as halogenation of the corresponding substituted indole ($A^1$, $A^2$, $A^3$ and $R^i$ as defined in Formulae I). Compounds of Formula 3-I (X=Cl, Br, I) may be protected by a group (PG=Protecting Group) such as t-butyl carbonate group, by reacting with $Boc_2O$ in the presence of a base such as $Et_3N$ or pyridine, in a solvent such as DCM at room temperature, or methylsulfonyl group, by reacting with methanesulfonyl chloride in the presence of a base such as pyridine in DCM, to provide compounds of Formula 3-II (Step i). Compounds of Formula 3-II may then react with LDA in a solvent such as THF at −78° C., followed by the addition of trimethyl borate, then hydrolysis to afford compounds of Formula 3-III (Step ii). A coupling reaction between compounds of Formula 3-III and, for example, a halide $Ar^2$-Hal (Hal=Cl, Br, I) of Formula G2 in the presence of a catalyst, such as $Pd(dppf)Cl_2 \cdot CH_2Cl_2$, in the presence of a base such as $Cs_2CO_3$ in a solvent such as dioxane/$H_2O$ at the appropriate temperature may provide compounds of Formula 2-II (X=Cl, Br, I) (Step iii).

Alternatively, compounds of Formula 2-II may be prepared according to Scheme 4 described hereafter, starting from compound of Formula 10-I:

Compounds of Formula 10-I (X=Cl, Br, I), commercially available or prepared by the man skilled in the art, may react with carbon tetrabromide and triphenyphosphine, in a solvent such as DCM, at the appropriate temperature (step i) to provide compounds of Formula 10-II. Reduction of the nitro group using $SnCl_2$ in a solvent such as ethanol, at the appropriate temperature, may provide the corresponding amine of Formula 10-III (step ii), which react in turn with methanesulfonyl chloride in the presence of a base such as pyridine, in a solvent such as DCM, to afford sulfonyl amino intermediate of Formula 10-IV (step iii). Intramolecular cyclization using tripotassium phosphate and a catalyst such as copper iodide in a solvent such as toluene, may afford intermediates of Formula 10-V (step iv). A coupling reaction between the bromo derivatives of Formula 10-V, and for example, a boronic acid or ester $Ar^2$—$B(OR)_2$ of Formula G4 (OR=OH, OMe, pinacolyl), in the presence of a catalyst, such as $Pd(dppf)Cl_2 \cdot CH_2Cl_2$, a base such as $Na_2CO_3$ in a solvent such as DME at the appropriate temperature may provide compounds of Formula 2-II (X=Cl, Br, I) (step v).

Compounds of Formula 2-I may be prepared according to Scheme 5 hereafter, starting from compounds of Formula 4-I:

Scheme 5

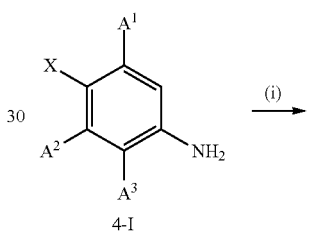

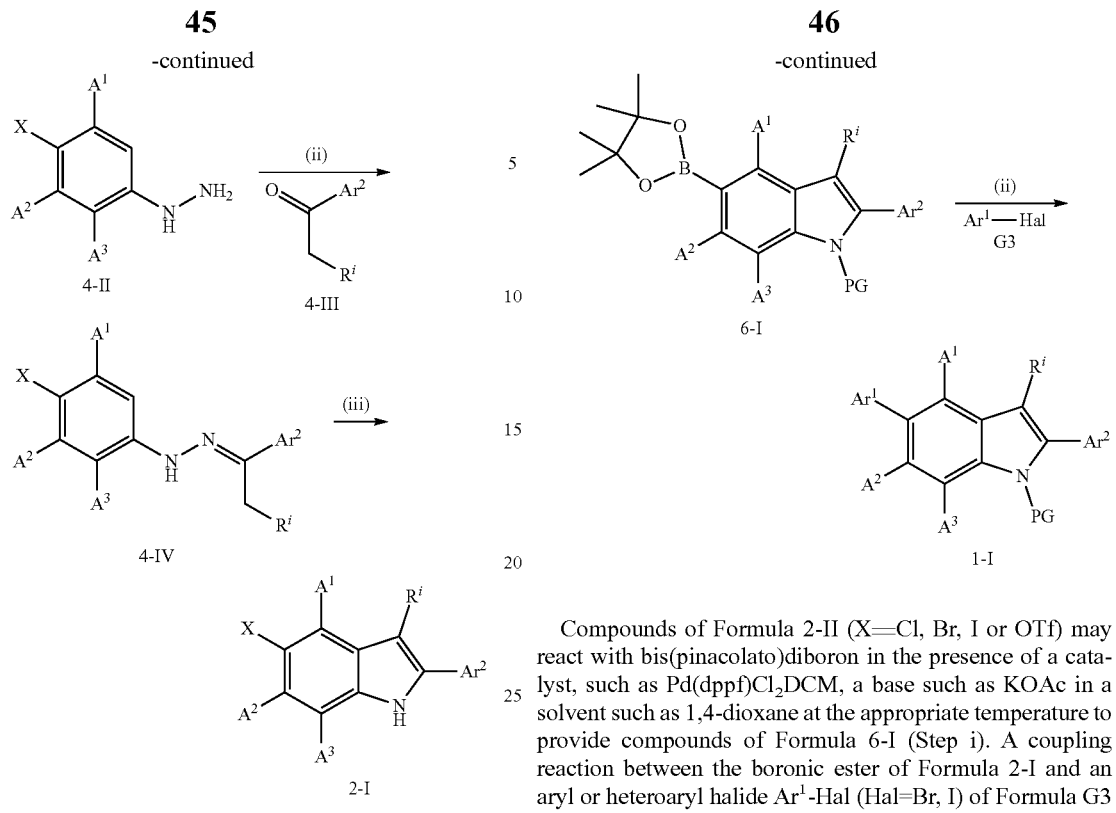

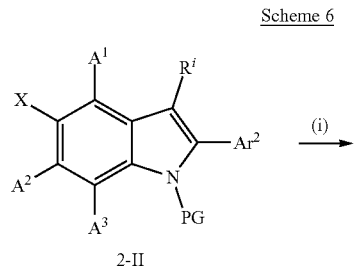

Compounds of Formulae 4-I (X=Cl, Br, I), commercially available or prepared by the man skilled in the art, nay be transformed into hydrazine intermediates of Formula 4-II using aqueous NaNO₂ in HCl, followed by SnCl₂ (Step i). A condensation of compounds of Formula 4-II with ketones of Formulae 4-III, in a solvent such as toluene at the appropriate temperature, provides compounds of Formulae 4-IV (Step ii). Compounds of Formula 4-III may be commercially available or prepared by the man skilled in the art, such as reacting methyl magnesium bromide onto aldehyde Ar²—CHO in a solvent such as THF; or a two-step sequence involving a Stille coupling of an halide Ar²-Hal of Formula G2 (Hal=Cl, Br, I) with tributyl(1-ethoxyvinyl)stannane, in the presence of a catalyst such as Pd(PPh₃)₄, in a solvent such as toluene, at the appropriate temperature, followed by acidic-mediated reaction using formic acid or HCl in a solvent such as MeOH, to release the ketone group (R¹=H). An intramolecular cyclization through, for example, a Fisher indole-type synthesis using, for example, Eaton's reagent at the appropriate temperature, such as 60"C, may provide compounds of Formulae 2-I (Step iii).

Compounds of Formula 1-I may be prepared according to Scheme 6 hereafter, starting from compounds of Formula 2-II, via compounds of Formula 6-I:

Compounds of Formula 2-II (X=Cl, Br, I or OTf) may react with bis(pinacolato)diboron in the presence of a catalyst, such as Pd(dppf)Cl₂·DCM, a base such as KOAc in a solvent such as 1,4-dioxane at the appropriate temperature to provide compounds of Formula 6-I (Step i). A coupling reaction between the boronic ester of Formula 2-I and an aryl or heteroaryl halide Ar¹-Hal (Hal=Br, I) of Formula G3 (Hal=Br, I) in the presence of a catalyst, such as Pd(dppf)Cl₂·DCM, a base such as K₂CO₃ in a solvent such as dioxane/H₂O at the appropriate temperature may provide compounds of Formula 1-I (Step ii).

Compounds of Formula I, Ia, Ib, II and III (R$^{ii}$=H) may be prepared according to Scheme 7 described hereafter, starting from compounds of Formula 2-I:

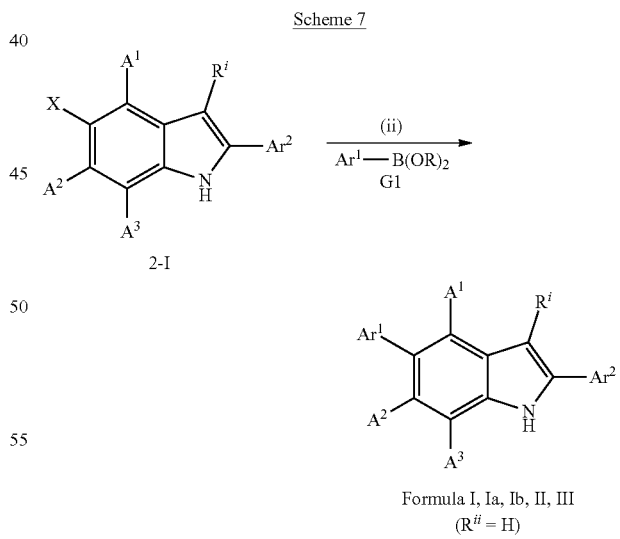

A coupling reaction between compounds of Formula 2-I (X=Cl, Br, I) and, for example, a boronic acid or ester Ar¹—B(OR)₂ of Formula G1 (OR=OH, OMe, pinacolyl) in the presence of a catalyst, such as Pd(dppf)Cl₂·CH₂Cl₂, a base such as Cs₂CO₃ in a solvent such as dioxane/H₂O at the appropriate temperature, may provide compounds of Formula I, Ia, Ib and II (Step i).

Compounds of Formula I and Ia (R$^i$=halide, such as Cl; R$^{ii}$=H) may be prepared according to Scheme 8 hereafter, starting from compounds of Formula 2-I (R$^1$=H):

Scheme 8

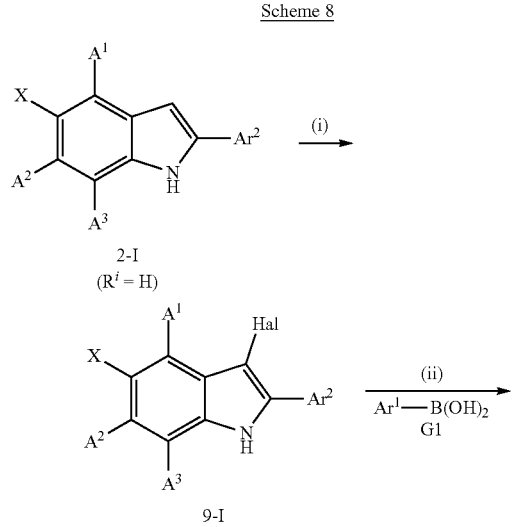

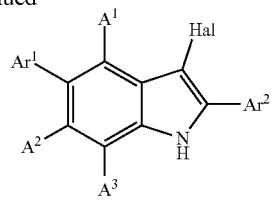

Formula I and Ia

Compounds of Formula 2-I (X=Cl, Br, I; R$^i$=H) may react with a halogenating agent, such as NCS (Hal=Cl), in a solvent such as CCl$_4$ at the appropriate temperature to provide compound of Formula 9-I (Hal=Cl) (Step i), preferably when Hal is Cl or F, X is Br or I. A coupling reaction between the bromo derivatives of Formula 9-I and, for example, a boronic acid or ester Ar$^1$—B(OR)$_2$ of Formula G1 (OR=OH, OMe, pinacolyl) in the presence of a catalyst, such as Pd(dppf)Cl$_2$·CH$_2$Cl$_2$ a base such as Na$_2$CO$_3$ in a solvent such as dioxane/H$_2$O at the appropriate temperature may provide compounds of Formula I and Ia (R$^i$=halide, such as Cl; R$^{ii}$=H) (Step ii).

Compound of Formula I, Ia, Ib, II and III (R$^{ii}$=H) may be prepared according to Scheme 9 described hereafter, starting from compounds of Formula 4-I:

Scheme 9

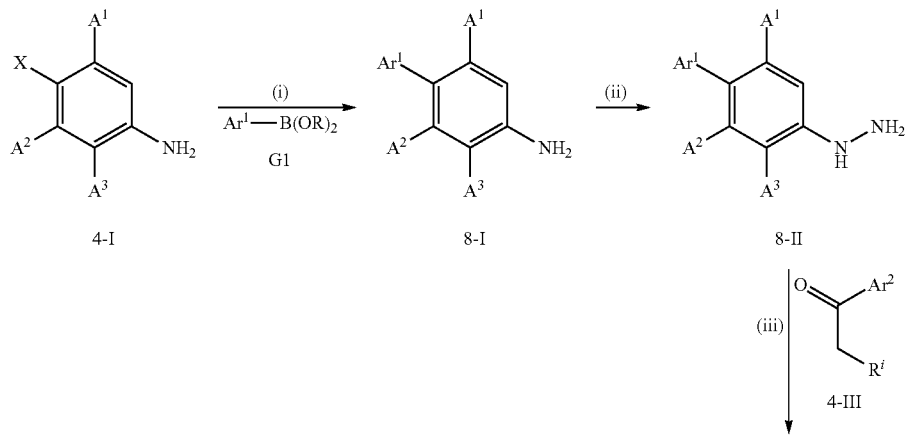

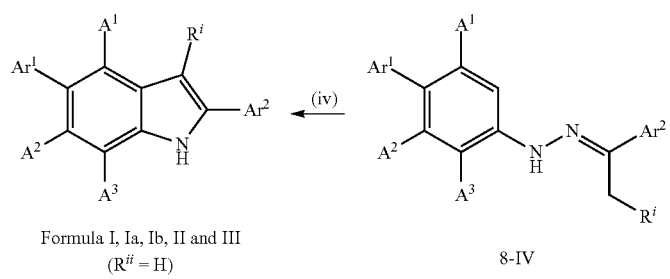

Compounds of Formula 4-I (X=Cl, Br, I or OTf), commercially available or prepared by the man skilled in the art, are engaged in a coupling reaction with, for example, a boronic acid or ester Ar¹—B(OR)₂ of Formula G1 (OR=OH, OMe, pinacolyl) in the presence of a catalyst, such as Pd(dppf)Cl₂, a base such as Na₂CO₃ in a solvent such as dioxane/H₂O at the appropriate temperature may provide compounds of Formula 8-I (Step i). Compounds of Formula 8-II are prepared from the reaction of compounds of Formula 8-I with NaNO₂ in the presence of SnCl₂ in conc. HCl and in H₂O, (Step ii). A condensation of hydrazine intermediates of Formula 8-II with ketones of Formula 4-III, in a solvent such as toluene at the appropriate temperature, such as 80"C, may afford compounds of Formula 8-III (Step iii). An intramolecular cyclization through, for example, a Fisher indole-type synthesis using Eaton's reagent at the appropriate temperature such as 50° C., may provide compound of Formula I, Ia, Ib, II and III ($R^{ii}$=H) (Step iv).

Compound of Formula I, Ia, Ib, II and III ($R^{ii}$=H) ($R^{ii}$ is different from H) may also be prepared according to Scheme 10 described hereafter, starting from compound of Formula I, Ia, Ib, II and III ($R^{ii}$=H).

Scheme 10

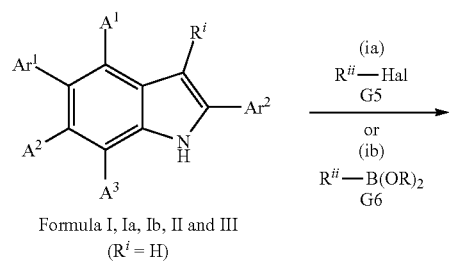

Formula I, Ia, Ib, II and III
($R^i$ = H)

Formula I, Ia, Ib, II and III

Compounds of Formula I, Ia, Ia, Ib, II and III ($R^{ii}$=H) may react with either an alkyl halide $R^{ii}$-Hal of Formula G5 (Hal=F, Cl, Br, I or O-tosyl or O-mesyl) in the presence of a base such as Cs₂CO₃, in a solvent such as ACN, at the appropriate temperature (step 1 a); or an alkyl boronic acid or ester $R^{ii}$—B(OR)₂ of Formula G6 (OR=OH, OMe, pinacolyl) in the presence of Cu(OAc)₂, a base such as Na₂CO₃ in a solvent such as DME at the appropriate temperature (Step ib), to provide compounds of Formula I, Ia, Ib, II and III ($R^{ii}$ is different from H).

Compound of Formula I, Ia Ia, Ib, II and III ($R^{ii}$ is different from H) may be prepared according to Scheme 11 described hereafter, starting from compounds of Formula 2-I:

Scheme 11

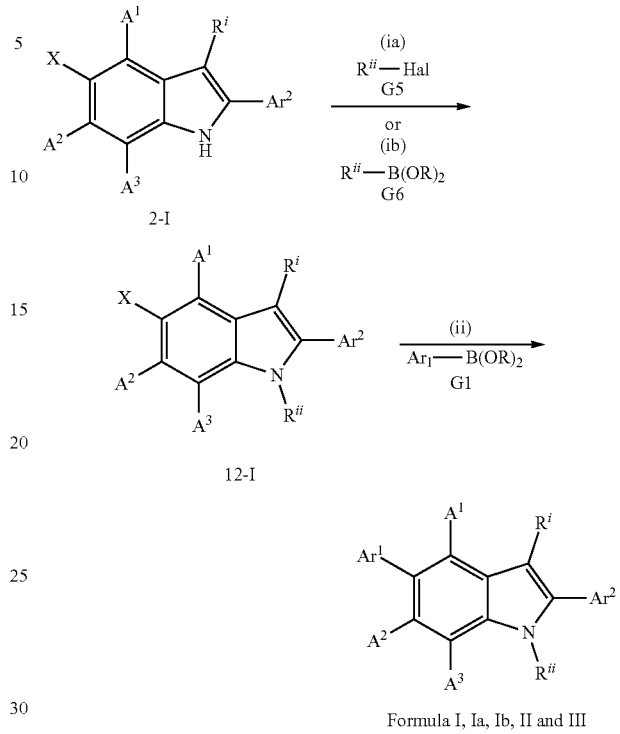

Formula I, Ia, Ib, II and III

Compounds of Formula 2-I (X=Cl, Br, I or OTf) may react with either an alkyl halide $R^{ii}$-Hal of Formula G5 (Hal=F, Cl, Br, I or O-tosyl or O-mesyl) in the presence of a base such as Cs₂CO₃, in a solvent such as dioxane, at the appropriate temperature (step 1 a) or reacting with an alkyl boronic acid or ester $R^{ii}$—B(OR)₂ of Formula G6 (OR=OH, OMe, pinacolyl) in the presence of Cu(OAc)₂, a base such as Na₂CO₃, in a solvent such as DME (Step ib), to provide compounds of Formula 12-I. A coupling reaction between the bromo derivatives of Formula 12-I and, for example, a boronic acid or ester Ar¹—B(OR)₂ of Formula G1 (OR=OH, OMe, pinacolyl) in the presence of a catalyst, such as Pd(dppf)Cl₂, a base such as Na₂CO₃ in a solvent such as dioxane/H₂O at the appropriate temperature may provide compounds of Formula I, Ia, Ib, II and III ($R^{ii}$ is different from H) (Step ii).

Alternatively, compounds of Formula I, Ia, Ib, II and III ($R^{ii}$ is different from H) may also be prepared according to Scheme 12 described hereafter, starting from compound of Formula 13-I:

Scheme 12

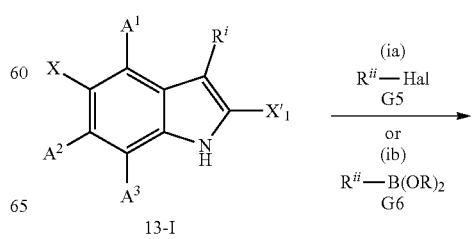

13-I

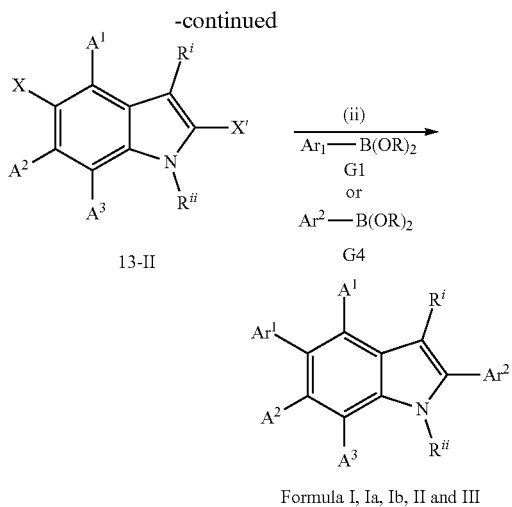

Formula I, Ia, Ib, II and III

Compounds of Formula 13-I (X and X' are each independently selected from Cl, Br, I or OTf) may be commercially available or prepared by the man skilled in the art. Compounds of Formula 13-I may react with either an alkyl halide $R^{ii}$-Hal of Formula G5 (Hal=F, Cl, Br, I or O-tosyl or O-mesyl) in the presence of a base such as NaH, in a solvent such as DMF, at the appropriate temperature (step 1 a) or react with an alkyl boronic acid or ester $R^{ii}$—B(OR)$_2$ of Formula G6 (OR =OH, OMe, pinacolyl) in the presence of Cu(OAc)$_2$, a base such as Na$_2$CO$_3$, in a solvent such as DME at the appropriate temperature (Step ib), to provide compounds of Formula 13-IT. A coupling reaction between the di-bromo derivatives of Formula 13-II and, for example, a boronic acid or ester $Ar^1$—B(OR)$_2$ of Formula G1 or $Ar^2$—B(OR)$_2$ of Formula G4 (OR=OH, OMe, pinacolyl) wherein $Ar^1$ is equal or not to $Ar^2$, in the presence of a catalyst, such as Pd(dppf)Cl$_2$, a base such as Na$_2$CO$_3$ in a solvent such as dioxane/H$_2$O at the appropriate temperature may provide compounds of Formula I, Ia, Ib, II and III ($R^{ii}$ is different from H) (Step ii).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, 2005 and Theodora W. Greene and Peter G. M. Wuts in "*Protective Groups in Organic Synthesis*", Wiley Interscience, 4$^{th}$ Edition 2006.

EXAMPLES

Several methods for preparing the compounds of this invention are illustrated in the following Examples. Unless otherwise noted, all starting materials were obtained from commercial suppliers and used without further purification. Specifically, the following abbreviations may be used in the examples and throughout the specification.

The following abbreviations refer respectively to the definitions below:

ACN (acetonotrinile); AIBN (azobis isobutironitrile); AR (Amplex Red); Bn (benzyl); Boc$_2$O (di-tert-butyl dicarbonate); TBME (tert-butyl methyl ether); (n-Bu)$_3$SnH (tributyl tin); CDCh (deuterated chloroform); DCM or CH$_2$Cl$_2$ (dichloromethane); CH$_3$I (methyl iodide); Cs$_2$CO$_3$ (cesium carbonate); CS$_2$ (carbon disulfur); Cu(OAc)$_2$ (Copper(II) acetate); DMAP (dimethylaminopyridine); DME (dimethylether); DMEM (Dulbecco's Modified Eagle's medium); DMF (dimethylformamide); DMSO (Dimethyl sulfoxide), Dppf (1,1'-bis(diphenylphosphanyl)ferrocene); TEA or Et$_3$N (triethylamine); eq. (equivalent); ESI (Electrospray Ionisation); EtOAc (ethyl acetate); EtOH (ethanol); FAD (Flavin Adenine Dinucleotide); g (grams); $^1$H (proton); H$_2$ (hydrogen); HATU (1-[Bis(dimethylamino)methylene]-1H-1,2,3-triazolo[4,5-b]pyridinium 3-oxid hexafluoro-phosphate); HBSS (Hank's Balanced Salt Solution); HCl (hydrochloric acid); HCOOH (formic acid); HPLC (High Pressure Liquid Chromatography); HRP (horseradish peroxidase); hrs (hours); Hz (Hertz); t-BuOK (potassium tert-butoxide); K$_2$CO$_3$ (potassium carbonate); KF (potassium fluoride); KOAc (potassium acetate); K$_3$PO$_4$ (potassium phosphate); LDA (lithium diisopropylamide); LCMS (Liquid Chromatography Mass Spectrum); M (molar); MeOH (methanol); mg (milligrams); MHz (megahertz); min (minutes); µL (microliters); mL (milliliters); mmol (millimoles); M.p. (melting point); MP (Macroporous); n-BuLi (n-butyl lithium); NaH (sodium hydride); NaHCO$_3$ (sodium hydrogenocarbonate); NaNO$_2$ (sodium nitrite); NaOH (sodium hydroxide); Na$_2$SO$_4$ (sodium sulphate); NCS (N-chlorosuccinimide); NIS (N-iodosuccinimide); NMP (N-Methyl-2-pyrrolidone), NMR (Nuclear Magnetic Reasonance); PA (Phosphatidic Acid); PE (Petroleum ether); PMA (Phorbol 12-myristate 13-acetate); Pd/C (palladium on charcoal); Pd$_2$(dba)$_3$ (palladium (II) dibenzylideneacetone); PdCl$_2$ (dppf)$_2$ (Bis(1,1'-bis(diphenylphosphanyl)-ferrocene palladium (II) dichloride); PdCl$_2$(PPh$_3$)$_2$ (Bis(triphenylphosphine) palladium (II) dichloride); PtO$_2$ (Platinum Oxide); ROS (reactive oxygen species); RT (retention time); SFC (Supercritical Fluid Chromatography); SnCl$_2$ (tin chloride); TFA (trifluoroacetic acid); THF (tetrahydrofuran); TLC (thin layer chromatography); p-TsOH (para-toluene sulfonic acid); Xantphos (4,5-Bis(diphenylphosphino)-9,9-dimethylxanthene).

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

LCMS and HPLC

The High-Performance Liquid Chromatography (HPLC) measurement was performed using a LC pump, a diode-array (DAD) or a UV detector and a column as specified in the respective methods (see tables of methods below). Flow from the column was brought to the Mass Spectrometer (MS) which was configured with an atmospheric pressure ion source. It is within the knowledge of the skilled person to set the tune parameters in order to obtain ions allowing the identification of the compound's nominal monoisotopic molecular weight (MW) and/or exact mass monoisotopic molecular weight. Data acquisition was performed with appropriate software. Compounds are described by their experimental retention times (Rt) and ions. If not specified differently in the tables of data, the reported molecular ion corresponds to the [M+H] (protonated molecule) and/or [M−H] (deprotonated molecule). For molecules with multiple isotopic patterns (Br, Cl), the reported value is the one obtained for the lowest isotope mass. All results were obtained with experimental uncertainties that are commonly associated with the method used. LC-MS were recorded on several apparatus (Micromass ZQ, single quadrapole mass spectrometer). ES MS detector was used, acquiring both in positive and negative ionization modes. Unless otherwise noted, the MS mode was positive electrospray ionization. MS range was 100-1000.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector. The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column. Appropriate focused gradients were selected based on acetonitrile and methanol solvent systems under either acidic or basic conditions. The modifiers used under acidic/basic conditions were formic acid or trifluoroacetic acid (0.1% V/V) and ammonium bicarbonate (10 mM) respectively. The purification was controlled by Waters Fractionlynx software through monitoring at 210-400 nm, and triggered a threshold collection value at 260 nm and, when using the Fractionlynx, the presence of target molecular ion as observed under APi conditions. Collected fractions were analysed by LCMS (Waters Acquity systems with Waters SQD).

Melting Points:

Values are peak values, and are obtained with experimental uncertainties that are commonly associated with this analytical method. For a number of compounds, melting points were determined in open capillary tubes on a YRT-3 apparatus. Melting points were measured with a temperature gradient of 1.5° C./minute. Maximum temperature was 270° C. The melting point was read from a digital display.

Nuclear Magnetic Resonance (NMR):

$^1$H NMR spectra were recorded on a Varian 400 MHz spectrometer. Chemical shifts are expressed in parts per million (ppm, δ units). Splitting patterns describe apparent multiplicities and are designated as s (singlet), d (doublet), t (triplet), q (quadruplet), m (multiplet), br (broad).

In the following, the present invention shall be illustrated by means of some examples, which are not to be viewed as limiting the scope of the invention.

Preparation of Intermediates

Preparation of Hal-Ar$^2$ of Formula G2.A 1-(5-bromopyridin-2-yl)-6-oxa-1-azaspiro[3.3]heptane (G2.A-1)

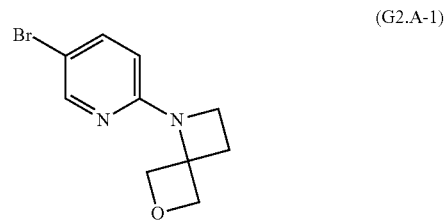 [SMILES: Brc1ccc(N2CCC23COC3)nc1]

(G2.A-1)

A mixture of 5-bromo-2-fluoropyridine (800 mg, 4.55 mmol, 468 uL), 6-oxa-1-azaspiro[3.3]heptane (655 mg, 2.27 mmol), Cs$_2$CO$_3$ (1.48 g, 4.55 mmol) in DMSO (10.0 mL) was degassed and purged with N$_2$ for 3 times, and then the mixture was stirred at 50° C. for 2 hrs under N$_2$ atmosphere. The reaction mixture was partitioned between H$_2$O 10.0 mL and EtOAc (10.0 mL×3). The organic phase was separated, dried over Na$_2$SO$_4$, filtered and concentrated under reduced pressure to give a residue. The residue was purified by prep-TLC (SiO$_2$, PE/EtOAc=5/1) to give intermediate G2.A-1 (353 mg, 30.4% yield) as a yellow solid.

The following halide Hal-Ar$^2$ (G2.A) were prepared according to similar experimental procedure described above, starting from the optionally substituted 2-fluoro-3-bromopyridine or 2-fluoro-4-bromopyridine:
2-(azetidin-1-yl)-4-bromopyridine (G2.A-2);
1-(4-bromopyridin-2-yl)azetidin-3-ol (G2.A-3);
1-(4-bromopyridin-2-yl)-6-oxa-1-azaspiro[3.3]heptane (G2.A-4);
4-bromo-2-(4,4-difluoropiperidin-1-yl)pyridine (G2.A-5);
4-(4-bromopyridin-2-yl)morpholine (G2.A-6);
4-(5-bromopyridin-2-yl)morpholine (G2.A-7);
1-(5-bromopyridin-2-yl)-6-oxa-1-azaspiro[3.3]heptane (G2.A-8);
6-(5-bromopyridin-2-yl)-2-oxa-1-azaspiro[3.3]heptane (G2.A-9);
1-(5-bromopyridin-2-yl)-3-methylazetidin-3-ol (G2.A-10);
2-(3,3-difluoroazetidin-1-yl)-5-bromopyridine (G2.A-11);
1-(5-bromopyridin-2-yl)-4-ethylpiperazine (G2.A-12);
5-bromo-2-(3-methoxypyrrolidin-1-yl)pyridine (G2.A-13);
1-(5-bromopyridin-2-yl)-4-(oxetan-3-yl)piperazine (G2.A-14);
4-(5-bromopyridin-2-yl)-1-methylpiperazin-2-one (G2.A-15);
N-(1-(5-bromopyridin-2-yl)pyrrolidin-3-yl)methanesulfonamide (G2.A-16);
methyl 1-(5-bromopyridin-2-yl)azetidine-3-carboxylate (G2.A-17);
4-(5-bromopyridin-2-yl)thiomorpholine (G2.A-18);
1-(5-bromopyridin-2-yl)azetidine-3-carboxamide (G2.A-19);
4-(3-fluoro-5-bromopyridin-2-yl)morpholine (G2.A-20);
(1-(5-bromopyridin-2-yl)azetidin-3-yl)methanol (G2.A-21);
2-(5-bromopyridin-2-yl)-7-oxa-2-azaspiro[3.5]nonane (G2.A-22);
(1-(5-bromopyridin-2-yl)pyrrolidin-2-yl)methanol (G2.A-23); and 5-bromo-2-(4,4-difluoropiperidin-1-yl)pyridine (G2.A-24).

Preparation of 3-(5-bromopyridin-2-yl)oxetan-3-ol (G2.B)

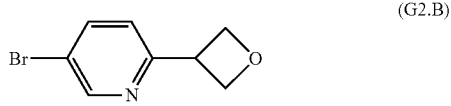 [SMILES: Brc1ccc(C2COC2)nc1]

3-(5-bromopyridin-2-yl)oxetan-3-ol (G2.B1)

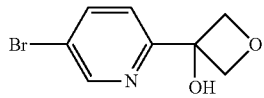

2,5-dibromopyridine (10.0 g, 42.2 mmol) is dissolved in dry toluene (30.0 mL) under a nitrogen atmosphere and cooled to −78° C. n-BuLi (2.5 M, 18.6 mL) is added at −78° C. And the reaction mixture is stirred at −78° C. for 30 minutes. Oxetan-3-one (3.35 g, 46.4 mmol) is added then stirred at −78° C. for 30 minutes. The reaction mixture was quenched by addition NH$_4$Cl 10 mL at 0° C., and extracted with EtOAc (30.0 mL×3). The combined organic layers were, dried over Na$_2$SO$_4$, filtered and concentrated under reduced pressure to give a residue. The residue was purified by column chromatography (SiO$_2$, PE/EtOAc=50/1 to 10/1, 2% TEA) to give compound (G2.B1) (2.94 g, 30.3% yield) as a yellow oil. $^1$H NMR (CDCl$_3$): δ ppm 8.59 (t, J=2.4 Hz, 1H), 7.98-8.01 (m, 1H), 7.89 (d, J=8.4 Hz, 1H), 5.55 (s, 1H), 5.07 (d, J=7.2 Hz, 2H), 4.70 (d, J=7.2 Hz, 2H).

O-(3-(5-bromopyridin-2-yl)oxetan-3-yl) S-methyl carbonodithioate (G2.B2)

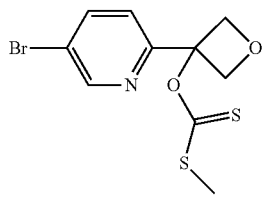 [SMILES: CSC(=S)OC1(c2ccc(Br)cn2)COC1]

To a mixture of intermediate (G2.B1) (2.94 g, 12.8 mmol) in 10.0 mL of THF under 0° C. was added NaH (1.53 g, 38.3 mmol, 60% purity). The mixture was stirred at 25° C. for 2 hrs, followed by in sequence dropwise addition CS$_2$ (973 mg, 12.78 mmol) and CH$_3$I (1.81 g, 12.8 mmol) at 0° C. The resulting mixture was stirred at 0° C. for 30 minutes. The reaction mixture was quenched by addition NH$_4$Cl 10.0 mL at 0° C., and extracted with EtOAc (30.0 mL×3). The combined organic layers were dried over Na$_2$SO$_4$, filtered and concentrated under reduced pressure to give a residue. The residue was purified by column chromatography (SiO$_2$, PE/EtOAc=50/1 to 10:1, 2% TEA) to give intermediate (G2.B2) (2.50 g, 61.1% yield) as a yellow solid. $^1$H NMR (CDCl$_3$): δ ppm 8.75 (d, J=1.6 Hz, 1H), 7.78-7.81 (m, 1H), 7.19 (d, J=8.4 Hz, 1H), 5.08-5.14 (m, 1H), 2.58 (s, 3H).

3-(5-bromopyridin-2-yl)oxetan-3-ol (G2.B)

A mixture of intermediate (G2.B2) (2.50 g, 7.81 mmol), AIBN (128 mg, 781 umol), (n-Bu)$_3$SnH (4.54 g, 15.6 mmol) in toluene (10.0 mL) was degassed and purged with N$_2$ for 3 times, and then the mixture was stirred at 125° C. for 30 mins under N$_2$ atmosphere. The reaction was messy according to TLC. The reaction mixture was quenched by addition aq. KF 30.0 mL at 25° C. and then filtered. The mixture was extracted with EtOAc (20.0 mL×3). The combined organic layers were dried over Na$_2$SO$_4$, filtered and concentrated under reduced pressure to give a residue. The residue was purified by column chromatography (SiO$_2$, PE/EtOAc=50/1 to 20/1) to give intermediate (G2.B) (470 mg, 28.1% yield) as a yellow solid. $^1$HNMR (400 MHz, CDCl$_3$): δ ppm 8.70 (d, J=2.4 Hz, 1H), 7.78-7.81 (m, 1H), 7.18 (d, J=8.0 Hz, 1H), 5.04-5.08 (m, 2H), 4.90 (t, J=12.4 Hz, 2H).

Preparation of tert-butyl 3'-bromo-5'H-spiro[azetidine-3,7'-furo[3,4-b]pyridine]-1-carboxylate (G2.C)

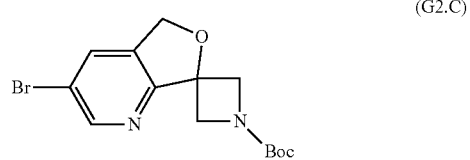 [SMILES: CC(C)(C)OC(=O)N1CC2(C1)OCc1cc(Br)cnc12]

5-bromo-3-(bromomethyl)-2-iodopyridine (G2.C1)

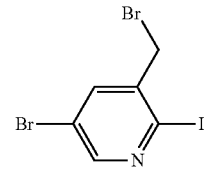

To a stirred solution of 5-bromo-2-iodo-3-methylpyridine (6.90 g, 23.2 mmol) in 1, 2-dichloroethane (10.0 mL) was added NBS (6.18 g, 34.7 mmol) followed by addition of AIBN (1.52 g, 9.26 mmol) at 20° C. in dark. Resulting reaction mixture was heated at 80° C. for 12 hours. The reaction mixture was concentrated under reduced pressure to give a residue. The crude product was purified by chromatography on a silica gel eluted with petroleum ether/ethyl acetate/TEA (from 1/0/0.05 to 20/1/0.05) to give the intermediate (G2.C1) (10.0 g, crude) (6.18 g, 47.0% yield) as a yellow solid. $^1$HNMR (CDCl$_3$): δ ppm 8.36 (d, J=2.0 Hz, 1H), 7.83 (d, J=2.0 Hz, 1H), 4.47 (s, 2H).

(5-bromo-2-iodopyridin-3-yl)methanol (G2.C2)

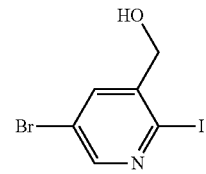

A mixture of intermediate (G2.C1) (4.94 g, 13.1 mmo), CaCO₃ (6.82 g, 68.2 mmol) in dioxane/H₂O (1/1) (30.0 mL) was degassed and purged with N₂ for 3 times, and then the mixture was refluxed at 100° C. for 24 hrs under N₂ atmosphere. The reaction mixture was filtered and the filtrate was concentrated under reduced pressure to give a residue. The residue was purified by column chromatography (SiO₂, Petroleum ether/Ethyl acetate=30/1 to 5/1) to give intermediate (G2.C2) (1.99 g, 48.4% yield) as a white solid. ¹HNMR (DMSO-d⁶): δ ppm 8.42 (d, J=2.4 Hz, 1H), 7.86 (d, J=2.8 Hz, 1H), 4.48 (d, J=11.6 Hz, 1H), 4.38 (d, J=5.6 Hz, 1H).

tert-butyl 3-(5-bromo-3-(hydroxymethyl)pyridin-2-yl)-3-hydroxyazetidine-1-carboxylate (G2.C3)

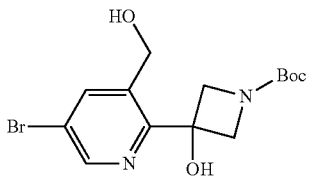 [SMILES: CC(C)(C)OC(=O)N1CC(O)(c2ncc(Br)cc2CO)C1]

To a stirred solution of intermediate (G2.C2) (900 mg, 2.87 mmol) in dry THF (5.00 mL) was added dropwised PrMgCl·LiCl (1.30 M, 5.29 mL) at −60° C. The mixture was stirred at −60° C. for 30 mins. Tert-butyl 3-oxoazetidine-1-carboxylate (589 mg, 3.44 mmol) in dry THF (5.00 mL) was added at −60° C. to above reaction mixture. Resulting reaction mixture was stirred at 20° C. for 2 hours under nitrogen atmosphere. The reaction mixture was quenched by addition H₂O (10.0 mL) at 0° C. and concentrated under reduced pressure to give a residue. The residue was purified by prep-HPLC (column: Phenomenex luna C18 250*50 mm*10 um; mobile phase: [water (0.1% TFA)-ACN]; B %: 20%-50%, 20 min) to give intermediate (G2.C3) (150 mg, 14.6% yield) as a white solid.

tert-butyl 3'-bromo-5'H-spiro[azetidine-3,7'-furo[3,4-b]pyridine]-1-carboxylate (G2.C)

To a stirred solution of intermediate (G2C.3) (300 mg, 835 umol) in dry toluene (3.00 mL) was added TEA (423 mg, 4.18 mmol) at 0° C. followed by addition of p-tolylsulfonyl 4-methylbenzenesulfonate (327 mg, 1.00 mmol). Resulting reaction mixture was stirred at 80° C. for 16 hours under nitrogen atmosphere. The mixture was concentrated under reduced pressure to give a residue, which was purified by prep-TLC (SiO₂, Petroleum ether/Ethyl acetate=5/1) to give intermediate (G2.C) (120 mg, crude) as a yellow oil.

Preparation of 7-bromo-4-methyl-3,4-dihydro-2H-pyrido[3,2-b][1,4]oxazine (G2.D)

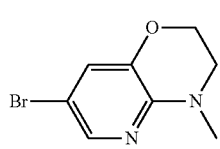

To a solution of 7-bromo-3,4-dihydro-2H-pyrido[3,2-b][1,4]oxazine (1.50 g, 6.98 mmol) in THF (10.0 mL) was added dropwise NaH (307 mg, 7.67 mmol, 60% purity) at 0° C. After addition, the mixture was stirred at 0° C. for 30 mins, and then CH₃I (1.09 g, 7.67 mmol, 478 uL) was added dropwise at 0° C. The resulting mixture was stirred at 0° C. for 30 mins. The reaction mixture was extracted with EtOAc (10.0 mL×3) and H₂O (10.0 mL). The combined organic layers were dried over Na₂SO₄, filtered and concentrated under reduced pressure to give intermediate (G2.D) (1.78 g, crude) as a yellow solid which was without purification Preparation of 4-bromo-1-(cyclopropylmethyl)pyridin-2(1H)-one (G2.E)

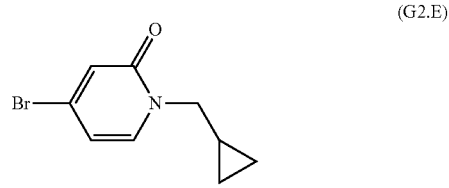 [SMILES: O=c1cc(Br)ccn1CC1CC1]

4-bromopyridin-2(1H)-one (G2.E1)

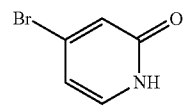

To the solution of 2-chloro-4-bromopyridine (2.00 g, 10.4 mmol) and CH₃COONa (1.71 g, 20.8 mmol) in CH₃COOH (5.00 mL), the mixture was stirred at 145° C. for 5 hours. The mixture was concentrated in vacuum and partitioned between ethyl acetate (5.00 mL) and cold water (5.00 mL). The aqueous layer was extracted with ethyl acetate (5.00 mL×3), the combined organic layers was successively washed with sat. NaHCO₃, brine, dried with Na₂SO₄, filtered and concentrated in vacuum. The residue was without further purification to give intermediate (G2.E1) (1.10 g, crude) as light-yellow solid. ¹HNMR (DMSO-d⁶): δ ppm 11.82 (s, 1H), 7.35-7.29 (m, 1H), 6.64-6.59 (m, 1H), 6.37-6.30 (m, 1H).

4-bromo-1-(cyclopropylmethyl)pyridin-2(1H)-one (G2.E)

To the solution of intermediate (G2.E1) (500 mg, 2.87 mmol) in DMF (2.00 mL) was added 2-bromomethylcyclopropyl (388 mg, 2.87 mmol) and Cs₂CO₃ (1.87 g, 5.75 mmol), the mixture was stirred at 25° C. for 5 hours. The residue was poured into H₂O (5.00 mL) and stirred for 5 mins. The aqueous phase was extracted with ethyl acetate (5.00 mL×3). The combined organic phase was washed with brine (10.0 mL), dried with anhydrous Na₂SO₄, filtered and concentrated in vacuum. The residue was purified by silica gel chromatography (Petroleum ether/Ethyl acetate=30/1 to 1/1) to give intermediate (G2.E) (500 mg) as yellow oil. ¹HNMR (CDCl₃): δ ppm 7.25 (d, J=7.2 Hz, 1H), 6.81 (d, J=2.0 Hz, 1H), 6.33 (dd, J=2.4, 7.2 Hz, 1H), 3.75 (d, J=7.2 Hz, 2H), 1.28-1.14 (m, 1H), 0.65-0.57 (m, 2H), 0.42-0.32 (m, 2H).

Preparation of Intermediate 4-III (Scheme 4 and Scheme 10)

1-(6-morpholinopyridin-3-yl)ethan-1-one (4-III-A)

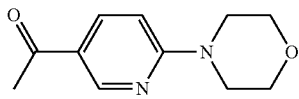

(4-III-A)

To a degassed solution of 4-(5-bromopyridin-2-yl)morpholine (1.30 g, 5.35 mmol) and tributyl(1-ethoxyvinyl)stannane (2.51 g, 6.95 mmol, 2.35 mL) in DMF (10.0 mL) under $N_2$ was added $Pd(PPh_3)_2Cl_2$ (188 mg, 267 umol). The reaction was stirred at 100° C. for 12 hrs. The reaction mixture was diluted with aqueous KF solution (1.40 g of KF in 20.0 mL water). The mixture was stirred for 1 h before being filtered through Celite. The filtrate was extracted with EtOAc (20.0 mL×2), dried over $Na_2SO_4$, concentrated under reduced pressure. The crude material was suspended in THF (20.0 mL) and 4M HCl (2.00 mL) was added. The solution was stirred vigorously for 15 minutes at 25° C. before being concentrated to remove THF, and the residue was dissolved in 15% NaOH 20.0 mL to adjust pH 9. The mixture was extracted with DCM (20.0 ml×3). The combined organics were dried over $Na_2SO_4$, filtered and concentrated under reduced pressure. The residue was purified by column chromatography ($SiO_2$, PE/EtOAc=30/1 to 0/1) to give intermediate (4-III-A) (652 mg, 59.1% yield) as a yellow solid. $^1H$ NMR ($CDCl_3$): δ ppm 8.49 (s, 1H), 8.05 (d, J=11.6 Hz, 1H), 6.61 (d, J=9.2 Hz, 1H), 3.80-3.86 (m, 4H), 3.68 (s, 4H), 2.51 (s, 3H).

Preparation of Substituted Indole Intermediates 5-bromo-2-(2-methylpyridin-4-yl)-1H-indole (U1)

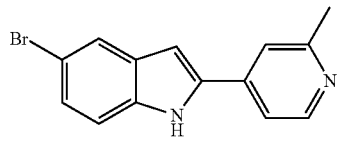

(U1)

(4-bromophenyl)hydrazine (U1.1)

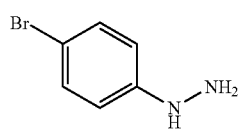

According to Scheme 5, step i: to a solution of 4-bromoaniline (10 g, 58.1 mmol) in HCl (12 M, 150 mL, $H_2O$) was added dropwise a solution of $NaNO_2$ (4.41 g, 64.0 mmol) in $H_2O$ (10 mL) at 0° C. The reaction was stirred at 0° C. for 30 min. Then to the mixture was added dropwise a solution of $SnCl_2 \cdot 2H_2O$ (32.8 g, 145 mmol) in HCl (12 M, 50 mL, $H_2O$) at 0° C. The resulted mixture was stirred at 0° C. for another 4 h. The mixture was filtered and the filtrate cake was washed with 2 N HCl (50 mL). The precipitate was suspended in $H_2O$ (100 mL) and adjusted to pH=9~10 by adding 2 N NaOH and the solution was extracted with EtOAc (70 mL*3), dried over $Na_2SO_4$, filtered and concentrated under reduced pressure to give intermediate (U1.1) (8 g, crude) as an off-white solid, which was used into the next step without further purification.

4-(1-(2-(4-bromophenyl)hydrazineylidene)ethyl)-2-methylpyridine (U1.2)

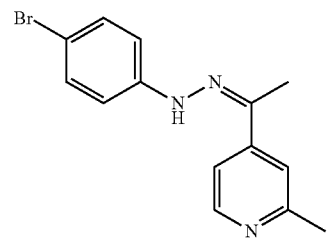 [SMILES: C/C(=N/Nc1ccc(Br)cc1)c1ccnc(C)c1]

According to Scheme 5, Step ii: to a solution of intermediate U1.1 (30 g, 160 mmol) in toluene (210 mL) was added 4-acetyl-2-methylpyridine (26 g, 192 mmol). Then the solution was stirred at 80° C. for 15 hr under $N^2$. The solution was cooled to 10-20° C., then solid precipitated and filtered to give compound (U1.2) (40 g, yield: 82%) as a yellow solid which was used for next step without further purification. $^1$HNMR ($CDCl_3$): δ ppm 8.48 (d, J=5.4 Hz, 1H), 7.62 (s, 1H), 7.49 (s, 1H), 7.44-7.45 (m, 1H), 7.38 (d, J=8.0 Hz, 2H), 7.08 (d, J=8.0 Hz, 2H), 2.60 (s, 3H), 2.20 (s, 3H).

5-bromo-2-(2-methylpyridin-4-yl)-1H-indole (U1)

According to Scheme 5, Step iii: intermediate U1b.2 (20 g, 65.8 mmol) was added to Eaton's reagent (200 mL). Then the solution was stirred at 60° C. for 1.5 hr. The solution was poured into saturated $Na_2CO_3$ (aq) (2 L), then filtered and the solid was dissolved in THF (1 L), dried over $Na_2SO_4$, filtered and concentrated under vacuum to give compound U1 (20 g, yield: 53%) as a yellow solid. The crude product was directly used without further purification. $^1$HNMR (DMSO-$d^6$): δ ppm 11.96 (br s, 1H), 8.50 (d, J=5.2 Hz, 1H), 7.78 (s, 1H), 7.71 (s, 1H), 7.60 (br d, J=4.6 Hz, 1H), 7.40 (d, J=8.6 Hz, 1H), 7.28 (d, J=8.6 Hz, 1H), 7.12 (s, 1H), 2.52 (s, 3H).

tert-butyl 5-bromo-2-(2-methylpyridin-4-yl)-1H-indole-1-carboxylate (U2)

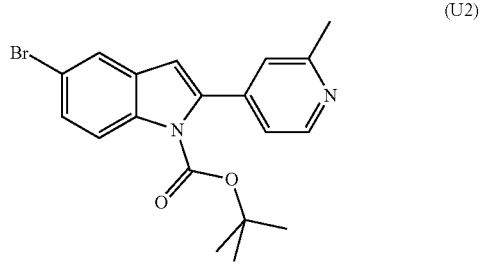 [SMILES: Cc1cc(-c2cc3cc(Br)ccc3n2C(=O)OC(C)(C)C)ccn1]

(U2)

Method 1:

According to Scheme 2, Step i: To a mixture of intermediate U1 (2 g, 6.96 mmol) in THF (30 mL) was added DMAP (170 mg, 1.39 mmol) and (Boc)$_2$O (1.82 g, 8.36 mmol) in one portion at 0° C. The mixture was stirred at 25° C. for 1 hr. The mixture was concentrated under vacuum. The residue was purified by silica gel chromatography (PE:EtOAc=30:1 to 1:1) to give intermediate U2 (1.6 g, yield: 59%, 99% purity) as a white solid.

Method 2:

According to Scheme 3, Step iii: To the solution of intermediate U3 (17.7 g, 52.0 mmol, 1.00 eq) and 4-bromo-2-methylpyridine (14.3 g, 83.3 mmol, 1.60 eq) in DMF (177 mL) was added Na$_2$CO$_3$ (16.5 g, 156 mmol, 3.00 eq) in H$_2$O (60.0 mL). Then Pd(dppf)Cl$_2$·CH$_2$Cl$_2$ (850 mg, 1.04 mmol, 0.02 eq) was added and the solution was stirred at 80° C. for 0.5 h under N$_2$. The solution was poured into 100 mL water and then extracted with EtOAc (30.0 mL×3). The organic layer was washed with brine 30.0 mL, dried over Na$_2$SO$_4$, filtered and concentrated to give the crude product. The residue was purified by column chromatography (SiO$_2$, Petroleum ether/Ethyl acetate=30/1 to 1/1) to obtain intermediate U2 (7.00 g, 18.0 mmol, 34.7% yield) as yellow solid. $^1$HNMR (CDCl$_3$): δ ppm 8.53-8.54 (m, 1H), 8.09 (dd, J=8.8 Hz, 1H), 7.70 (s, 1H), 7.44 (dd, J=9.2 Hz, 1H), 7.20 (s, 1H), 7.14 (d, J=4.8 Hz, 1H), 6.57 (s, 1H), 2.62 (s, 3H), 1.35 (s, 9H).

(5-bromo-1-(tert-butoxycarbonyl)-1H-indol-2-yl)boronic acid (U3)

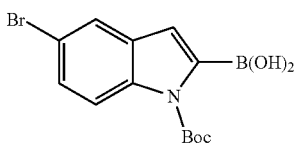

(U3)

According to Scheme 3, step ii: to the solution of tert-butyl 5-bromo-1H-indole-1-carboxylate (2 g, 6.75 mmol) in THF (10 mL) was added triisopropyl borate (2.54 g, 13.5 mmol, 3.11 mL). The solution was cooled to −5° C., LDA (2 M, 5.06 mL) was added. The mixture was stirred at 0° C. for 1 hr. For this example, the same experiment was performed three times. The combined mixture was poured into H$_2$O (100 mL). Then extracted with EtOAc (100 mL×3), the organic phase was combined and concentrated under vacuum. The residue was washed with CH$_3$CN (40 mL). The mixture was filtered, the collected solid was dried under vacuum to give intermediate U3 (5 g, 96% purity, yield: 52%) as a white solid. $^1$HNMR (MeOD): δ ppm HNMR: 400 MHz, MeOD: δ 8.02 (d, J=8.8 Hz, 1H), 7.70 (s, 1H), 7.37-7.40 (m, 1H), 6.60 (s, 1H), 1.67 (s, 9H).

(5-bromo-1-(tert-butoxycarbonyl)-6-chloro-1H-indol-2-yl)boronic acid (U4)

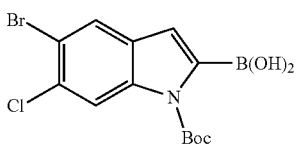

(U4)

tert-butyl 5-bromo-6-chloro-1H-indole-1-carboxylate (U4.1)

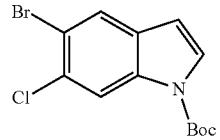

According to Scheme 3, step i: to a solution of 5-bromo-6-chloro-1H-indole (8.00 g, 34.7 mmol) in THF (80.0 mL) was added DMAP (424 mg, 3.47 mmol) and (Boc)$_2$O (15.2 g, 69.4 mmol). The mixture was stirred at 25° C. for 3 hrs. The reaction mixture was quenched by addition HCl (aq) 20.0 mL, and then extracted with EtOAc (200 mL×5). The combined organic layers were dried anhydrous Na$_2$SO$_4$, filtered and concentrated under reduced pressure to give a residue. The residue was purified by column chromatography (SiO$_2$, PE/AcOEt=30/1 to 0/1) to give intermediate (U4.1) (11.4 g, 99.4% yield) as a pink solid. $^1$H NMR (CDCl$_3$) δ ppm 8.31 (s, 1H), 7.79 (d, J=0.8 Hz, 1H), 7.58 (d, J=2.8 Hz, 1H), 6.48 (d, J=3.6 Hz, 1H), 1.68 (s, 9H).

(5-bromo-1-(tert-butoxycarbonyl)-6-chloro-1H-indol-2-yl)boronic acid (U4)

According to Scheme 3, step ii: to a solution of tert-butyl intermediate (U4) (11.4 g, 34.5 mmol) and triisopropyl borate (10.4 g, 55.2 mmol) in THF (80.0 mL) was added dropwise LDA (2.00 M, 34.5 mL) at 0° C. The resulting mixture was stirred at 0° C. for 3 hrs. The reaction mixture was quenched by NH$_4$Cl (aq) (dropwised) 60.0 mL at 0° C., and then extracted with EtOAc (150 mL×3). The combined organic layers were washed with H$_2$O 100 ml, dried anhydrous Na$_2$SO$_4$, filtered and concentrated under reduced pressure to give a residue. The residue was dissolved in TBME 200 mL and stirred at −20° C. Petroleum ether was added slowly until there is no solid precipitation. And the mixture was return to room temperature to give compound (U4) (9.00 g, 69.7% yield) as a yellow solid. $^1$HNMR (CDCl$_3$): δ ppm 8.17 (s, 1H), 7.84 (s, 1H), 7.36 (s, 1H), 1.75 (s, 9H).

5-bromo-1-(tert-butoxycarbonyl)-7-chloro-1H-indol-2-yl)boronic acid (U4a)

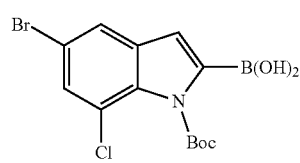

(U4a)

5-bromo-1-(tert-butoxycarbonyl)-7-chloro-1H-indol-2-yl)boronic acid (U4a) was prepared according to the same experimental procedure used to prepare intermediate (U4), starting from 5-bromo-7-chloro-1H-indole. (5-bromo-1-(tert-butoxycarbonyl)-4,6-difluoro-1H-indol-2-yl) boronic acid (U4b)

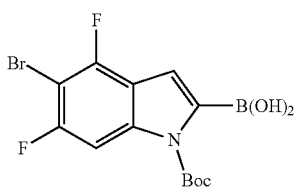

(5-bromo-1-(tert-butoxycarbonyl)-4,6-difluoro-1H-indol-2-yl)boronic acid (U4b) was prepared according to the same experimental procedure used to prepare intermediate (U4), starting from 5-bromo-4,6-difluoro-1H-indole.

(5-bromo-1-(tert-butoxycarbonyl)-4,6-difluoro-1H-indol-2-yl)boronic acid (U5)

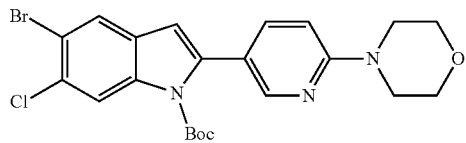

According to Scheme 3, step iii: To a solution of intermediate (U4) (13.0 g, 53.4 mmol), Pd(dppf)Cl$_2$·CH$_2$Cl$_2$ (4.36 g, 5.34 mmol), Cs$_2$CO$_3$ (34.8 g, 107 mmol) in dioxane (360 mL) and H$_2$O (36.0 mL) was added 4-(5-bromopyridin-2-yl)morpholine (24.0 g, 64.1 mmol) at 0° C., then the mixture was stirred at 50° C. for 2 hrs. The mixture was continued to stir for 10 hrs. The reaction mixture was added H$_2$O (150 mL), and then extracted with EtOAc (300 mL×3). The combined organic layers were dried over anhydrous Na$_2$SO$_4$, filtered and concentrated under reduced pressure to give a residue. The residue was purified by column chromatography (SiO$_2$, petroleum ether/EtOAc=30/1 to 0/1) to give intermediate (U5) (15.6 g, 25.4% yield) as yellow solid. $^1$HNMR (CDCl$_3$): δ ppm 8.36 (s, 1H), 8.25 (d, J=2.3 Hz, 1H), 7.78 (s, 1H), 7.53 (dd, J=2.4, 8.7 Hz, 1H), 6.68 (d, J=8.8 Hz, 1H), 6.43 (s, 1H), 3.88-3.82 (m, 4H), 3.60-3.55 (m, 4H), 1.44 (s, 9H).

tert-butyl 6-chloro-2-(6-morpholinopyridin-3-yl)-5-(4,4,5,5-tetramethyl-1,3,2-dioxaborolan-2-yl)-1H-indole-1-carboxylate (U6)

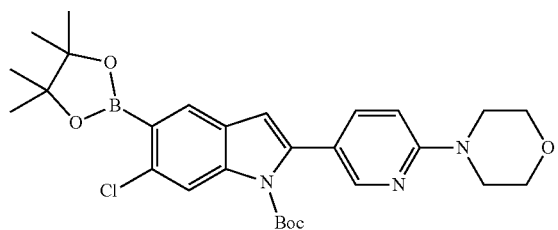

According to Scheme 6, step i: A mixture of intermediate (U5) (830 mg, 1.68 mmol), Bis(pinacolato)diboron (642 mg, 2.53 mmol), KOAc (331 mg, 3.37 mmol), Pd(dppf)Cl$_2$·CH$_2$Cl$_2$ (138 mg, 168 umol) in dioxane (5.00 mL) was degassed and purged with N$_2$ for 3 times, and then the mixture was stirred at 100° C. for 12 hrs under N$_2$ atmosphere. The reaction mixture was quenched by addition H$_2$O 10.0 mL, and then extracted with DCM (20.0 mL×3). The combined organic layers were dried anhydrous Na$_2$SO$_4$, filtered and concentrated under reduced pressure to give a residue. The residue was purified by column chromatography (SiO$_2$, Petroleum ether/Ethyl acetate=50/1 to 0/1) to give compound tert-butyl intermediate (U6) (790 mg, 86.9% yield) as a yellow solid. $^1$HNMR (CDCl$_3$): δ ppm 8.26 (s, 1H), 8.20 (s, 1H), 7.89 (s, 1H), 7.54 (d, J=6.8 Hz, 1H), 7.77 (s, 1H), 6.67 (d, J=8.4 Hz, 1H), 6.46 (s, 1H), 3.84 (d, J=4.4 Hz, 4H), 3.57 (d, J=4.4 Hz, 4H), 1.40 (s, 9H), 1.24 (s, 12H).

tert-butyl 2-(2-methylpyridin-4-yl)-5-(4,4,5,5-tetramethyl-1,3,2-dioxaborolan-2-yl)-1H-indole-1-carboxylate (U7)

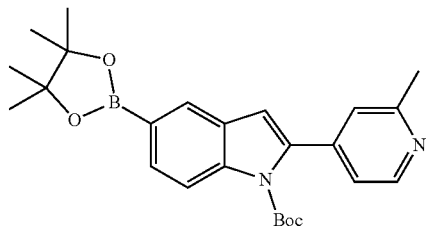

According to Scheme 6, step i: to a mixture of intermediate (U2) (3 g, 7.75 mmol) and Bis(pinacolato)diboron (2.36 g, 9.3 mmol) in 1,4-dioxane (40 mL) was added KOAc (2.4 g, 24.5 mmol) and Pd(dppf)Cl$_2$DCM (1.9 g, 2.32 mmol) in one portion at 25° C. under N$_2$. The mixture was stirred at 80° C. for 2 hr. The mixture was concentrated under vacuum. The residue was purified by silica gel chromatography (PE/AcOEt=20/1 to 1/1) to give intermediate (U7) (3 g, yield: 84%, 94% purity) as yellow oil. $^1$HNMR (CDCl$_3$): δ ppm 8.57 (d, J=3.6 Hz, 1H), 8.22-8.24 (m, 2H), 8.11 (s, 1H), 7.84-7.86 (m, 1H), 7.31 (s, 1H), 7.20-7.22 (m, 1H), 6.69 (d, J=1.6 Hz, 1H), 2.66 (s, 3H), 1.42 (s, 12H), 1.31 (s, 9H).

5-bromo-2-(pyridin-4-yl)-1H-indole (U8)

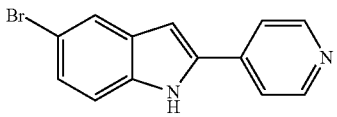

4-(1-(2-(4-bromophenyl)hydrazineylidene)ethyl)pyridine (U8.1)

Similar experimental conditions used for intermediate (U1.2) were applied to prepare 4-(1-(2-(4-bromophenyl)hydrazineylidene)ethyl)pyridine (U8.1), starting from (U1.1) and 4-acetylpyridine, obtained as a yellow solid. $^1$HNMR (CDCl$_3$): δ ppm δ 8.59 (d, J=6.0 Hz, 2H) 7.64-7.61 (m, 3H) 7.39 (d, J=8.8 Hz, 2H) 7.08 (d, J=8.8 Hz, 1H) 2.21 (s, 3H).

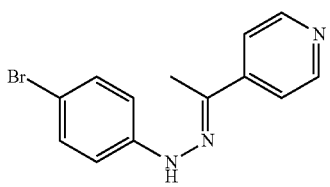 [SMILES: C/C(=N\Nc1ccc(Br)cc1)c1ccncc1]

5-bromo-2-(pyridin-4-yl)-1H-indole (U8)

Similar experimental conditions used for intermediate (U1) were applied to prepare 5-bromo-2-(pyridin-4-yl)-1H-indole (U8,) obtained as a yellow solid.

2,5-dibromo-1-(methylsulfonyl)-1H-indole (U9)

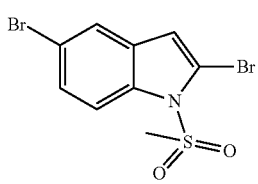

(U9)

4-bromo-2-(2,2-dibromovinyl)-1-nitrobenzene (U9.1)

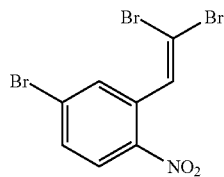

According to Scheme 4, Step i: To a stirred solution of 5-bromo-2-nitrobenzaldehyde (4.2 g, 18.3 mmol, 1 eq.) and carbon tetrabromide (12.1 g, 36.5 mmol, 2 eq.) in DCM (100 mL) at 0° C. was added dropwise a solution of triphenyphosphine (19.1 g, 73 mmol, 4 eq.) in DCM (75 mL) and the resulting mixture stirred at 0° C. for 20 minutes and then at room temperature for 40 minutes. The reaction was passed through a pad of silica and washed through with DCM; the solvent was removed in vacuo and the crude product (U9.1) was used directly in the next reaction.

4-bromo-2-(2,2-dibromovinyl)aniline (U9.2)

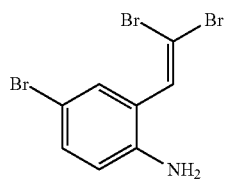

According to Scheme 4, Step ii: To a solution of intermediate (U9.1) (7.06 g, 18.3 mmol, 1 eq.) in EtOH (120 mL) was added tin (II) chloride (17.3 g, 91.3 mmol, 5 eq.) and the resulting mixture heated at 100° C. for 60 minutes. The solvent was removed in vacuo and the residue partitioned between EtOAc (100 mL) and water (100 mL). The aqueous phase was basified to pH 10 using solid potassium carbonate and then extracted with EtOAc (×3). The combined organic phase was washed with water then brine, dried over magnesium sulfate and the solvent removed in vacuo. The residue was purified by silica gel column chromatography using a 10-15% ethyl acetate in iso-hexane gradient to afford intermediate (U9.2) (4.23 g, 65% yield). $^1$HNMR (CDCl$_3$): δ ppm 7.40 (1H, d, J=2.1 Hz), 7.25-7.22 (2H, m), 6.59 (1H, d, J=8.5 Hz), 3.74 (2H, s).

N-(4-bromo-2-(2,2-dibromovinyl)phenyl)methane-sulfonamide (U9.3)

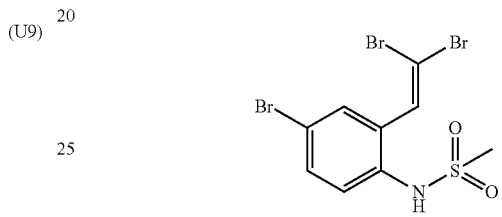

According to Scheme 4, Step iii: To a solution of intermediate (U9.2) (4.2 g, 11.8 mmol, 1 eq.) in dichloromethane (25 mL) and pyridine (1.9 mL, 23.6 mmol, 2 eq.) at 0° C. was added dropwise methanesulfonyl chloride (1.4 mL, 17.7 mmol, 1.5 eq.) and the resulting mixture stirred at room temperature for 16 hours. Dichloromethane (75 mL) was added and the reaction washed with potassium hydrogenosulphate solution (2×25 mL) then sodium hydrogen carbonate solution (50 mL). The organic phase was dried over magnesium sulfate and the solvent removed in vacuo. The residue was purified by silica gel column chromatography using 25% ethyl acetate in iso-hexane to afford intermediate (U9.3) (4.2 g, 82% yield). $^1$HNMR (CDCl$_3$): δ ppm 7.56 (1H, d, J=1.9 Hz), 7.53-7.48 (1H, m), 7.45-7.40 (2H, m), 6.53 (1H, s), 3.06 (3H, s).

2,5-dibromo-1-(methylsulfonyl)-1H-indole (U9)

According to Scheme 4, Step iv: A flask containing a mixture of intermediate (U9.3) (3.3 g, 7.6 mmol, 1 eq.), tripotassium phosphate (3.2 g, 15.2 mmol, 2 eq.) and copper iodide (0.144 g, 0.76 mmol, 0.1 eq.) was degassed by evacuation and purging with nitrogen 3 times. Toluene (50 mL) was added and the mixture degassed by evacuation and purging with nitrogen 3 times then heated to 80° C. for 16 hours. The cooled reaction was partitioned between ethyl acetate (200 mL) and water (50 mL). The organic phase was washed with water (50 mL) then brine (50 mL), dried over magnesium sulfate and the solvent removed in vacuo. The residue was purified by silica gel column chromatography using a 10-20% ethyl acetate in iso-hexane gradient to afford intermediate (U9) (2.4 g, 89% yield). $^1$HNMR (CDCl$_3$): δ ppm 7.96 (1H, d, J=9.0 Hz), 7.65 (1H, d, J=1.9 Hz), 7.41 (1H, dd, J=2.0, 9.0 Hz), 6.79 (1H, s), 3.23 (3H, s).

tert-butyl 5-bromo-2-(2-(dimethylamino)pyridin-4-yl)-1H-indole-1-carboxylate (U10)

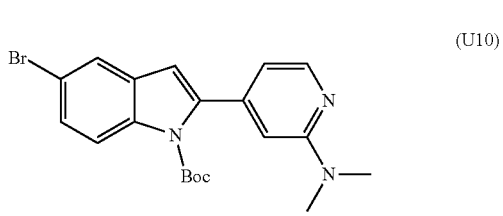 [SMILES: CN(C)c1cc(-c2cc3cc(Br)ccc3n2C(=O)OC(C)(C)C)ccn1]

(U10)

According to Scheme 3, step iii: A mixture of intermediate (U3) (2.03 g, 5.97 mmol), 4-bromo-N,N-dimethylpyridin-2-amine (1.00 g, 4.97 mmol), Pd(dppf)Cl$_2$·CH$_2$Cl$_2$ (406 mg, 497 umol), Cs$_2$CO$_3$ (3.24 g, 9.95 mmol) in dioxane/H$_2$O (10/1) (44.0 mL) was degassed and purged with N$_2$ for 3 times, and then the mixture was stirred at 100° C. for 3 hrs under N$_2$ atmosphere. The reaction mixture was partitioned between H$_2$O 10.0 mL and EtOAc (10.0 mL×3). The organic phase was separated, dried over Na$_2$SO$_4$, filtered and concentrated under reduced pressure to give a residue. The residue was purified by column chromatography (SiO$_2$, PE/EtOAc=40/1 to 5/1) to give intermediate (U10) (600 mg, 29.0% yield) as a yellow solid. $^1$HNMR (CDCl$_3$): δ ppm 8.19 (d, J=4.8 Hz, 1H), 8.08 (d, J=8.8 Hz, 1H), 7.69 (d, J=2.0 Hz, 1H), 7.42-7.45 (m, 1H), 6.55-6.60 (m, 3H), 3.14 (d, J=4.2 Hz, 6H), 1.38 (d, J=4.8 Hz, 9H).

tert-butyl 2-(2-(dimethylamino)pyridin-4-yl)-5-(4,4,5,5-tetramethyl-1,3,2-dioxaborolan-2-yl)-1H-indole-1-carboxylate (U11)

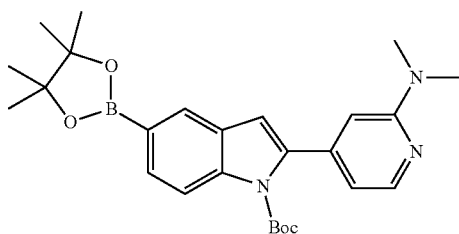

According to Scheme 6, step i: A mixture of intermediate (U10) (298 mg, 716 umol), Bis(pinacolato)diboron (218 mg, 859 umol), Pd(dppf)Cl$_2$·CH$_2$Cl$_2$ (58.5 mg, 71.6 umol), KOAc (141 mg, 1.43 mmol) in dioxane (2.00 mL) was degassed and purged with N$_2$ for 3 times, and then the mixture was stirred at 80° C. for 5 hrs under N$_2$ atmosphere. The reaction mixture was filtered and concentrated under reduced pressure to give a residue. The residue was purified by prep-TLC (SiO$_2$, PE/EtOAc=5/1) to give intermediate (U11) (329 mg, 99.2% yield) as a yellow oil. $^1$H NMR (CDCl$_3$) δ ppm 8.18 (t, J=8.4 Hz, 2H), 8.05 (s, 1H), 7.79 (t, J=9.6 Hz, 1H), 6.58-6.54 (m, 3H), 3.13 (s, 6H), 1.38 (s, 18H), 1.25 (s, 3H).

Example 1: 5-(2-methoxypyridin-4-yl)-2-(2-methylpyridin-4-yl)-1H-indole

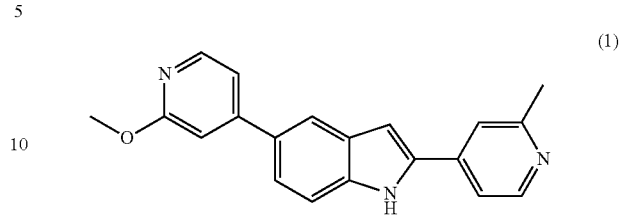

(1)

tert-butyl 5-(2-methoxypyridin-4-yl)-2-(2-methylpyridin-4-yl)-1H-indole-1-carboxylate (1.1)

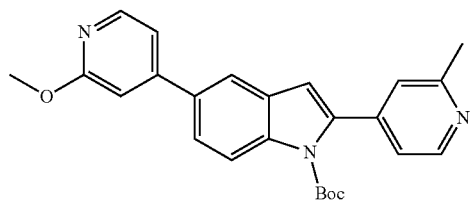

According to Scheme 2, step ii: to a mixture of intermediate (U2) (0.3 g, 775 umol) and (2-methoxypyridin-4-yl)boronic acid (211 mg, 1.55 mmol) in DMF (20 mL) was added the solution of Na$_2$CO$_3$ (246 mg, 2.32 mmol) in H$_2$O (4 mL) and Pd(dppf)Cl$_2$.DCM (190 mg, 232 umol) in one portion at 25° C. under N$_2$. The mixture was stirred at 80° C. for 1 hr. The mixture was concentrated under vacuum. The residue was purified by silica gel chromatography (PE:EtOAC=50:1 to 0:1) to give intermediate (1.1) (0.23 g, yield: 72%, 97% purity) as yellow oil.

Example 1: 5-(2-methoxypyridin-4-yl)-2-(2-methylpyridin-4-yl)-1H-indole

According to Scheme 1, step i: to a mixture of compound (1.1) (0.23 g, 577 umol) in EtOAc (12 mL) was added HCl/EtOAc (4 M, 12 mL) in one portion at 25° C. under N$_2$. The mixture was stirred at 25° C. for 12 hours. The reaction mixture was filtered. The solid was collected to give Example 1 (29.2 mg, yield: 14.8%, 98% purity, HCl salt) as a yellow solid.

$^1$H NMR (MeOD) δ=8.41 (s, 2H), 8.15 (s, 1H), 7.87 (s, 1H), 7.47-7.69 (m, 5H), 7.16 (s, 1H), 3.95 (s, 3H), 2.58 (s, 3H).

The compounds of the invention under Table 1 below were prepared according to similar experimental conditions used above 1, starting from intermediate (U2) reacting with the appropriate Ar$^1$—B(OR)$_z$(Scheme 2, step ii), followed by Boc deprotection (Scheme 1, step i). Compounds C2, C3, C83 and C91 are comparative compounds (not part of the invention):

TABLE 1

| Ex. | Compound | $^1$H NMR (δ ppm) | Ar$^1$—B(OR)$_2$ |
|---|---|---|---|
| C2 | 5-(2,6-dimethylpyridin-4-yl)-2-(2-methylpyridin-4-yl)-1H-indole | (MeOD) δ = 8.64 (d, J = 6.8 Hz, 1H), 8.40 (s, 1H), 8.27 (s, 1H), 8.21 (d, J = 3.2 Hz, 1H), 8.01 (s, 2H), 7.91 (d, J = 8.8 Hz, 1H), 7.73 (d, J = 10.4 Hz, 2H), 2.82 (s, 3H), 2.80 (s, 6H) | |
| C3 | 4-(2-(2-methylpyridin-4-yl)-1H-indol-5-yl)pyridin-2-ol | (D$_2$O) δ = 8.21 (d, J = 6.4 Hz, 1H), 7.58-7.66 (m, 3H), 7.28-7.46 (m,3H), 7.00 (s, 1H), 6.76 (d, J = 6.8 Hz,1H), 6.59 (s,1H), 2.54 (s, 3H). | |
| 4 | 2,5-bis(2-methylpyridin-4-yl)-1H-indole | (D$_2$O) δ = 8.39 (d, J = 7.2 Hz, 1H), 8.27 (d, J = 6.4 Hz, 1H), 8.03 (s, 1H), 7.95-7.96 (m, 2H), 7.79 (d, J = 6.4 Hz, 1H), 7.74 (s, 1H), 7.66 (d, J = 1.6 Hz, 1H), 7.49 (d, J = 8.8 Hz, 1H), 7.29 (s, 1H), 2.68 (s, 3H), 2.56 (s, 3H). | |
| 5 | 4-(2-(2-methylpyridin-4-yl)-1H-indol-5-yl)pyridin-2-amine | (MeOD) δ = 8.61 (d, J = 6.4 Hz, 1H), 8.20-8.27 (m, 3H), 7.67-7.90 (m, 4H), 7.30-7.32 (m, 2H) 2.82 (s, 3H). | |
| 6 | 5-(5-fluoropyridin-3-yl)-2-(2-methylpyridin-4-yl)-1H-indole | (DMSO-d$_6$) δ = 11.93 (s, 1H), 8.83 (s, 1H), 8.82-8.49 (m, 2H), 8.01 (s, 1H), 7.75 (s, 1H), 7.66 (s, 1H), 7.66-7.65 (m, 1H), 7.58-7.56 (m, 2H), 7.23 (s, 1H), 4.05-4.00 (m,1H), 2.51 (d, J = 14.8 Hz, 3H), 1.18-1.15 (m,1H) | |
| 7 | 5-(5-chloropyridin-3-yl)-2-(2-methylpyridin-4-yl)-1H-indole | (MeOD) δ = 8.96 (s, 1H), 8.70 (d, J = 1.6 Hz, 1H), 8.60 (d, J = 6.4 Hz, 1H), 8.53 (s, 1H), 8.23 (d, J = 14.8 Hz, 1H), 8.25 (s, 1H), 8.21 (d,6.4 Hz, 1H), 8.10 (s, 1H), 7.72 (s, 2H), 2.81 (d, J = 9.6 Hz, 1H), 2.81 (s, 3H) | |

TABLE 1-continued

| Ex. | Compound | $^1$H NMR (δ ppm) | Ar$^1$—B(OR)$_2$ |
|---|---|---|---|
| 8 | 5-(5-isopropoxypyridin-3-yl)-2-(2-methylpyridin-4-yl)-1H-indole | (MeOD) δ = 8.79 (s, 1H), 8.57 (s, 1H),8.50-8.45 (m, 2H) 8.26-8.19 (m, 3H), 7.76-7.68 (m, 2H), 5.03 (s, 1H), 2.80 (s, 3H), 1.48 (s, 6H) | |
| 9 | N,N-dimethyl-5-(2-(2-methylpyridin-4-yl)-1H-indol-5-yl)pyridin-3-amine | (D$_2$O) δ = 8.27 (d, J = 6.0 Hz, 1H), 7.88 (s, 1H), 7.73 (d, J = 6.0 Hz, 1H), 7.69 (s, 1H), 7.48 (d, J = 12.8 Hz, 2H), 7.31-7.23 (m, 3H), 7.12 (s, 1H), 2.83 (s, 6H), 2.69 (s, 1H), 2.56 (s, 3H) | |
| 10 | 5-(6-methylpyridin-3-yl)-2-(2-methylpyridin-4-yl)-1H-indole | (MeOD) δ = 9.03 (s, 1H), 9.02-8.82 (m, 1H), 8.80 (d, J = 2.0 Hz, 1H), 8.62 (d, J = 6.4 Hz, 1H), 8.28 (s, 1H), 8.22 (d, J = 6.4 Hz, 1H), 8.17 (s, 1H), 7.98 (d, J = 8.8 Hz, 2H), 7.74-7.69 (m, 1H), 2.84 (s, 3H), 2.82 (s, 3H) | |
| 11 | 2-(2-methylpyridin-4-yl)-5-(pyrimidin-5-yl)-1H-indole | (D$_2$O) δ = 8.69-8.72 (m, 3H), 8.06 (d, J = 6.4 Hz, 1H), 7.51 (d, J = 5.6 Hz, 1H), 7.42 (d, J = 6.4 Hz, 2H), 7.20-7.25 (m, 2H), 6.89 (s, 1H), 2.69 (s, 1H), 2.42 (s, 3H) | |
| 12 | 2-methyl-5-(2-(2-methyl-pyridin-4-yl)-1H-indol-5-yl)-1H-benzo[d]imidazole | (MeOD) δ = 7.93 (d, J = 6.4 Hz,1H), 7.38-7.50 (m, 3H), 7.14-7.30 (m, 5H), 6.86 (s, 1H), 2.49 (s, 3H), 2.26 (s, 3H) | |

Example 13: 2-(2-(azetidin-1-yl)pyridin-4-yl)-5-(5-methoxypyridin-3-yl)-1H-indole

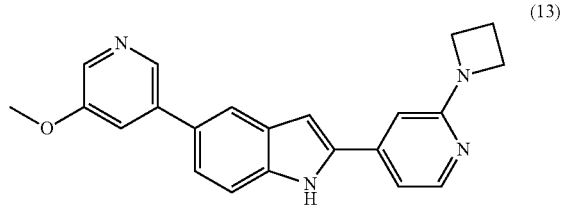 [SMILES: COc1cncc(-c2ccc3[nH]c(-c4ccnc(N5CCC5)c4)cc3c2)c1]

(13)

tert-butyl 2-(2-(azetidin-1-yl)pyridin-4-yl)-5-bromo-1H-indole-1-carboxylate (13.1)

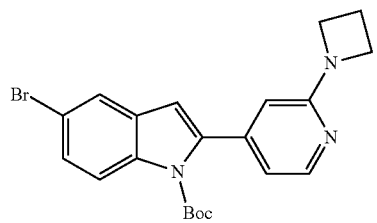 [SMILES: CC(C)(C)OC(=O)n1c(-c2ccnc(N3CCC3)c2)cc2cc(Br)ccc21]

According to Scheme 3, Step iii: A mixture of intermediate (U3) (276 mg, 1.29 mmol), intermediate (G2.A₂) (400 mg, 1.18 mmol), Cs₂CO₃ (1.15 g, 3.53 mmol), Pd(dppf)Cl₂·CH₂Cl₂ (48.0 mg, 58.8 umol) in dioxane/H₂O (10/1) (1.00 mL) and dioxane/H₂O (10/1) (5.00 mL) was degassed and purged with N₂ for 3 times and then the mixture was stirred at 120° C. for 2 hrs under N₂ atmosphere. The reaction mixture was filtered and concentrated under reduced pressure to give a residue. The residue was purified by prep-TLC (SiO₂, PE/EtOAc=0/1) to give compound (13.1) (196 mg, 38.9% yield) as a yellow solid.

tert-butyl 2-(2-(azetidin-1-yl)pyridin-4-yl)-5-(5-bromopyridin-3-yl)-1H-indole-1-carboxylate (13.2)

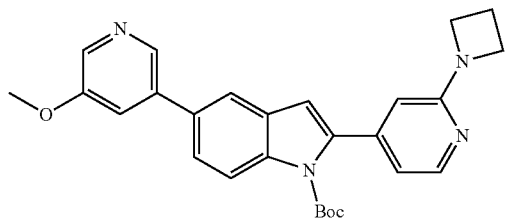 [SMILES: COc1cncc(-c2ccc3c(c2)cc(-c2ccnc(N4CCC4)c2)n3C(=O)OC(C)(C)C)c1]

According to Scheme 2, Step ii: A mixture of compound (13.1) (196 mg, 458 umol), 5-methoxy-pyridyl-3-yl-boronic acid (70.0 mg, 457.6 umol), Cs₂CO₃ (447 mg, 1.37 mmol), Pd(dppf)Cl₂·CH₂Cl₂ (18.7 mg, 22.9 umol) in dioxane/H₂O (10/1) (5.00 mL) was degassed and purged with N₂ for 3 times, and then the mixture was stirred at 120° C. for 5 hrs under N₂ atmosphere. The reaction mixture was filtered and concentrated under reduced pressure to give a residue. The residue was purified by prep-TLC (SiO₂, PE/EtOAc=1/1) to give compound 13.2) (130 mg, 62.2% yield) as a yellow oil. ¹HNMR (CDCl₃): δ ppm=8.53 (t, J=9.2 Hz, 1H), 8.28 (t, J=12.8 Hz, 1H), 8.18 (d, J=5.2 Hz, 1H), 7.77 (s, 1H), 7.56-7.58 (m, 1H), 7.44 (t, J=4.8 Hz, 1H), 6.65-6.69 (m, 2H), 6.34 (s, 1H), 4.09 (t, J=4.8 Hz, 4H), 3.93 (d, J=12.4 Hz, 3H), 2.39-2.47 (m, 2H), 1.42 (m, 9H).

Example 13: 2-(2-(azetidin-1-yl)pyridin-4-yl)-5-(5-methoxypyridin-3-yl)-1H-indole According to Scheme 1, Step i: A mixture of compound (13.2) (130 mg, 285 umol) in HCl/MeOH (4.00 M, 5.00 mL) was degassed and purged with N₂ for 3 times, and then the mixture was stirred at 50° C. for 3 hrs under N₂ atmosphere. The reaction mixture was concentrated under reduced pressure to give a residue. The residue was dissolved and adjusted pH to 8~9 with 5M Na₂CO₃. The mixture was stirred at 30° C. for 30 mins and solid precipitated. The reaction mixture was extracted with EtOAc (5.00 mL×4). The organic phase was separated, dried over Na₂SO₄, filtered and concentrated under reduced pressure to give a residue. The residue was purified by prep-HPLC (column: Xtimate C18 150*25 mm*5 um; mobile phase: [water (10 mM NH₄HCO₃)-ACN]; B %: 40%-70%, 10.5 mins) to give Example 13 (26.4 mg, 26.0% yield, 100% purity) as a yellow solid. ¹H NMR (CDCl₃) δ ppm=8.65 (s, 1H), 8.53 (d, J=2 Hz, 2H), 8.28 (d, J=2.4 Hz, 1H), 8.21 (d, J=5.6 Hz, 1H), 7.85 (s, 1H), 7.47-7.53 (m, 1H), 7.44 (t, J=2 Hz, 2H), 7.02 (s, 1H), 6.88 (d, J=5.6 Hz, 1H), 6.49 (s, 1H), 4.74 (s, 1H), 4.13 (t, J=14.8 Hz, 4H), 3.95 (s, 3H), 7.25-2.28 (m, 2H). The compounds of the invention under Table 2 were prepared according to similar experimental conditions used above, starting from intermediate (U3) reacting with halide of Formula Hal-Ar² (G2.A) (Scheme 3, step iii), followed by coupling with 3-methoxy-pyridyl-5-yl-boronic acid (Scheme 2, step ii) and final Boc deprotection (Scheme 1, step i):

TABLE 2

| Ex. | Compound | ¹H NMR (δ ppm) | (G2.A) Ar²—Hal |
| --- | --- | --- | --- |
| 14 | 5-(5-methoxypyridin-3-yl)-2-(2-methoxypyridin-4-yl)-1H-indole | (MeOD) δ = 8.74 (s, 1H), 8.46 (s, 1H), 8.45 (s, 1H), 8.18 (d, J = 6.0 Hz, 1H), 8.07 (s, 1H), 7.63 (s,2H), 7.49 (d,J = 6.0 Hz,1H), 7.27-7.34 (m, 2H), 4.11 (s,3H), 3.31 (s, 3H) | |

TABLE 2-continued

| Ex. | Compound | ¹H NMR (δ ppm) | (G2.A) Ar²—Hal |
|---|---|---|---|
| 15 | 2-(2,6-dimethylpyridin-4-yl)-5-(5-methoxypyridin-3-yl)-1H-indole | (MeOD) δ = 8.83 (s, 1H), 8.50-8.82 (m, 2H), 8.21 (s, 1H), 8.08 (s, 2H), 7.67-7.78 (m, 3H), 4.51 (s, 3H), 2.78 (s, 6H) | |
| 16 | 5-(5-methoxypyridin-3-yl)-2-(2-methylpyrimidin-4-yl)-1H-indole | (DMSO-$d_6$) δ = 8.71 (d, J = 5.2 Hz, 1H), 8.51 (s, 1H), 8.24 (d, J = 2 Hz, 1H), 7.99 (s, 1H), 7.87 (d, J = 4.8 Hz, 1H), 7.57-7.63 (m, 3H) 7.46 (s, 1H), 3.92 (s, 3H), 2.70 (s, 3H) | |
| 17 | 5-(5-methoxypyridin-3-yl)-2-(1-methyl-1H-imidazol-5-yl)-1H-indole | (MeOD) δ = 9.08 (s, 1H), 8.79 (s, 1H), 8.45-8.51 (s, 2H), 8.17 (s, 1H), 7.89 (s, 1H), 7.67-7.73 (m, 2H), 7.11 (s, 1H), 4.14 (s, 3H), 4.12 (s, 3H) | |
| 18 | 4-(5-(5-methoxypyridin-3-yl)-1H-indol-2-yl)-2-methylthiazole | (DMSO-$d_6$) δ = 8.49 (s, 1H), 8.22 (s, 1H), 7.88 (d, J = 14.8 Hz, 2H), 7.61 (s, 1H), 7.46-7.51 (m, 2H), 6.92 (s, 1H), 3.92 (s, 3H), 2.74 (s, 3H) | |
| 19 | 2-(2-cyclopropylpyridin-4-yl)-5-(5-methoxypyridin-3-yl)-1H-indole | (DMSO-$d_6$) δ = 8.51 (d, J = 2 Hz, 2H), 8.44 (d, J = 5.2 Hz, 1H), 8.24 (d, J = 2.8 Hz, 1H), 7.96 (s, 1H), 7.76 (s, 1H), 7.63 (d, J = 2.8 Hz, 1H), 7.59 (t, J = 5.2 Hz, 1H), 7.56 (d, J = 11.6 Hz, 2H), 7.24 (d, J = 2 Hz, 1H), 3.93 (s, 3H), 2.13-2.18 (m, 1H) 0.99 (t, J = 8.4 Hz, 4H) | |
| 20 | | (CDCl₃) δ = 11.79 (s, 1H), 8.50 (s, 1H), 8.24 (s, 1H), 8.09 (d, J = 4.8 Hz, 2H), 7.93 (s, 1H), 7.62 (s, 1H), 7.53 (s, 2H), 7.12 (t, J = 18.4 Hz, 2H), 6.86 (s, 1H), 5.67 (s, 1H), 4.61 (s, 1H), 4.22 (t, J = 14.4 Hz, 2H), 3.92 (s, 3H), 3.73-3.76 (m, 2H) | |
| | | | (G2.A-3) |

TABLE 2-continued

| Ex. | Compound | ¹H NMR (δ ppm) | (G2.A) Ar²—Hal |
|---|---|---|---|
| | 1-(4-(5-(5-methoxypyridin-3-yl)-1H-indol-2-yl)pyridin-2-yl)azetidin-3-ol | | |
| 21 | 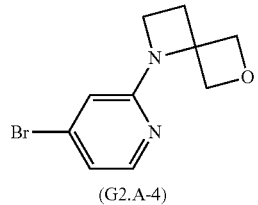 [SMILES: Brc1ccnc(N2CCC23COC3)c1]<br>1-(4-(5-(5-methoxypyridin-3-yl)-1H-indol-2-yl)pyridin-2-yl)-6-oxa-1-azaspiro[3.3] heptane | (DMSO-d₆) δ = 8.50 (d, J = 1.6 Hz, 1H), 8.23 (d, J = 2.4 Hz, 1H), 8.19 (d, J = 5.2 Hz, 1H), 7.95 (s, 1H), 7.62 (s,1H), 7.54 (s, 2H), 7.15 (d, J = 5.6 Hz, 2H), 6.89 (s, 1H), 5.37 (d, J = 6.8 Hz, 2H), 4.58 (d, J = 6.8 Hz, 2H), 3.92 (s, 3H), 3.84 (t, J = 13.6 Hz, 2H), 2.62 (t, J = 14 Hz, 2H) | (G2.A-4) |
| 22 | 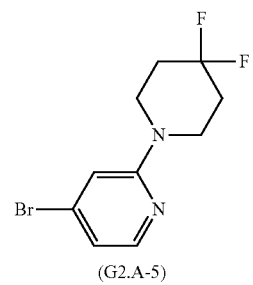 [SMILES: FC1(F)CCN(c2cc(Br)ccn2)CC1]<br>(2-(4,4-difluoropiperidin-1-yl)pyridin-4-yl)-5-(5-methoxy-pyridin-3-yl)-1H-indole | (CDCl₃) δ = 8.63 (s, 1H), 8.54 (s, 1H), 8.26-8.30 (m, 2H), 7.85 (s,1H), 7.44-7.53 (m, 3H), 7.03 (s, 1H), 6.95 (t, J = 10 Hz, 2H), 3.95 (s, 3H), 3.83 (t, J = 10.8 Hz, 4H), 2.01-2.12 (m, 4H) | (G2.A-5) |
| 23 | 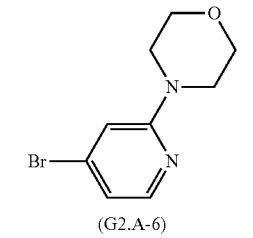 [SMILES: Brc1ccnc(N2CCOCC2)c1]<br>2-(2-(4,4-difluoropiperidin-1-yl)pyridin-4-yl)-5-(5-methoxy-pyridin-3-yl)-1H-indole | (DMSO-d₆) δ = 8.51 (s, 1H), 8.23 (d, J = 2.8 Hz, 1H), 8.17 (d, J = 5.2 Hz, 1H), 7.94 (s, 1H), 7.62 (s, 1H), 7.54 (s, 2H), 7.30 (s, 1H), 7.19 (t, J = 13.2 Hz, 2H), 3.92 (s, 3H), 3.75 (t, J = 9.2 Hz, 4H), 3.55 (d, J = 4.8 Hz, 4H) | (G2.A-6) |
| 24 | 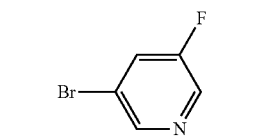<br>2-(5-fluoropyridin-3-yl)-5-(5-methoxypyridin-3-yl)-1H-indole | (DMSO-d₆) δ = 9.03 (s, 1H), 8.51 (s, 2H), 8.23 (t, J = 14 Hz, 2H), 7.95 (s, 1H), 7.63 (s, 1H), 7.75 (s, 2H), 7.25 (d, J = 10.4 Hz, 1H), 3.92 (s, 3H) | |
| 25 | 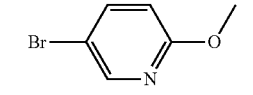<br>5-(5-methoxypyridin-3-yl)-2-(6-methoxypyridin-3-yl)-1H-indole | (DMSO-d₆) δ = 11.68 (s, 1H), 8.71 (s, 1H), 8.50 (s, 1H), 8.20 (d, J = 20 Hz, 2H), 7.89 (s, 1H), 7.62 (s, 1H), 7.43-7.51 (m, 2H), 6.95 (s, 1H), 3.91 (d, J = 3.2 Hz, 6H) | |

TABLE 2-continued

| Ex. | Compound | ¹H NMR (δ ppm) | (G2.A) Ar²—Hal |
|---|---|---|---|
| 26 | 4-(5-(5-(5-methoxypyridin-3-yl)-1H-indol-2-yl)pyridin-2-yl)morpholine | (DMSO-d$_6$) δ = 8.68 (d, J = 2.4 Hz, 1H), 8.43 (d, J = 4.8 Hz, 1H), 8.02-8.05 (m, 1H), 7.92 (s, 1H), 7.59 (s, 1H) 7.45-7.51 (m, 3H), 6.95 (d, J = 8.8 Hz, 1H), 6.86 (s, 1H), 3.72 (t, J = 9.2 Hz, 4H), 3.52 (t, J = 9.6 Hz, 4H), 2.52 (s, 3H) | (G2.A-7) |
| 27 | 5-(5-methoxypyridin-3-yl)-2-(6-(oxetan-3-yl)pyridin-3-yl)-1H-indole | (DMSO-d$_6$) δ = 11.81 (s, 1H), 9.15 (s, 1H), 8.51 (s, 1H), 8.22 (d, J = 8.8 Hz, 2H), 7.93 (s, 1H), 7.62 (s, 1H), 7.50-7.55 (m, 2H), 7.45 (d, J = 8.4 Hz, 1H), 7.11 (s, 1H), 4.90-4.94 (m, 2H), 4.83 (t, J = 12.4 Hz, 2H), 4.44 (t, J = 15.6 Hz, 1H), 3.92 (s, 3H) | (G2.B) |
| 28 | 1-(5-(5-(5-methoxypyridin-3-yl)-1H-indol-2-yl)pyridin-2-yl)-6-oxa-1-azaspiro[3.3]heptane | (DMSO-d$_6$) δ = 8.70 (d, J = 2 Hz, 1H), 8.49 (s, 1H), 8.22 (d, J = 2.8 Hz, 1H), 8.03-8.06 (m, 1H), 7.86 (s, 1H), 7.61 (t, J = 4.4 Hz, 1H), 7.46 (t, J = 14 Hz, 2H), 6.85 (d, J = 1.6 Hz, 1H), 6.65 (d, J = 9.2 Hz, 1H), 5.29 (d, J = 7.2 Hz, 2H), 4.63 (d, J = 7.2 Hz, 2H), 3.92 (s, 3H), 3.82 (t, J = 14 Hz, 2H), 2.61 (d, J = 6.8 Hz, 3H) | (G2.A-1) |

Example 29: N,N-dimethyl-5-(5-(2-methylpyridin-4-yl)-1H-indol-2-yl)pyridin-2-amine

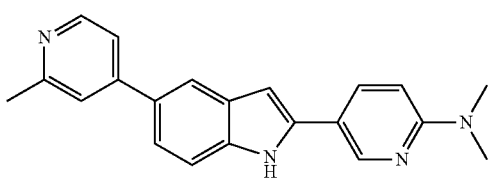

(29)

Example 29 was prepared according to similar experimental conditions used above, starting from intermediate (U3) reacting with 5-bromo-N,N-dimethylpyridin-2-amine (Scheme 3, step iii), followed by coupling with 3-methoxypyridyl-5-yl-boronic acid (Scheme 2, step ii) and final Boc deprotection (Scheme 1, step i). (¹H NMR, DMSO-d$_6$) δ=8.63 (d, J=2.4 Hz, 1H), 8.43 (d, J=5.6 Hz, 1H), 7.96-7.99 (m, 1H), 7.91 (s, 1H), 7.59 (s, 1H), 7.46-7.51 (m, 3H), 6.80 (d, J=1.6 Hz, 1H), 6.75 (t, J=9.2 Hz, 1H), 3.08 (s, 6H), 2.52 (s, 3H).

The following compounds of the invention were prepared according to similar experimental conditions used above, starting from intermediate (U10) and coupling with boronic acid Ar¹—B(OH)$_2$ (Scheme 2, step ii) and final Boc deprotection (Scheme 1, step i):

| Ex. | Compound | ¹H NMR (δ ppm) | Ar¹—B(OR)₂ |
|---|---|---|---|
| 30 | 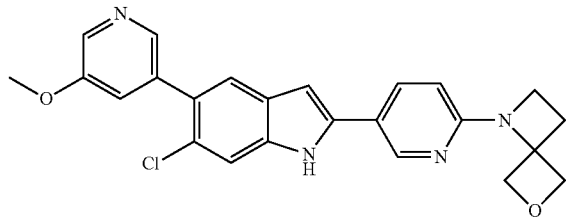 [SMILES: COc1cncc(-c2ccc3[nH]c(-c4ccc(N5CCC56COC6)nc4)cc3c2)c1]<br>4-(5-(5-methoxypyridin-3-yl)-1H-indol-2-yl)-N,N-dimethylpyridin-2-amine | (MeOD) δ = 8.76 (s,1H), 8.15-8.49 (m, 3H), 7.43-7.74 (m, 6H), 4.12 (s, 3H), 3.38 (s, 6H). | 3-methoxy-pyridyl-5-yl-boronic acid |
| 31 | 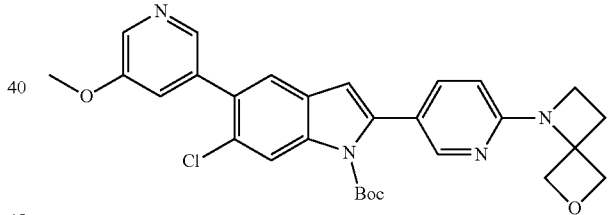<br>N,N-dimethyl-4-(5-(quinolin-4-yl)-1H-indol-2-yl)pyridin-2-amine | (MeOD) δ = 9.19 (d, J = 6.0 Hz, 1H), 8.45 (d, J = 8.4 Hz, 1H), 8.31-8.33 (m, 1H), 8.20-8.25 (m, 1H), 8.11-8.12 (m, 2H), 7.99 (m, 1H), 7.93 (d, J = 6.8 Hz, 1H), 7.81 (d, J = 8.8 Hz, 1H), 7.66 (dd, J = 8.4, 1.6 Hz, 1H), 7.58-7.61 (m, 2H), 7.46 (dd, J = 6.8, 1.6 Hz, 1H), 3.40 (s, 6H) | 4-quinolinyl boronic acid |

Example 32: 1-(5-(6-chloro-5-(5-methoxypyridin-3-yl)-1H-indol-2-yl)pyridin-2-yl)-6-oxa-1-azaspiro[3.3]heptane (32)

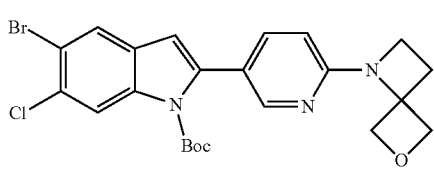 [SMILES: CC(C)(C)OC(=O)n1c(-c2ccc(N3CCC34COC4)nc2)cc2cc(Br)c(Cl)cc21]

tert-butyl 2-(6-(6-oxa-1-azaspiro[3.3]heptan-1-yl)pyridin-3-yl)-5-bromo-6-chloro-1H-indole-1-carboxylate (32.1)

According to Scheme 3, step iii: A mixture of intermediate (U4) (881 mg, 2.35 mmol), compound (G2.A-8) (200 mg, 784 umol), Cs₂CO₃ (511 mg, 1.57 mmol), Pd(dppf)Cl₂·CH₂Cl₂ (64.0 mg, 78.4 umol) in dioxane:H₂O (10/1) (2.00 mL) was degassed and purged with N₂ for 3 times, and then the mixture was stirred at 80° C. for 2 hrs under N₂ atmosphere. The reaction mixture was filtered and concentrated under reduced pressure to give a residue. The residue was purified by prep-TLC (SiO₂, PE/EtOAc=3/1) to give intermediate (32.1) (478 mg) was obtained as a white solid, which was used without further purification in the next step. ¹HNMR (CDCl₃): δ ppm 8.31 (t, J=31.6 Hz, 2H), 7.80 (d, J=18.4 Hz, 1H), 7.51-7.57 (m, 2H), 6.65-6.71 (m, 1H), 5.38-5.44 (m, 2H), 4.73-4.78 (m, 2H), 3.88-3.94 (m, 2H), 2.56-2.64 (m, 2H), 1.44 (d, J=3.2 Hz, 9H).

tert-butyl 2-(6-(6-oxa-1-azaspiro[3.3]heptan-1-yl)pyridin-3-yl)-6-chloro-5-(5-methoxypyridin-3-yl)-1H-indole-1-carboxylate (32.2

According to Scheme 2, step ii: A mixture of intermediate (32.1) (478 mg), 5-methoxy-pyridyl-3-yl-boronic acid (290 mg, 1.89 mmol), Cs₂CO₃ (617 mg, 1.89 mmol), Pd(dppf)Cl₂·CH₂Cl₂ (77.3 mg, 94.7 umol) in dioxane/H₂O (10/1) (10.0 mL) was degassed and purged with N₂ for 3 times, and then the mixture was stirred at 80° C. for 2 hrs under N₂ atmosphere. The reaction mixture was filtered and concentrated under reduced pressure to give a residue. The residue was purified by prep-TLC (SiO₂, PE/EtOAc=1/1, Rf=0.38) to give intermediate (32.2) (100 mg, crude) as a yellow solid.

Example 32: 1-(5-(6-chloro-5-(5-methoxypyridin-3-yl)-1H-indol-2-yl)pyridin-2-yl)-6-oxa-1-azaspiro[3.3]heptane According to Scheme 1, step i: A mixture of intermediate (32.2) (100 mg, 188 umol) in formic acid (1.00 mL) was degassed and purged with N₂ for 3 times, and then the mixture was stirred at 20° C. for 12 hrs under N₂ atmosphere. The reaction mixture was concentrated under reduced pressure to give a residue. The residue was purified by prep-HPLC (column: Nano-Micro UniSil 5-100 C18

ULTRA 100*250 mm 5 um; mobile phase: [water (0.225% FA)-ACN]; B %: 10%-40%, 11 min) to give yellow solid. The solid was dissolved with 15% NaOH (1.00 mL) and stirred at 25° C. for 30 mins. Using a centrifuge separation to obtain yellow solid from the mixture. The solid was washed with H₂O (1.00 mL×5). Then the solid was freeze-dried to give Example 32 (13.6 mg, 16.8% yield, 100% purity) was obtained as a yellow solid. $^1$H NMR (DMSO-d$_6$) δ ppm=8.69 (d, J=2.4 Hz, 1H), 8.30 (d, J=2.8 Hz, 1H), 8.24 (d, J=2 Hz, 1H), 8.03-8.05 (m, 1H), 7.56 (d, J=16.8 Hz, 1H), 7.44 (t, J=4.4 Hz, 1H), 6.84 (s, 1H), 6.65 (d, J=8.8 Hz, 1H), 5.29 (d, J=7.2 Hz, 2H), 4.63 (d, J=7.2 Hz, 2H), 3.88 (s, 3H), 3.82 (t, J=14.4 Hz, 2H), 2.60 (d, J=14 Hz, 2H).

The compounds of the invention under Table 3 were prepared according to similar experimental conditions used above, starting from compound (U4) reacting with 1-(4-bromopyridin-2-yl)-6-oxa-1-azaspiro[3.3]heptane (G2.A$_4$) (Scheme 3, step iii), followed by coupling with the appropriate boronic acid or ester Ar$^1$—B(OR)$_2$ (Scheme 2, step iii and final Boc deprotection using (Scheme 1, step i):

TABLE 3

| Ex. | Compound | $^1$H NMR (δ ppm) | Starting material G1 Ar$^1$—B(OH)$_2$ |
|---|---|---|---|
| 33 | 1-(4-(6-chloro-5-(5-methoxypyridin-3-yl)-1H-indol-2-yl)pyridin-2-yl)-6-oxa-1-azaspiro[3.3]heptane | (DMSO-d$_6$) δ = 8.31 (d, J = 2.4 Hz, 1H), 8.24 (s, 1H), 8.20 (d, J = 5.6 Hz, 1H), 7.67 (s, 1H), 7.60 (s, 1H), 7.44 (s, 1H), 7.14 (d, J = 4 Hz, 1H), 6.88 (s, 1H), 5.37 (d, J = 6.8 Hz, 2H), 4.58 (d, J = 6.8 Hz, 2H), 3.88 (s, 3H), 3.85 (t, J = 14 Hz, 2H), 2.63 (t, J = 12 Hz, 2H) | |
| 34 | 1-(4-(6-chloro-5-(2-methylpyridin-4-yl)-1H-indol-2-yl)pyridin-2-yl)-6-oxa-1-azaspiro[3.3]heptane | (DMSO-d$_6$) δ = 8.49 (d, J = 5.2 Hz, 1H), 8.20 (d, J = 5.6 Hz, 1H), 7.62 (s, 1H), 7.58 (s, 1H), 7.34 (s, 1H), 7.28 (d, J = 3.6 Hz, 1H), 7.14 (d, J = 4.8 Hz, 2H), 6.88 (s, 1H), 5.37 (t, J = 18.4 Hz, 2H), 4.58 (d, J = 6.8 Hz, 2H), 3.84 (t, J = 14 Hz, 2H), 2.62 (t, J = 14 Hz, 2H). | |

The compounds of the invention under Table 3a were prepared according to similar experimental conditions used above, starting from compound (U4) reacting with Hal-Ar$^2$ (G2.A) (Scheme 3, step iii), followed by coupling with 5-methoxy-pyridyl-3-yl-boronic acid (Scheme 2, step iii and final Boc deprotection using (Scheme 1, step i):

TABLE 3a

| Ex. | Compound | $^1$H NMR (δ ppm) or LC-MS RT (min)/[MH]$^+$ | Starting material (G2.A) Hal—Ar$^2$ |
|---|---|---|---|
| 35 | | 11.68 (s, 1H), 8.60 (s, 1H), 8.30 (s, 1H), 8.23 (s, 1H), 7.98 (d, J = 8.0 Hz, 1H), 7.55 (s, 1H), 7.50 (s, 1H), 7.43 (s, 1H), 6.81 (s, 1H), 6.51 (d, J = 8.8 Hz, 1H), 4.74 (s, 4H), 4.16 (s, 4H), 3.88 (s, 3H) | (G2.A-9) |

TABLE 3a-continued

| Ex. | Compound | $^1$H NMR (δ ppm) or LC-MS RT (min)/[MH]$^+$ | Starting material (G2.A) Hal—Ar$^2$ |
|---|---|---|---|
| 36 | 6-(5-(6-chloro-5-(5-methoxypyridin-3-yl)-1H-indol-2-yl)pyridin-2-yl)-2-oxa-6-azaspiro[3.3]heptane | 11.65 (s, 1H), 8.60 (d, J = 2.4 Hz, 1H), 8.30 (d, J = 3.2 Hz, 1H), 8.23 (d, J = 1.2 Hz, 1H), 7.97 (d, J = 6.0 Hz, 1H), 7.55 (s, 1H), 7.50 (s, 1H), 7.43 (s, 1H), 6.80 (s, 1H), 6.49 (d, J = 8.4 Hz, 1H), 3.88 (s, 3H), 3.77 (s, 4H), 3.56 (d, J = 4.8 Hz, 4H), 1.75 (d, J = 10 Hz, 4H) | (G2.A-22) |
| 37 | 2-(5-(6-chloro-5-(5-methoxypyridin-3-yl)-1H-indol-2-yl)pyridin-2-yl)-7-oxa-2-azaspiro[3.5]nonane | 11.65 (s, 1H), 8.59 (d, J = 2.0 Hz, 1H), 8.29 (d, J = 2.8 Hz, 1H), 8.23 (d, J = 2.0 Hz, 1H), 7.96 (t, J = 8.8 Hz, 1H), 7.55 (s, 1H), 7.49 (s, 1H), 7.43 (t, J = 4.4 Hz, 1H), 6.80 (s, 1H), 6.50 (d, J = 8.8 Hz, 1H), 5.85 (s, 1H), 3.89 (d, J = 5.2 Hz, 1H), 3.87 (s, 1H), 3.83 (s, 1H), 3.81 (s, 1H), 1.45 (s, 3H). | (G2.A-10) |
| 38 | 1-(5-(6-chloro-5-(5-methoxypyridin-3-yl)-1H-indol-2-yl)pyridin-2-yl)-3-methylazetidin-3-ol | 11.73 (s, 1H), 8.68 (d, J = 2.4 Hz, 1H), 8.30 (d, J = 2.8 Hz, 1H), 8.23 (d, J = 1.6 Hz, 1H), 8.09 (d, J = 8.4 Hz, 1H), 7.57 (s, 1H), 7.52 (s, 1H), 6.43 (t, J = 4.0 Hz, 1H), 6.88 (s, 1H), 6.71 (d, J = 9.2 Hz, 1H), 4.44 (t, J = 25.2 Hz, 4H), 3.88 (s, 3H) | (G2.A-11) |

6-chloro-2-(6-(3,3-difluoroazetidin-1-yl)pyridin-3-yl)-5-(5-methoxypyridin-3-yl)-1H-indole TABLE 3a-continued

| Ex. | Compound | $^1$H NMR (δ ppm) or LC-MS RT (min)/[MH]$^+$ | Starting material (G2.A) Hal—Ar$^2$ |
|---|---|---|---|
| 39 | 1-(5-(6-chloro-5-(5-methoxypyridin-3-yl)-1H-indol-2-yl)pyridin-2-yl)azetidine-3-carboxylic acid | 12.00 (s, 2H), 8.56 (d, J = 2.4 Hz, 1H), 8.43 (d, J = 2.8 Hz, 1H), 8.38 (s, 1H), 8.30 (d, J = 8.0 Hz, 1H), 7.70 (s, 1H), 7.65 (s, 1H), 7.57 (s, 1H), 7.00 (s, 1H), 6.86 (d, J = 9.2 Hz, 1H), 4.38 (t, J = 18 Hz, 2H), 4.25 (d, J = 8.4 Hz, 2H), 3.93 (s, 3H), 3.63-3.68 (m, 1H) | (G2.A-17) |
| 40 | 1-(5-(6-chloro-5-(5-methoxypyridin-3-yl)-1H-indol-2-yl)pyridin-2-yl)azetidine-3-carboxamide | 11.68 (s, 1H), 8.61 (d, J = 2.0 Hz, 1H), 8.30 (d, J = 2.8 Hz, 1H), 8.23 (d, J = 1.6 Hz, 1H), 7.99 (d, J = 6.4 Hz, 1H), 7.56 (s, 1H), 7.50 (s, 1H), 7.43 (d, J = 2.8 Hz, 1H), 7.04 (s, 1H), 6.82 (s, 2H), 6.51 (d, J = 8.4 Hz, 1H), 4.11 (t, J = 16.4 Hz, 2H), 4.00 (d, J = 14 Hz, 1H), 3.88 (s, 3H), 3.44-3.49 (m, 1H) | (G2.A-19) |
| 41 | (1-(5-(6-chloro-5-(5-methoxypyridin-3-yl)-1H-indol-2-yl)pyridin-2-yl)azetidin-3-yl)methanol | 11.67 (s, 1H), 8.59 (d, J = 2.0 Hz, 1H), 8.30 (d, J = 2.8 Hz, 1H), 8.23 (d, J = 2.0 Hz, 1H), 7.96 (d, J = 8.8 Hz, 1H), 7.55 (s, 1H), 7.50 (s, 1H), 7.43 (d, J = 2.8 Hz, 1H), 6.80 (s, 1H), 6.47 (d, J = 8.8 Hz, 1H), 4.81 (s, 1H), 4.00 (t, J = 16.4 Hz, 2H), 3.88 (s, 3H), 3.72-3.75 (m, 2H), 3.59 (d, J = 6.0 Hz, 2H), 2.80 (d, J = 6.0 Hz, 1H) | (G2.A-21) |

TABLE 3a-continued

| Ex. | Compound | $^1$H NMR (δ ppm) or LC-MS RT (min)/[MH]$^+$ | Starting material (G2.A) Hal—Ar$^2$ |
|---|---|---|---|
| 42 | 6-chloro-5-(5-methoxypyridin-3-yl)-2-(6-(3-methoxypyrrolidin-1-yl)pyridin-3-yl)-1H-indole | 11.63 (s, 1H), 8.61 (d, J = 2.4 Hz, 1H), 8.30 (d, J = 2.8 Hz, 1H), 8.24 (d, J = 1.6 Hz, 1H), 7.97 (d, J = 19.6 Hz, 1H), 7.54(s, 1H), 7.49 (s, 1H), 7.44 (t, J = 4.4 Hz, 1H), 6.78 (s, 1H), 6.58 (d, J = 8.4 Hz, 4H), 4.10 (d, J = 3.6 Hz, 4H), 3.88 (s, 3H), 3.55 (d, J = 3.1 Hz, 3H), 3.41-3.51 (m, 1H), 3.28 (s, 3H), 2.05-2.10 (s, 2H) | (G2.A-13) |
| 43 | N-(1-(5-(6-chloro-5-(5-methoxypyridin-3-yl)-1H-indol-2-yl)pyridin-2-yl)pyrrolidin-3-yl)methanesulfonamide | 11.64 (s, 1H), 8.62 (d, J = 2.4 Hz, 1H), 8.30 (d, J = 2.4 Hz, 1H), 8.24 (s, 1H), 7.96 (t, J = 11.2 Hz, 1H), 7.54 (s, 1H), 7.50 (s, 1H), 7.45 (d, J = 6.8 Hz, 1H), 6.79 (s, 1H), 6.58 (d, J = 8.8 Hz, 4H), 4.06 (d, J = 6.4 Hz, 1H), 3.88 (s, 3H), 3.76 (d, J = 3.2 Hz, 1H), 3.57 (s, 1H), 3.44 (d, J = 9.2 Hz, 1H), 3.37 (d, J = 6.0 Hz, 1H), 3.28 (s, 1H), 2.99 (s, 3H), 2.26 (d, J = 5.6 Hz, 1H) | (G2.A-16) |
| 44 | (1-(5-(6-chloro-5-(5-methoxypyridin-3-yl)-1H-indol-2-yl)pyridin-2-yl)pyrrolidin-2-yl)methanol | 11.63 (s, 1H), 8.59 (s, 1H), 8.29 (d, J = 2.0 Hz, 1H), 8.23 (s, 1H), 7.95 (d, J = 8.8 Hz, 1H), 7.54 (s, 1H), 7.50 (s, 1H), 7.43 (s, 1H), 6.78 (s, 1H), 6.62 (d, J = 8.8 Hz, 1H), 4.87 (s, J = 11.2 Hz, 1H), 4.09 (s, 1H), 3.88 (s, 3H), 3.60 (t, J = 10 Hz, 2H), 3.50 (t, J = 15.2 Hz, 2H), 2.02 (d, J = 6.4 Hz, 1H), 1.93 (t, J = 2.4 Hz, 2H) | (G2.A-23) |
| 45 | 1-(5-(6-chloro-5-(5-methoxypyridin-3-yl)-1H-indol-2-yl)pyridin-2-yl)-5-(hydroxymethyl)pyrrolidin-2-one | 2.584/449.1 | |

TABLE 3a-continued

| Ex. | Compound | ¹H NMR (δ ppm) or LC-MS RT (min)/[MH]⁺ | Starting material (G2.A) Hal—Ar² |
|---|---|---|---|
| 46 | 4-(5-(6-chloro-5-(5-methoxypyridin-3-yl)-1H-indol-2-yl)-3-fluoropyridin-2-yl)morpholine | 11.80 (s, 1H), 8.58 (s, 1H), 8.30 (d, J = 2.8 Hz, 1H), 8.07 (s, 1H), 8.03 (d, J = 1.6 Hz, 1H), 7.60 (s, 1H), 7.55 (s, 1H), 7.44 (d, J = 1.2 Hz, 1H) 6.99 (s, 1H) 3.88 (s, 3H), 3.74 (t, J = 9.6 Hz, 4H), 3.46 (d, J = 9.6 Hz, 4H) | (G2.A-20) |
| 47 | 6-chloro-5-(5-methoxypyridin-3-yl)-2-(6-(4-(oxetan-3-yl)piperazin-1-yl)pyridin-3-yl)-1H-indole | 11.68 (s, 1H), 8.65 (d, J = 2.0 Hz, 1H), 8.30 (d, J = 2.8 Hz, 1H), 8.24 (s, 1H), 7.98-8.01 (m, 1H), 7.56 (s, 1H), 7.51 (s, 1H), 7.43 (s, 1H), 6.97 (d, J = 8.8 Hz, 1H), 6.83 (s, 1H), 4.57 (t, J = 12.8 Hz, 2H), 4.48 (t, J = 12 Hz, 1H), 3.88 (s, 3H), 3.60 (d, J = 4.4 Hz, 4H), 3.44 (t, J = 12.4 Hz, 1H), 2.36 (t, J = 9.2 Hz, 4H) | (G2.A-14) |
| 48 | 6-chloro-2-(6-(4-ethylpiperazin-1-yl)pyridin-3-yl)-5-(5-methoxypyridin-3-yl)-1H-indole | 11.67 (s, 1H), 8.65 (d, J = 2.4 Hz, 1H), 8.30 (d, J = 2.8 Hz, 1H), 8.24 (d, J = 1.6 Hz, 1H), 7.97-8.00 (m, 1H), 7.56 (s, 1H), 7.51 (s, 1H), 7.43 (d, J = 2.0 Hz, 1H), 6.95 (d, J = 7.2 Hz, 1H), 3.88 (s, 3H), 3.55 (t, J = 9.6 Hz, 4H), 2.45 (t, J = 9.6 Hz, 4H), 2.37 (t, J = 14.4 Hz, 2H), 1.04 (t, J = 14.4 Hz, 3H) | |

TABLE 3a-continued

| Ex. | Compound | ¹H NMR (δ ppm) or LC-MS RT (min)/[MH]⁺ | Starting material (G2.A) Hal—Ar² |
|---|---|---|---|
| 49 | 4-(5-(6-chloro-5-(5-methoxypyridin-3-yl)-1H-indol-2-yl)pyridin-2-yl)thiomorpholine 1,1-dioxide | 11.85 (s, 1H), 8.71 (s, 1H), 8.40 (d, J = 16 Hz, 2H), 8.10 (d, J = 8.8 Hz, 1H), 7.68 (s, 1H), 7.63 (s, 1H), 7.54 (s, 1H), 7.18 (d, J = 9.6 Hz, 1H), 6.92 (s, 1H), 4.13 (s, 4H), 3.93 (s, 3H), 3.15 (s, 4H) | (G2.A-18) |
| 50 | 6-chloro-2-(6-(4,4-difluoropiperidin-1-yl)pyridin-3-yl)-5-(5-methoxypyridin-3-yl)-1H-indole | 8.69 (s, 1H), 8.60 (d, J = 2.4 Hz, 1H), 8.57 (s, 1H), 8.30 (d, J = 8.4 Hz, 1H), 8.07 (s, 1H), 7.71 (s, 1H), 7.60 (s, 1H), 7.33 (d, J = 8.8 Hz, 1H), 7.02 (s, 1H), 4.01 (s, 3H), 3.85 (s, 4H), 2.08 (d, J = 8.8 Hz, 5H) | (G2.A-5) |
| 51 | 4-(5-(6-chloro-5-(5-methoxypyridin-3-yl)-1H-indol-2-yl)pyridin-2-yl)-1-methylpiperazin-2-one | 11.70 (s, 1H), 8.65 (d, J = 2.4 Hz, 1H), 8.30 (d, J = 2.8 Hz, 1H), 8.24 (s, 1H), 8.03-8.06 (m, 1H), 7.56 (s, 1H), 7.51 (s, 1H), 7.44 (d, J = 2.0 Hz, 1H), 6.99 (d, J = 9.2 Hz, 1H), 6.86 (s, 1H), 4.13 (s, 2H), 3.87 (d, J = 6.8 Hz, 5H), 3.44 (t, J = 10.4 Hz, 2H), 2.09 (s, 3H) | (G2.A-15) |

TABLE 3a-continued

| Ex. | Compound | $^1$H NMR (δ ppm) or LC-MS RT (min)/[MH]$^+$ | Starting material (G2.A) Hal—Ar$^2$ |
|---|---|---|---|
| 52 | 3'-(6-chloro-5-(5-methoxypyridin-3-yl)-1H-indol-2-yl)-1-methyl-5'H-spiro[azetidine-3,7'-furo[3,4-b]pyridine] | 2.013/419.1 | (G2.C) |
| 53 | 7-(6-chloro-5-(5-methoxypyridin-3-yl)-1H-indol-2-yl)-4-methyl-3,4-dihydro-2H-pyrido[3,2-b][1,4]oxazine | 12.31 (s, 1H), 8.58 (d, J = 2.8 Hz, 1H), 8.56 (s, 1H), 8.25 (d, J = 2.0 Hz, 1H), 8.03 (s, 1H), 7.83 (s, 1H), 7.70 (s, 1H), 7.59 (s, 1H), 7.04 (s, 1H), 4.35 (d, J = 9.6 Hz, 2H), 4.00 (s, 3H), 3.68 (d, J = 4.4 Hz, 2H), 3.28 (s, 3H) | (G2.D) |
| 54 | (5-(6-chloro-5-(5-methoxypyridin-3-yl)-1H-indol-2-yl)pyridin-2-yl)(oxetan-3-yl)methanol | 11.92 (s, 1H), 8.63 (d, J = 2.0 Hz, 1H), 8.31 (d, J = 3.2 Hz, 1H), 8.25 (d, J = 2.0 Hz, 1H), 8.00 (d, J = 8.4 Hz, 1H), 7.84 (d, J = 2.0 Hz, 1H), 7.66 (s, 1H), 7.62 (s, 1H), 7.45 (d, J = 2.8 Hz, 1H), 7.20 (s, 1H), 5.74 (d, J = 4.8 Hz, 1H), 4.94 (t, J = 7.6 Hz, 1H), 4.61 (t, J = 9.2 Hz, 2H), 4.40-4.48 (m, 2H), 3.89 (s, 3H) | |
| 55 | 6-chloro-2-(6-(methoxy(oxetan-3-yl)methyl)pyridin-3-yl)-5-(5-methoxypyridin-3-yl)-1H-indole | 11.94 (s, 1H), 8.63 (s, 1H), 8.31 (d, J = 2.8 Hz, 1H), 8.25 (s, 1H), 8.04 (d, J = 8.4 Hz, 1H), 7.83 (t, J = 8.0 Hz, 1H), 7.67 (s, 1H), 7.62 (s, 1H), 7.46 (d, J = 1.6 Hz 1H), 7.23 (s, 1H), 4.65 (t, J = 14.4 Hz, 2H), 4.59 (d, J = 6.0 Hz, 1H), 4.42 (d, J = 8.4 Hz, 1H), 4.33 (d, J = 6.0 Hz, 1H), 3.88 (s, 3H), 3.21 (s, 3H) | |

TABLE 3a-continued

| Ex. | Compound | $^1$H NMR (δ ppm) or LC-MS RT (min)/[MH]$^+$ | Starting material (G2.A) Hal—Ar$^2$ |
|---|---|---|---|
| 56 | 2-(5-(6-chloro-5-(5-methoxypyridin-3-yl)-1H-indol-2-yl)pyridin-2-yl)propan-1-ol | 9.14 (s, 1H), 8.91-8.94 (m, 1H), 8.63 (d, J = 8.0 Hz, 2H), 8.34 (d, J = 2.4 Hz, 1H), 8.12 (d, J = 8.8 Hz, 1H), 7.87 (s, 1H), 7.75 (s, 1H), 7.36 (s, 1H), 4.12 (s, 3H), 3.91-3.95 (m, 1H), 3.77-3.82 (m, 1H), 3.40 (t, J = 12 Hz, 1H), 1.47 (d, J = 6.8 Hz, 3H) | 5-bromo-2-(1-hydroxypropan-2-yl)pyridine |
| 57 | 5-(6-chloro-5-(5-methoxypyridin-3-yl)-1H-indol-2-yl)-1-methylpyridin-2(1H)-one | 11.61 (s, 1H), 8.30 (d, J = 2.4 Hz, 2H), 8.23 (d, J = 1.6 Hz, 1H), 7.94 (d, J = 9.6 Hz, 1H), 7.57 (s, 1H), 7.52 (s, 1H), 7.43 (d, J = 2.0 Hz, 1H), 6.78 (s, 1H), 6.53 (d, J = 9.2 Hz, 1H), 3.88 (s, 3H), 3.52 (s, 3H) | 5-bromo-1-methylpyridin-2(1H)-one |
| 58 | 4-(6-chloro-5-(5-methoxypyridin-3-yl)-1H-indol-2-yl)-1-(cyclopropylmethyl)pyridin-2(1H)-one | 11.93 (s, 1H), 8.31 (d, J = 2.8 Hz, 1H), 8.24 (d, J = 1.6 Hz, 1H), 7.80 (d, J = 7.2 Hz, 1H), 7.68 (s, 1H), 7.58 (s, 1H), 7.43-7.47 (m, 1H), 7.20 (s, 1H), 6.91 (d, J = 1.9 Hz, 1H), 6.76 (d, J = 2.0 Hz, 1H), 6.74 (s, 1H), 3.89 (s, 3H), 3.75 (d, J = 7.2 Hz, 2H), 2.07 (s, 1H), 1.16-1.30 (m, 1H), 0.45-0.52 (m, 2H), 0.37-0.44 (m, 2H) | 4-bromo-1-(cyclopropylmethyl)pyridin-2(1H)-one (G2.E) |

The compounds of the invention under Table 3b were prepared according to similar experimental conditions used above, starting from intermediates (U4a) and (U4b) reacting with 4-(5-bromopyridin-2-yl)morpholine (Scheme 3, step iii), followed by coupling with 5-methoxy-pyridyl-3-yl-boronic acid (Scheme 2, step iii and final Boc deprotection (Scheme 1, step i):

TABLE 3b

| Ex. | Compound | $^1$H NMR (δ ppm) | Starting material |
|---|---|---|---|
| 59 | 4-(5-(7-chloro-5-(5-methoxypyridin-3-yl)-1H-indol-2-yl)pyridin-2-yl)morpholine | 11.6 (s, 1H), 8.78 (s, 1H), 8.52 (s, 1H), 8.25 (s, 1H), 8.18 (d, J = 8.4 Hz, 1H), 7.85 (s, 1H), 7.66 (s, 1H), 7.54 (s, 1H), 6.97-6.94 (m, 2H), 3.93 (s, 3H), 3.72 (s, 4H), 3.53 (s, 4H) | (U4a) |

TABLE 3b-continued

| Ex. | Compound | ¹H NMR (δ ppm) | Starting material |
|---|---|---|---|
| 60 | 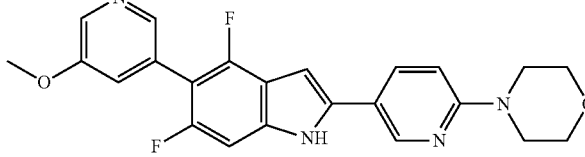 4-(5-(4,6-difluoro-5-(5-methoxypyridin-3-yl)-1H-indol-2-yl)pyridin-2-yl)morpholine | 12.13 (m, 1H), 8.68 (d, J = 2.0 Hz, 1H), 8.48-8.35 (m, 2H), 8.23-8.14 (m, 1H), 7.74-7.65 (m, 1H), 7.27-7.20 (m, 1H), 7.15-6.99 (m, 2H), 3.92 (s, 3H), 3.80-3.70 (m, 4H), 3.62-3.50 (m, 4H) | (U4b) |

The compounds of the invention under Table 3c were prepared according to similar experimental conditions used above, starting from intermediates U5 and coupling with the appropriate boronic acid Ar¹—B(OH)₂ (Scheme 2, step iii) and final Boc deprotection (Scheme 1, step i):

TABLE 3c

| Ex. | Compound | ¹H NMR (δ ppm) | Starting material G1 Ar¹-B(OH)₂ |
|---|---|---|---|
| 61 | 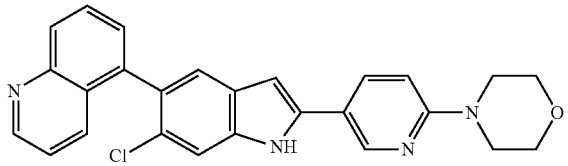 4-(5-(6-chloro-5-(quinolin-5-yl)-1H-indol-2-yl)pyridin-2-yl)morpholine | 11.85 (s, 1H), 9.05 (d, J = 3.6 Hz, 1H), 8.67 (d, J = 2.4 Hz, 1H), 8.17 (d, J = 8.4 Hz, 1H), 8.11 (d, J = 6.8 Hz, 1H), 7.98 (s, 1H), 7.97 (s, 1H), 7.95 (s, 2H), 7.66 (d, J = 6.4 Hz, 1H), 7.57 (d, J = 14 Hz, 1H), 7.05 (d, J = 8.8 Hz, 1H), 6.89 (s, 1H), 3.73 (t, J = 9.6 Hz, 4H), 3.56 (t, J = 9.6 Hz, 4H) | quinolin-5-yl boronic acid |
| 62 | 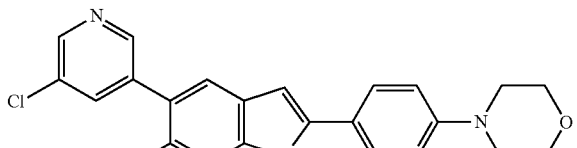 4-(5-(6-chloro-5-(5-chloropyridin-3-yl)-1H-indol-2-yl)pyridin-2-yl)morpholine | 11.80 (s, 1H), 8.64-8.66 (m, 2H), 8.62 (d, J = 1.6 Hz, 1H), 8.09 (d, J = 7.2 Hz, 1H), 8.04 (t, J = 4.0 Hz, 1H), 7.62 (s, 1H), 7.54 (s, 1H), 7.03 (d, J = 8.4 Hz, 1H), 6.89 (s, 1H), 3.72 (t, J = 9.6 Hz, 4H), 3.54 (t, J = 9.6 Hz, 4H) | 5-choloro-pyridin-3-yl boronic acid |

Example 63: 4-fluoro-5-(5-methoxypyridin-3-yl)-2-(2-methylpyridin-4-yl)-1H-indole and Example 64: 6-fluoro-5-(5-methoxypyridin-3-yl)-2-(2-methylpyridin-4-yl)-1H-indole

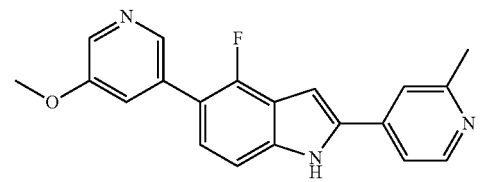

(63)

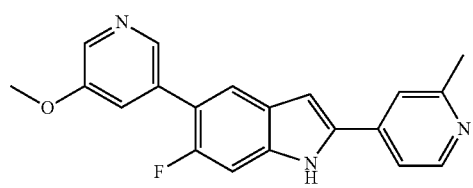

(64)

4-bromo-3-fluorophenyl)hydrazine (63.1)

According to Scheme 5, step i: 4-bromo-3-fluorophenylamine (8.00 g, 42.1 mmol) was suspended in concentrated HCl (48.0 mL) and the mixture was cooled to −10° C. A solution of NaNO₂ (3.05 g, 44.2 mmol) in H₂O (21.0 mL) was added very slowly to the reaction mixture. The mixture was stirred at −10° C. for 30 mins and then a solution of SnCl$_2$·2H$_2$O (35.2 g, 156 mmol) in concentrated HCl (48.0 mL) was added very slowly. The reaction mixture was directly filtered and concentrated in vacuo to give the intermediate (63.1) (6.00 g, 59.0% yield, HCl) as pink solid, which was directly used without further purification. $^1$HNMR (DMSO-d$^6$): δ ppm 10.46 (s, 2H), 8.75 (s, 1H), 7.56 (t, J=16.8 Hz, 1H), 6.98-7.01 (m, 1H), 6.78 (t, J=8.4 Hz, 1H).

4-(1-(2-(4-bromo-3-fluorophenyl)hydrazineylidene)ethyl)-2-methylpyridine (63.2)

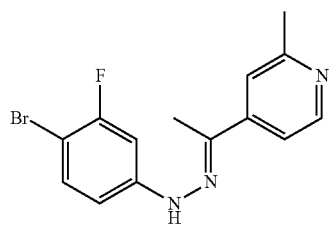 [SMILES: C/C(=N\Nc1ccc(Br)c(F)c1)c1ccnc(C)c1]

According to Scheme 5, step ii: To a solution of intermediate (63.1) (600 mg, 2.48 mmol, HCl) and 4-acetyl-2-methyl pyridine (336 mg, 2.48 mmol) in EtOH (10.0 mL) was added p-TsOH (85.6 mg, 497 umol). The mixture was stirred at 40° C. for 4 hrs. The reaction mixture was directly filtered and then the filtrate was further triturate with NaHCO$_3$(aq) (10.0 mL). The resulting precipitate was washed with ACN (5.00 mL×3) and then filtered and dried in vacuum to give intermediate (63.2) (640 mg, 80.0% yield) as a yellow solid. $^1$HNMR (MeOD): δ ppm 8.48 (d, J=6.4 Hz, 1H), 8.18 (t, J=8.4 Hz, 1H), 8.13 (s, 1H), 7.48 (t, J=16.4 Hz, 1H), 7.29 (t, J=16.4 Hz, 1H), 7.13 (t, J=54 Hz, 1H), 2.77 (s, 3H), 2.34 (s, 3H).

5-bromo-4-fluoro-2-(2-methylpyridin-4-yl)-1H-indole (63.3) and 5-bromo-6-fluoro-2-(2-methylpyridin-4-yl)-1H-indole (64.1)

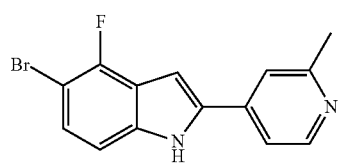

(63.3)

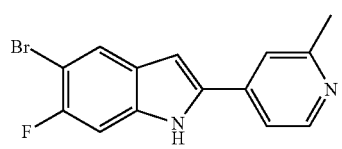

(64.1)

According to Scheme 5, step iii: to a solution of compound (63.2) (300 mg, 931 umol) was added Eaton's reagent (1.20 mL). The mixture was stirred at 60° C. for 3 hrs. The reaction mixture was dropwised to a mixture of ice and Na$_2$CO$_3$ and adjust pH 8~9, and then filtered and washed with H$_2$O (3.00 mL×3). And the residue was dissolved in THF, dried over anhydrous Na$_2$SO$_4$, filtered and concentrated under reduced pressure to give a mixture of intermediates (63.3) and (64.1) (220 mg, 77.4% yield) as a yellow solid without further purification. $^1$HNMR (MeOD): δ ppm 7.78 (d, J=6.8 Hz, 1H), 7.68 (d, J=5.6 Hz, 1H), 7.54 (t, J=6.8 Hz, 1H), 7.23 (d, J=9.2 Hz, 1H), 7.17 (d, J=8.4 Hz, 1H), 7.04 (d, J=5.8 Hz, 1H), 2.57 (s, 3H). LCMS [M+H$^+$]: 305.0.

Example 63 (4-fluoro-5-(5-methoxypyridin-3-yl)-2-(2-methylpyridin-4-yl)-1H-indole) and Example 64 (6-fluoro-5-(5-methoxypyridin-3-yl)-2-(2-methylpyridin-4-yl)-1H-indole)

According to Scheme 7, step i: A mixture of intermediates (63.3) and (64.1) (220 mg, 721 umol), (5-methoxypyridin-3-yl)boronic acid (111 mg, 721 umol), Cs$_2$CO$_3$ (470 mg, 1.44 mmol), Pd(dppf)Cl$_2$·CH$_2$Cl$_2$ (29.4 mg, 36.1 umol) in dioxane (5.00 mL) and H$_2$O (0.500 mL) was degassed and purged with N$_2$ for 3 times, and then the mixture was stirred at 120° C. for 12 hrs under N$_2$ atmosphere. The reaction mixture was washed with MeOH (2.00 mL×3), filtered and concentrated under reduced pressure to give a residue. The residue was purified by prep-HPLC (neutral column: Xtimate C18 150*25 mm*5 um; mobile phase: [water (10 mM NH$_4$HCO$_3$)-ACN]; B %: 45%-65%, 10.5 min) to give the mixture of the desired compound as a yellow solid. The mixture was further separated by SFC (column: AS (250*30 mm, 5 μm); mobile phase: [0.1% HN$_3$H$_2$O MeOH]; B %: 42%-42%, 7 min) to provide Example 63 (9.90 mg, 4.08% yield, 99.0% purity) as a yellow solid: $^1$H NMR (MeOD) δ ppm=8.45 (d, J=4.8 Hz, 1H), 8.36 (s, 1H), 8.21 (s, 1H), 7.74 (s, 1H), 7.65 (s, 1H), 7.61 (s, 1H), 7.39 (d, J=8.8 Hz, 1H), 7.32 (t, J=15.6 Hz, 1H), 7.26 (s, 1H), 4.61 (s, 1H), 3.95 (d, J=2.4 Hz, 3H), 2.61 (d, J=2.4 Hz, 3H); and Example 64 (14.6 mg, 6.04% yield, 99.4%=purity) as a yellow solid: $^1$H NMR (MeOD) δ ppm=8.41 (d, J=5.6 Hz, 1H), 8.32 (s, 1H), 8.21 (d, J=2.8 Hz, 1H), 7.71 (d, J=7.6 Hz, 1H), 7.67 (s, 1H), 7.57-7.60 (i, 2H), 7.26 (d, J=11.6 Hz, 1H), 7.17 (s, 1H), 3.54 (s, 3H), 2.58 (s, 3H).

The compounds of the invention under Table 4 were prepared according to similar experimental conditions used above, starting from disubstituted anilines described hereafter and 4-acetyl-2-methylpyridine (Scheme 5, step ii), followed by cyclisation using Eaton's reagent (Scheme 5, step iii) and final coupling reaction with (5-methoxypyridin-3-yl)boronic acid (Scheme 7, step i):

TABLE 4

| Ex. | Compound | $^1$H NMR (δ ppm) | Aniline |
|---|---|---|---|
| 65 | 4-chloro-5-(5-methoxypyridin-3-yl)-2-(2-methylpyridin-4-yl)-1H-indole | (MeOD) δ = 8.44 (d, J = 5.2 Hz, 1H), 8.23 (s, 1H), 7.74 (s, 1H), 7.66 (d, J = 5.6 Hz, 1H), 7.52 (t, J = 4.4 Hz, 1H), 7.49 (d, J = 8.4 Hz, 1H), 7.26 (s, 1H), 7.23 (d, J = 8.4 Hz, 1H), 4.58 (s, 1H), 3.92 (d, J = 4.4 Hz, 3H), 2.60 (s, 3H) | 3-chloro-4-bromoaniline |
| 66 | 6-chloro-5-(5-methoxypyridin-3-yl)-2-(2-methylpyridin-4-yl)-1H-indole | (MeOD) δ = 8.43 (d, J = 5.6 Hz, 1H), 8.23 (d, J = 2.8 Hz, 1H), 8.20 (d, J = 1.6 Hz, 1H), 7.70 (s, 1H), 7.61-7.64 (m, 3H), 7.49 (t, J = 4.4 Hz, 1H), 7.17 (s, 1H), 4.61 (s, 1H), 3.93 (s, 3H), 2.60 (s, 3H) | |
| 67 | 5-(5-methoxypyridin-3-yl)-4-methyl-2-(2-methylpyridin-4-yl)-1H-indole | (MeOD) δ = 8.40 (d, J = 5.2 Hz, 1H), 8.20 (d, J = 2.4 Hz, 1H), 8.13 (d, J = 1.6 Hz, 1H), 7.37 (s, 1H), 7.65 (d, J = 4.8 Hz, 1H), 7.41 (t, J = 4.4 Hz, 1H), 7.37 (d, J = 8.4 Hz, 1H), 7.25 (s, 1H), 7.10 (d, J = 8.4 Hz, 1H), 4.61 (s, 1H), 3.93 (d, J = 4.4 Hz, 3H), 2.59 (s, 3H), 2.50 (s, 3H) | 4-bromo-3-methylaniline |
| 68 | 5-(5-methoxypyridin-3-yl)-6-methyl-2-(2-methylpyridin-4-yl)-1H-indole | (MeOD) δ = 8.39 (d, J = 5.2 Hz, 1H), 8.21 (d, J = 2.4 Hz, 1H), 8.12 (s, 1H), 7.61 (d, J = 5.6 Hz, 1H), 7.46 (s, 1H), 7.41 (d, J = 4 Hz, 1H), 7.37 (s, 1H), 7.11 (s, 1H), 4.61 (s, 2H), 3.92 (s, 3H), 2.58 (s, 3H), 2.35 (s, 3H) | |

The compounds of the invention under Table 5 were prepared according to similar experimental conditions, starting from 4-bromo-3-methylaniline and 4-acetylpyridine (Scheme 5, step ii), followed by cyclisation using Eaton's reagent (Scheme 5 step iii) and final coupling reaction with (pyridin-4-yl)boronic acid (Scheme 7, step i):

TABLE 5

| Ex. | Compound | ¹H NMR (δ ppm) | Aniline |
|---|---|---|---|
| 69 | 4-methyl-2,5-di(pyridin-4-yl)-1H-indole | (DMSO-$d_6$) δ 11.92 (s, 1H), 8.64-8.61 (m, 4H), 7.87 (d, J = 4.4 Hz, 2H) 7.43-7.11 (m, 4H), 7.10 (d, J = 8.4 Hz, 1H), 2.50 (s, 3H) | 4-bromo-3-methylaniline |
| 70 | 6-methyl-2,5-di(pyridin-4-yl)-1H-indole | (DMSO-$d_6$) δ = 11.80 (s, 1H), 8.61 (d, J = 4.0 Hz, 4H), 7.83 (d, J = 4.4 Hz, 2H), 7.48-7.37 (m, 4H), 7.20 (s, 1H), 2.35 (s, 3H) | |

The compounds of the invention under Table 6 were prepared according to similar experimental conditions, starting from 4-bromo-3-chloroaniline and 1-(2-morpholinopyridin-5-yl)ethan-1-one (4-III-A) (Scheme 5, step ii), followed by cyclisation using Eaton's reagent (Scheme 5, step iii) and final coupling reaction with (5-methoxypyridin-3-yl)boronic acid (Scheme 7, step i):

TABLE 6

| Ex. | Compound | ¹H NMR (δ ppm) | Aniline |
|---|---|---|---|
| 71 | 4-(5-(4-chloro-5-(5-methoxypyridin-3-yl)-1H-indol-2-yl)pyridin-2-yl)morpholine | (DMSO-$d_6$) δ = 8.72 (s, 1H), 8.28 (d, J = 15.2 Hz, 2H), 8.09 (d, J = 9.2 Hz, 1H), 7.44 (d, J = 7.6 Hz, 2H), 7.14 (d, J = 8 Hz, 1H), 6.97 (d, J = 11.2 Hz, 1H), 6.91 (s, 1H), 3.89 (d, J = 2.8 Hz, 3H), 3.72 (s, 4H), 3.53 (s, 4H) | 4-bromo-3-chloroaniline |
| 72 | 4-(5-(6-chloro-5-(5-methoxypyridin-3-yl)-1H-indol-2-yl)pyridin-2-yl)morpholine | (DMSO-$d_6$) δ = 8.67 (s, 1H), 8.27 (d, J = 24 Hz, 2H), 8.03 (d, J = 8.8 Hz, 1H), 7.56 (d, J = 20 Hz, 2H), 7.44 (s, 1H), 6.97 (d, J = 9.6 Hz, 1H), 6.85 (s, 1H), 3.88 (s, 3H), 3.72 (s, 4H), 3.52 (s, 4H) | |

Example 73: 4-chloro-2,5-di(pyridin-4-yl)-1H-indole, and Example 74 6-chloro-2,5-di(pyridin-4-yl)-1H-indole

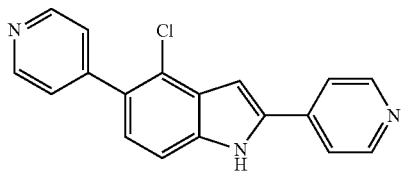
(73)

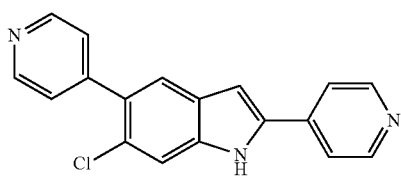
(74)

Mixture of 4-chloro-2,5-di(pyridin-4-yl)-1H-indole (73) and 6-chloro-2,5-di(pyridin-4-yl)-1H-indole (74)

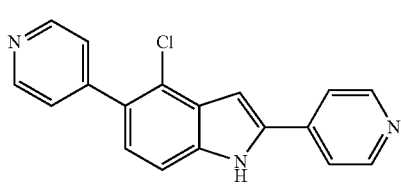
(73)

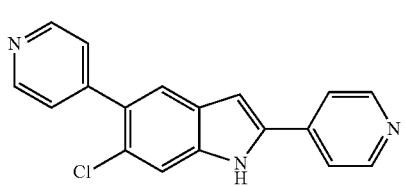
(74)

A mixture of (4-chloro-2,5-di(pyridin-4-yl)-1H-indole (Example 73) and 6-chloro-2,5-di(pyridin-4-yl)-1H-indole (Example 74) was prepared following similar experimental conditions used above, using 4-bromo-3-chloroaniline, 4-acetylpyridine as $Ar^2$—$CH_2$—$R^1$ ($R^1$=H; Scheme 5, step i-iii) and pyridin-4-yl boronic acid as $Ar^1$—$B(OH)_2$ (Scheme 7, step i).

tert-butyl 4-chloro-2,5-di(pyridin-4-yl)-1H-indole-1-carboxylate (73.1) and tert-butyl 6-chloro-2,5-di(pyridin-4-yl)-1H-indole-1-carboxylate (74.1)

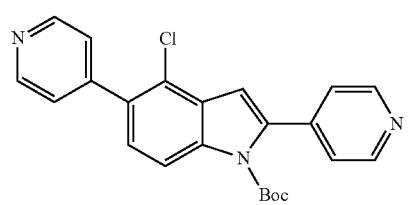
(73.1)

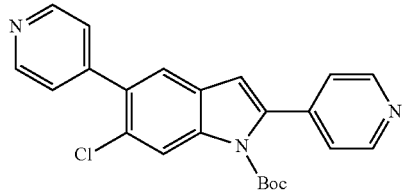
(74.1)

According to Scheme 7, step ii: to a suspension of the above mixture of (73) and (74) (0.7 g, 2.29 mmol) in DMF (10 mL) was added DMAP (56.0 mg, 458 µmol) and Et$_3$N (348 mg, 3.43 mmol, 480 uL) followed by Boc$_2$O (550 mg, 2.52 mmol, 580 uL) at 25° C. Then the mixture was stirred at 25° C. for 12 h. The same experiment was reproduced a second time, and the combined mixture of the two experiments was poured into H$_2$O (20 mL) and extracted with EtOAc (15 mL*3). Then the combined organic layer was washed with brine (15 mL), dried over Na$_2$SO$_4$, filtered and concentrated under reduced pressure to give the residue. The residue was purified by prep-HPLC (neutral condition: column: Agela Durashell C18 150*25 5 u; mobile phase: [water (10 mM NH$_4$HCO$_3$)-ACN]; B %: 50%-80%, 10.5 min and column: Phenomenex Gemini C18 250*50 mm*10 µm; mobile phase: [water (10 mM NH$_4$HCO$_3$)-ACN]; B %: 40%-70%, 23 min) to give desired intermediates. The mixture was further separated by SFC (condition: column: AS (250 mm*30 mm, 10 µm); mobile phase: [0.1% NH$_3$H$_2$O IPA]; B %: 35%-35%, min) to provide compound (73.1) (300 mg, 16% yield) as a gray solid, and compound (74.1) (130 mg, 7% yield) as an off-white solid.

Example 73: 4-chloro-2,5-di(pyridin-4-yl)-1H-indole (73)

According to Scheme 1, Step i: a solution of compound (73.1) (100 mg, 246.38 µmol) in HCl (g)/MeOH (4 M, 3 mL) was stirred at 50° C. for 12 h. The mixture was filtered to collect the precipitate, and the solid was dried in vacuum to give Example 73 (51.2 mg, 55% yield, 100% purity) as a yellow solid: $^1$H NMR (MeOD) δ ppm=8.95 (d, J=5.6 Hz, 2H), 8.85 (d, J=5.6 Hz, 2H), 8.51 (d, J=5.6 Hz, 2H), 8.34 (d, J=5.6 Hz, 2H), 7.87 (s, 1H), 7.73 (d, J=8.4 Hz, 1H), 7.57 (d, J=8.4 Hz, 1H).

Example 74: 6-chloro-2,5-di(pyridin-4-yl)-1H-indole

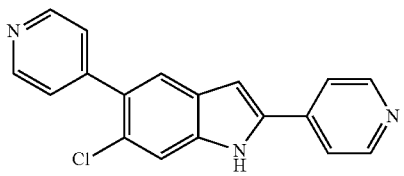

(74)

According to Scheme 1, Step i: a solution of compound (74.1) (100 mg, 246.38 μmol) in HCl (g)/MeOH (4M, 2 mL) was stirred at 25° C. for 2 h. The mixture was filtered to collect the precipitate, and the solid was dried in vacuum to give Example 74 (43.8 mg, yield: 47%, 100% purity) as a yellow solid: $^1$H NMR (MeOD) δ ppm=8.95 (d, J=6.8 Hz, 2H), 8.85 (d, J=7.2 Hz, 2H), 8.47 (d, J=6.8 Hz, 2H), 8.33 (d, J=6.8 Hz, 2H), 8.06 (s, 1H), 7.85 (s, 1H), 7.78 (s, 1H).

Example 75: N,N-dimethyl-4-(2-(2-methylpyridin-4-yl)-1H-indol-5-yl)pyridin-2-amine

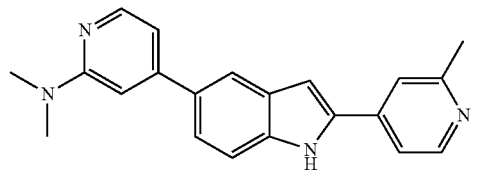

(75)

tert-butyl 5-(2-(dimethylamino)pyridin-4-yl)-2-(2-methylpyridin-4-yl)-1H-indole-1-carboxylate (75.1)

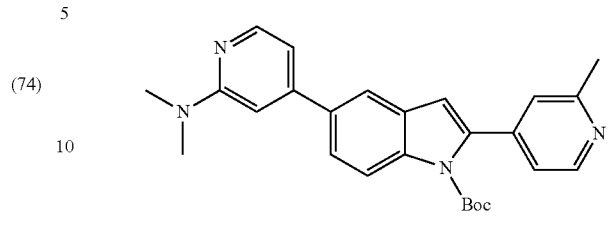

According to Scheme 6, step ii: to a mixture of compound (U7) (0.7 g, 1.61 mmol) and 4-bromo-N,N-dimethylpyridin-2-amine (421 mg, 2.1 mmol) in DMF (20 mL) was added K$_3$PO$_4$ (1.08 g, 5.09 mmol) and Pd(dppf)Cl$_2$·CH$_2$Cl$_2$ (263 mg, 322 μmol) in one portion at 25° C. under N$_2$. The mixture was stirred at 80° C. for 1 hr. The mixture was concentrated under vacuum. The residue was purified by silica gel chromatography (PE:EtOAC=30:1 to 1:1) to provide the desired intermediate (75.1). which was used without further purification.

Example 75: N,N-dimethyl-4-(2-(2-methylpyridin-4-yl)-1H-indol-5-yl)pyridin-2-amine According to Scheme 1, step i: the crude intermediate (75.1) was dissolved in 3 mL MeOH and 3 mL HCl (g)/MeOH (4M). The yellow solid was filtered and collected, dried under vacuum to give Example 75 (33.2 mg, yield: 6, 100% purity) as a yellow solid: $^1$H NMR (D$_2$O) δ ppm=8.23 (d, J=6.4 Hz, 1H), 7.73 (s, 2H), 7.67 (s, 1H), 7.61 (d, J=6.8 Hz, 1H), 7.48 (d, J=9.2 Hz, 1H), 7.33 (d, J=8.4 Hz, 1H), 7.17 (s, 1H), 7.03 (d, J=6.8 Hz, 1H), 6.75 (s, 1H), 3.04 (s, 6H), 2.53 (s, 3H).

The compounds of the invention under Table 7 were prepared according to similar experimental conditions as described for Example 75, starting from intermediate (U7) and reacting with the appropriate Ar$^1$-Hal (Scheme 6, step ii), followed by Boc deprotection (Scheme 1, step i):

TABLE 7

| Ex. | Compound | $^1$H NMR (δ ppm) | Starting material G3, Ar$^1$-Hal |
|---|---|---|---|
| 76 | 5-(6-cyclopropylpyridin-3-yl)-2-(2-methylpyridin-4-yl)-1H-indole | (MeOD) δ = 8.64 (d, J = 2.4, 1H), 8.43 (d, J = 5.2, 1H), 7.95-7.97 (m, 1H), 7.84 (s, 1H), 7.73 (s, 1H), 7.65 (d, J = 5.2, 1H), 7.54-7.56 (m, 1H), 7.48 (s, 1H), 7.28 (d, J = 8.4, 4H), 7.19 (s, 1H), 2.61 (s, 3H), 2.12-2.18 (m, 1H), 0.99-1.08 (m, 4H) | |

TABLE 7-continued

| Ex. | Compound | $^1$H NMR (δ ppm) | Starting material G3, Ar$^1$-Hal |
|---|---|---|---|
| 77 | 5-(6-methoxypyridin-3-yl)-2-(2-methylpyridin-4-yl)-1H-indole | (CDCl$_3$) δ = 8.90 (s, 1H), 8.55 (d, J = 5.2, 1H), 8.44 (d, J = 2.4, 1H), 7.78 (s, 1H), 7.38-7.48 (m, 4H), 7.07 (d, J = 1.2, 1H), 6.84 (d, J = 8.8, 1H), 4.00 (s, 3H), 2.63 (s, 3H) | |
| 78 | 5-(6-(methoxymethyl)pyridin-3-yl)-2-(2-methylpyridin-4-yl)-1H-indole | (MeOD) δ = 8.79 (d, J = 2.0, 1H), 8.42-8.46 (m, 2H), 8.09 (s, 1H), 7.92 (d, J = 1.2, 1H), 7.73 (s, 1H), 7.65 (d, J = 5.2, 1H), 7.58 (d, J = 8.4, 1H), 7.51-7.57 (m, 1H), 7.21 (s, 1H), 4.61 (s, 2H), 3.50 (d, J = 4.0, 3H), 2.61 (s, 3H) | |
| 79 | 5-(5-ethoxypyridin-3-yl)-2-(2-methylpyridin-4-yl)-1H-indole | (MeOD) δ = 8.43 (d, J = 5.2, 2H), 8.16 (d, J = 2.8, 1H), 7.65-7.89 (m, 1H), 7.65 (s, 1H), 7.63-7.64 (m, 2H), 7.56 (s, 1H), 7.51 (d, J = 1.6, 1H), 7.20 (s, 1H), 4.19-4.25 (m, 2H), 2.61 (s, 3H), 1.46-1.49 (m, 3H) | |
| 80 | 5-(5-cyclopropoxypyridin-3-yl)-2-(2-methylpyridin-4-yl)-1H-indole | (MeOD) δ = 8.41-8.43 (m, 3H), 8.39 (s, 1H), 8.24 (d, J = 2.8, 1H), 7.70 (s, 1H), 7.56 (d, J = 1.6, 1H), 7.49-7.53 (m, 1H), 7.48-7.49 (m, 1H), 7.18 (s, 1H), 3.96-4.00 (m, 1H), 2.58 (s, 3H), 0.85-0.90 (m, 2H), 0.76-0.81 (m, 2H) | |
| 81 | 5-(5-(cyclopropyl methoxy)pyridin-3-yl)-2-(2-methyl pyridin-4-yl)-1H-indole | (CDCl$_3$) δ = 8.63 (s, 1H), 8.59 (d, J = 5.6, 1H), 8.54 (d, J = 2.0, 1H), 8.30 (d, J = 2.4, 1H), 7.88 (s, 1H), 7.41-7.56 (m, 5H), 7.11 (d, J = 1.2, 1H), 3.97 (d, J = 7.2, 2H), 2.68 (s, 3H), 1.36 (s, 1H), 0.70-0.74 (m, 2H), 0.42-0.45 (m, 2H) | |

TABLE 7-continued

| Ex. | Compound | $^1$H NMR (δ ppm) | Starting material G3, Ar$^1$-Hal |
|---|---|---|---|
| 82 | 5-(5-cyclopropylpyridin-3-yl)-2-(2-methylpyridin-4-yl)-1H-indole | (MeOD) δ = 8.57 (d, J = 2, 1H), 8.40 (d, J = 5.6, 1H), 8.25 (d, J = 2, 1H), 7.84 (s, 1H), 7.70 (s, 2H), 7.60-7.62 (m, 1H), 7.52-7.54 (m, 1H), 7.44-7.46 (m, 1H), 7.17 (s, 1H), 2.58 (S, 3H), 2.00-2.07 (m, 1H), 1.08-1.10 (m, 2H), 0.83-0.85 (m, 2H) | |
| C83 | 5-(6-(benzyloxy)-5-methoxy pyridin-3-yl)-2-(2-methyl pyridin-4-yl)-1H-indole | (CDCl$_3$) δ = 8.56 (d, J = 5.2 Hz, 2H), 8.00 (d, J = 2 Hz, 1H), 7.80 (s, 1H), 7.53 (d, J = 7.2 Hz, 3H), 7.45 (d, J = 22.4 Hz, 1H), 7.34-7.38 (m, 5H) 7.07 (s, 1H), 5.55 (s, 2H) 3.96 (s, 3H) 2.65 (s, 3H) | |
| 84 | 7-(2-(2-methylpyridin-4-yl)-1H-indol-5-yl)-3,4-dihydro-2H-pyrido[3,2-b][1,4]oxazine | (CDCl$_3$) δ = 8.54 (m, 1H), 7.97 (s, 1H), 7.73 (s, 1H), 7.27-7.46 (m, 5H), 7.03 (s, 1H), 4.84 (s, H 1H), 4.26-4.29 (m, 2H), 3.59 (s, 2H), 2.62 (s, 3H) | |
| 85 | 3-(2-(2-methylpyridin-4-yl)-1H-indol-5-yl)quinolone | (MeOD) δ = 9.22 (d, J = 2.4, 1H), 8.59 (d, J =2.0, 1H), 8.44 (d, J = 5.2, 1H), 8.03-8.08 (m, 3H), 7.74-7.79 (m, 2H), 7.61-7.68 (m, 4H), 7.24 (s, 1H), 2.62 (s, 3H) | |
| 86 | 5-(2-cyclopropoxypyridin-4-yl)-2-(2-methylpyridin-4-yl)-1H-indole | (MeOD) δ = 8.43 (d, J = 5.6 Hz, 1H), 8.16 (d, J = 5.6 Hz, 1H), 7.98 (s, 1H), 7.63 (d, J = 5.2 Hz, 1H), 7.54-7.57 (m, 2H), 7.35-7.36 (m, 1H), 7.24 (s, 1H), 7.20 (s, 1H), 4.15-4.20 (m, 1H), 2.60 (s, 3H), 0.77-0.90 (m, 1H) | |

TABLE 7-continued

| Ex. | Compound | $^1$H NMR (δ ppm) | Starting material G3, Ar$^1$-Hal |
|---|---|---|---|
| 87 | 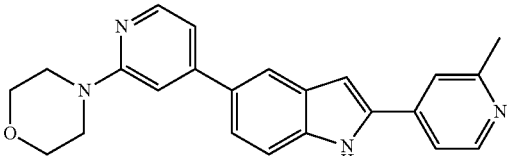<br>4-(4-(2-(2-methylpyridin-4-yl)-1H-indol-5-yl)pyridin-2-yl)morpholine | (D$_2$O) δ = 8.12 (d, J = 6.4 Hz, 1H), 7.69-7.73 (m, 2H), 7.64 (d, J = 4.4 Hz, 1H), 7.56 (s, 1H), 7.30-7.43 (m, 1H), 7.14-7.28 (m, 1H), 7.11-7.13 (m, 2H), 6.97 (s, 1H), 3.78-3.81 (m, 4H), 3.44-3.46 (m, 4H), 2.43 (s, 3H). | 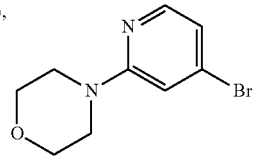 |

The compounds of the invention under Table 7a were prepared according to similar experimental conditions as described above, starting from intermediate (U6) and reacting with the appropriate Ar$^1$-Hal (G3) (Scheme 6, step ii), followed by Boc deprotection (Scheme 1, step i):

TABLE 7a

| Ex. | Compound | $^1$H NMR (δ ppm) or LC-MS RT (min/[MH]$^+$ | Starting material G3, Ar$^1$-Hal |
|---|---|---|---|
| 88 | 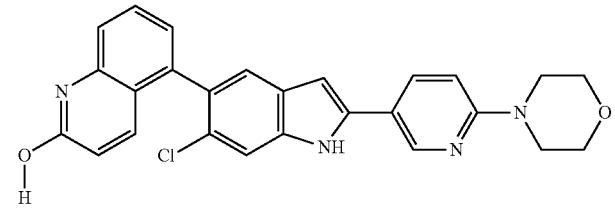<br>5-(6-chloro-2-(6-morpholinopyridin-3-yl)-1H-indol-5-yl)quinolin-2-ol | 11.84 (s, 1H), 11.72 (s, 1H), 8.03 (d, J = 7.6 Hz, 1H), 7.56 (t, J = 18 Hz, 2H), 7.45 (s, 1H), 7.34 (t, J = 22.4 Hz, 2H), 7.08 (d, J = 7.2 Hz, 1H), 6.97 (d, J = 9.2 Hz, 1H), 6.83 (s, 1H), 6.42 (d, J = 10 Hz, 1H), 3.72 (s, 4H), 3.52 (s, 4H) | 5-bromo-2-hydroxyquinoline |
| 89 | 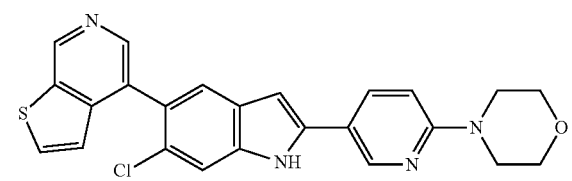<br>4-(5-(6-chloro-5-(thieno[2,3-c]pyridin-4-yl)-1H-indol-2-yl)pyridin-2-yl)morpholine | 11.75 (s, 1H), 9.29 (s, 1H), 8.68 (d, J = 2.0 Hz, 1H), 8.38 (s, 1H), 8.10 (d, J = 5.6 Hz, 1H), 8.02-8.05 (m, 1H), 7.58 (d, J = 2.4 Hz, 2H), 7.13 (d, J = 5.6 Hz, 1H), 6.97 (d, J = 8.8 Hz, 1H), 3.72 (t, J = 9.6 Hz, 4H), 3.53 (t, J = 9.2 Hz, 4H) | 4-bromo-thieno[2,3-c]pyridine |
| 90 | 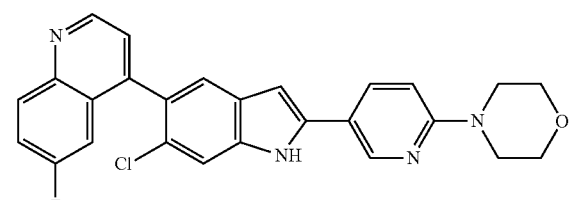<br>4-(5-(6-chloro-5-(6-fluoroquinolin-4-yl)-1H-indol-2-yl)pyridin-2-yl)morpholine | 11.83 (s, 1H), 8.98 (d, J = 4.4 Hz, 1H), 8.69 (d, J = 2.4 Hz, 1H), 8.21 (s, 1H), 8.19 (d, J = 3.6 Hz, 1H), 8.04 (t, J = 11.2 Hz, 1H), 7.60 (s, 1H), 7.56 (s, 1H), 7.52 (d, J = 4.4 Hz, 1H), 7.10 (d, J = 10 Hz, 1H), 6.98 (d, J = 9.6 Hz, 1H), 6.88 (s, 1H), 3.72 (t, J = 9.2 Hz, 4H), 3.53 (d, J = 9.6 Hz, 4H) | 4-bromo-6-fluoroquinoline |

TABLE 7a-continued

| Ex. | Compound | ¹H NMR (δ ppm) or LC-MS RT (min/[MH]⁺ | Starting material G3, Ar¹-Hal |
|---|---|---|---|
| C91 | 4-(5-(6-chloro-5-(5-methoxy-2-methylpyridin-3-yl)-1H-indol-2-yl)pyridin-2-yl)morpholine | 11.60 (s, 1H), 8.66 (d, J = 2.4 Hz, 1H), 8.19 (d, J = 3.2 Hz, 1H), 8.01 (t, J = 11.6 Hz, 1H), 7.49 (s, 1H), 7.41 (s, 1H), 7.15 (d, J = 3.2 Hz, 1H), 6.96 (d, J = 8.8 Hz, 1H), 6.81 (d, J = 1.2 Hz, 1H), 3.81 (s, 3H), 3.71 (t, J = 9.6 Hz, 4H), 3.51 (d, J = 9.6 Hz, 4H), 2.17 (s, 3H) | 3-bromo-5-methoxy-2-methylpyridine |
| 92 | 4-(5-(6-chloro-5-(2-methoxyquinolin-5-yl)-1H-indol-2-yl)pyridin-2-yl)morpholine | 2.46/471.1 | 5-bromo-2-methoxy-quinoline |

Example 93: 4-(5-(6-fluoroquinolin-4-yl)-1H-indol-2-yl)-N,N-dimethylpyridin-2-amine

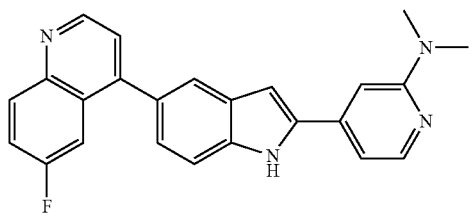 [SMILES: CN(C)c1cc(-c2cc3cc(-c4ccnc5ccc(F)cc45)ccc3[nH]2)ccn1]

93 tert-butyl 2-(2-(dimethylamino)pyridin-4-yl)-5-(6-fluoroquinolin-4-yl)-1H-indole-1-carboxylate (93.1)

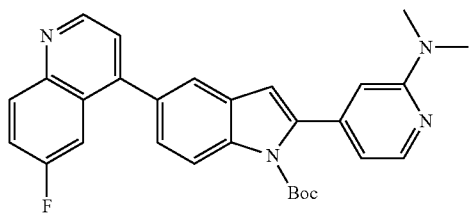 [SMILES: CN(C)c1cc(-c2cc3cc(-c4ccnc5ccc(F)cc45)ccc3n2C(=O)OC(C)(C)C)ccn1]

According to Scheme 6, step ii: A mixture of intermediate (U11) (199 mg, 430 μmol), 4-bromo-6-fluoroquinoline (81.0 mg, 358 μmol), K₂CO₃ (149 mg, 1.08 mmol), Pd(dppf)Cl₂·CH₂Cl₂ (29.3 mg, 35.8 μmol) in dioxane/H₂O (10/1) (5.00 mL) was degassed and purged with N₂ for 3 times, and then the mixture was stirred at 80° C. for 12 hrs under N₂ atmosphere. The reaction mixture was filtered and concentrated under reduced pressure to give a residue. The residue was purified by prep-TLC (SiO₂, PE/EtOAc=1/1) to intermediate (93.1) (171 mg, 98.9% yield) as a yellow solid. ¹HNMR (CDCl₃): δ ppm 8.92 (s, 1H), 8.37 (d, J=8.4 Hz, 1H), 8.21 (s, 2H), 7.69 (s, 1H), 7.60 (d, J=10 Hz, 1H), 7.50 (d, J=5.6 Hz, 1H), 7.48 (t, J=8.8 Hz, 2H), 7.43 (d, J=4.4 Hz, 2H), 6.72 (s, 1H), 6.63 (t, J=11.2 Hz, 2H), 3.15 (s, 6H), 1.43 (s, 9H).

Example 93: 4-(5-(6-fluoroquinolin-4-yl)-1H-indol-2-yl)-N,N-dimethylpyridin-2-amine According to Scheme 1, step i: A mixture of intermediate (93.1) (171 mg, 354 μmol) in HCl/MeOH (3.00 mL) was degassed and purged with N₂ for 3 times, and then the mixture was stirred at 25° C. for 3 hrs under N₂ atmosphere. The reaction mixture was concentrated under reduced pressure to give a residue. The residue was purified by prep-HPLC (column: Xtimate C18 150*25 mm*5 μm; mobile phase: [water (10 mM NH₄HCO₃)-ACN]; B %: 52%-82%, 10.5 min) to give Example 93 (59.2 mg, 43.4% yield, 99.4% purity) as a yellow solid: ¹H NMR (CDCl₃) δ ppm=8.93 (s, 1H), 8.92 (s, 1H), 8.26 (d, J=5.2 Hz, 1H), 8.19 (d, J=5.2 Hz, 1H), 7.78 (s, 1H), 7.68 (s, 1H), 7.58 (d, J=8.4 Hz, 1H), 7.44 (d, J=4.4 Hz, 1H), 7.37 (d, J=1.6 Hz, 1H), 7.35 (s, 1H), 7.05 (s, 1H), 6.87 (d, J=5.2 Hz, 4H), 6.79 (s, 1H), 3.19 (s, 6H).

The following compounds of the invention under Table 8 were prepared according to similar experimental conditions as described above, starting from compound (U11) and reacting with Ar¹-Hal of formula (G3) (Scheme 6, step ii), followed by Boc deprotection (Scheme 1, step i):

TABLE 8

| Ex. | Compound | $^1$H NMR | Ar$^1$-Hal (G3) |
|---|---|---|---|
| 94 | 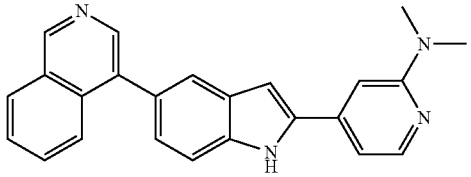 4-(5-(isoquinolin-4-yl)-1H-indol-2-yl)-N,N-dimethylpyridin-2-amine | (DMSO-d$_6$) δ ppm = 11.88 (s, 1H), 9.32 (s, 1H), 8.48 (s, 1H), 8.21 (s, 1H), 8.13 (d, J = 5.2 Hz, 1H), 7.95 (d, J = 8 Hz, 1H), 7.72 (s, 3H), 7.61 (d, J = 8.4 Hz, 1H), 7.32 (d, J = 8.4 Hz, 1H), 7.20 (s, 1H), 7.13 (s, 1H), 7.07 (d, J = 5.6 Hz, 1H), 3.12 (s, 6H). | 4-bromo-isoquinoline |
| 95 | 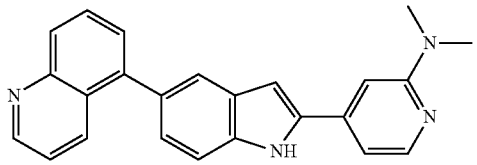 N,N-dimethyl-4-(5-(quinolin-5-yl)-1H-indol-2-yl)pyridin-2-amine | — | 5-bromo-quinoline |

Example 96:
3-chloro-2,5-di(pyridin-4-yl)-1H-indole

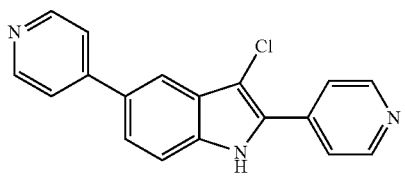

(96)

5-bromo-3-chloro-2-(pyridin-4-yl)-1H-indole (96.1)

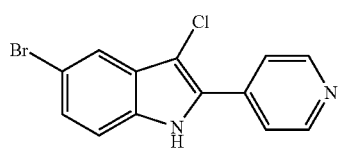 [SMILES: Clc1c(-c2ccncc2)[nH]c2ccc(Br)cc12]

According to Scheme 8, step i: to a solution of compound (U8) (200 mg, 732 μmol) in DMF (1 mL) was added NCS (98 mg, 732 μmol) at 25° C. Then the mixture was stirred at 25° C. for 12 h. The mixture was poured into H$_2$O (5 mL), the aqueous was extracted with EtOAc (5 mL×2). The combined organic layer was washed with brine (5 mL), dried over Na$_2$SO$_4$, filtered and concentrated under reduced pressure to give intermediate (96.1) (200 mg, yield: 89%) as an orange solid, which was used into the next step without further purification.

Example 96:
3-chloro-2,5-di(pyridin-4-yl)-1H-indole

According to Scheme 8, step ii: to a solution of compound (96.1) (200 mg, 650 μmol) in dioxane (2 mL) was added pyridine-4-yl boronic acid (88.0 mg, 715 μmol) followed by a solution of Na$_2$CO$_3$ (103 mg, 975 μmol, 1.5 eq) in H$_2$O (1 mL). Then the mixture was degassed, treated with Pd(dppf)Cl$_2$ (48.0 mg, 65.0 μmol) at 25° C. under N$_2$. Then the resulted mixture was stirred at 100° C. for 12 h. The mixture was poured into H$_2$O (10 mL), the aqueous was extracted with EtOAc (10 mL×2). The combined organic layer was washed with brine (10 mL), dried over Na$_2$SO$_4$, filtered and concentrated under reduced pressure to give the residue. The residue was purified by prep-HPLC (neutral condition: column: Agela Durashell C18 150*25 5 u; mobile phase: [water (10 mM NH$_4$HCO$_3$)-ACN]; B %: 40%-60%, 10.5 min) to give Example 96 (7.0 mg, yield: 3%, 95.41% purity) as a gray solid. $^1$H NMR (DMSO-d$_6$) δ ppm 6=8.75 (d, J=4.4 Hz, 2H), 8.63 (d, J=4.4 Hz, 2H), 7.98 (s, 1H), 7.95 (d, J=4.8 Hz, 2H), 7.79 (d, J=5.2 Hz, 2H), 7.74 (d, J=9.2 Hz, 1H), 7.62 (d, J=8.8 Hz, 1H).

Example 97: 2-(2-methylpyridin-4-yl)-5-(pyridin-4-yl)-1H-indole

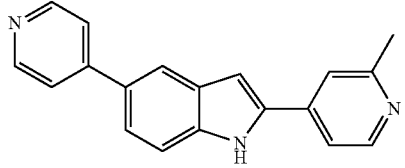

(97)

2-(2-methylpyridin-4-yl)-1-(methylsulfonyl)-5-(pyridin-4-yl)-1H-indole (97.1)

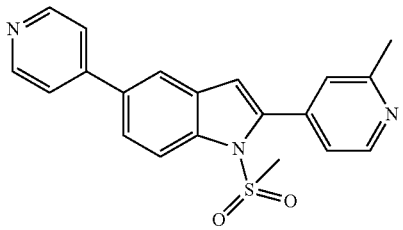 [SMILES: Cc1cc(-c2cc3cc(-c4ccncc4)ccc3n2S(C)(=O)=O)ccn1]

According to Scheme 4, step v and vi (one-pot procedure): to a solution of intermediate (U9) (0.2 g, 0.56 mmol, 1 eq.) in DME (2.5 mL) was added 2M aqueous sodium carbonate (0.85 mL, 1.7 mmol, 3 eq.), 2-methylpyridine-4-boronic acid (0.078 g, 5.67 mmol, 1 eq.) and Pd(dppf)Cl$_2$.DCM (0.023 g, 0.028 mmol, 0.05 eq.) and the reaction mixture heated to 90° C. in a microwave for 1 hour. Pyridine-4-boronic acid (0.084 g, 0.68 mmol, 1.2 eq.) and Pd(dppf)Cl$_2$.DCM (0.023 g, 0.028 mmol, 0.05 eq.) were added and the reaction mixture heated to 100° C. in a microwave for 1 hour. EtOAc (30 mL) and water (10 mL) were added and the mixture filtered through celite. The organic layer was separated and washed with brine (10 mL) before being passed through a phase separation cartridge and the solvent removed in vacuo. The residue was purified by silica gel column chromatography using 5% methanol in dichloromethane to afford intermediate (97.1) (0.116 g, 56% yield). $^1$HNMR (CDCl$_3$): δ ppm. 70 (2H, dd, J=1.8, 4.3 Hz), 8.58 (1H, d, J=5.1 Hz), 8.23 (1H, d, J=8.8 Hz), 7.91-7.88 (1H, m), 7.71 (1H, ddd, J=1.9, 4.1, 8.7 Hz), 7.58-7.56 (2H, m), 7.55-7.49 (1H, m), 7.38-7.36 (1H, m), 7.33-7.30 (1H, m), 2.82 (3H, s), 2.65 (3H, s).

Example 97: 2-(2-methylpyridin-4-yl)-5-(pyridin-4-yl)-1H-indole

According to Scheme 4, step vii: To a solution of compound (97.1) (0.11 g, 0.3 mmol 1 eq.) in dioxane (5 mL) was added 2M NaOH solution (0.6 mL, 1.21 mmol, 4 eq.) and the reaction heated to 100° C. for 1 hour. The solvent was removed in vacuo and water (7 mL) added and the pH was adjusted to 5 using 2M HCl. The solid was filtered off, washed with water and dried in vacuo to afford Example 97 (0.018 g, 21% yield). $^1$H NMR (DMSO-d$_6$) δ ppm 11.97-11.97 (1H, m), 8.61 (2H, d, J=6.1 Hz), 8.51 (1H, d, J=5.3 Hz), 8.07 (1H, d, J=1.1 Hz), 7.77-7.73 (3H, m), 7.67 (1H, dd, J=1.4, 5.2 Hz), 7.63 (1H, dd, J=1.8, 8.5 Hz), 7.57 (1H, d, J=8.5 Hz), 7.27 (1H, s), 2.55 (3H, s).

The compounds of the invention under Table 8 were prepared according to similar experimental conditions as described above, starting from intermediate (U9) and the appropriate boronic acids Ar$^2$—B(OH)$_2$ and Ar$^1$—B(OR)$_2$ (Scheme 4, step v-vi), followed by methylsulfonyl deprotection (Scheme 4, step vii):

TABLE 8

| Ex. | Compound | $^1$H NMR (δ ppm) | G1 (Ar$^1$-B(OR)$_2$) and G3 (Ar$^2$-B(OH)$_2$) |
|---|---|---|---|
| 98 | 5-(5-methoxypyridin-3-yl)-2-(2-methylpyridin-4-yl)-1H-indole | (DMSO-d$_6$) δ = 11.97-11.97 (1H, m), 8.61 (2H, d, J = 6.1 Hz), 8.51 (1H, d, J = 5.3 Hz), 8.07 (1H, d, J = 1.1 Hz), 7.77-7.73 (3H, m), 7.67 (1H, dd, J = 1.4, 5.2 Hz), 7.63 (1H, dd, J = 1.8, 8.5 Hz), 7.57 (1H, d, J = 8.5 Hz), 7.27 (1H, s), 2.55 (3H, s) | 5-methoxypyridine-3-boronic acid and 2-methylpyridine-4-boronic acid |
| 99 | 5-(5-methoxypyridin-3-yl)-2-(pyridin-4-yl)-1H-indole | (DMSO-d$_6$) δ = 11.92 (1H, s), 8.53-8.49 (2H, m), 8.26-8.22 (1H, m), 7.97 (1H, s), 7.76 (1H, s), 7.67 (1H, dd, J = 1.4, 5.3 Hz), 7.64 (1H, dd, J = 1.9, 2.7 Hz), 7.56 (2H, s), 7.24 (1H, d, J = 2.1 Hz), 3.93 (3H, s), 2.55 (3H, s) | 5-methoxypyridine-3-boronic acid and pyridine-4-boronic acid |
| 100 | 5-(5-methoxypyridin-3-yl)-2-(pyridin-3-yl)-1H-indole | (DMSO-d$_6$) δ = 12.10-12.10 (1H, m), 8.71 (2H, d, J = 5.1 Hz), 8.63 (2H, d, J = 5.4 Hz), 7.91 (2H, d, J = 5.4 Hz), 7.76 (2H, d, J = 5.3 Hz), 7.57 (1H, d, J = 7.8 Hz), 7.43 (1H, s), 7.36-7.26 (2H, m) | 5-methoxypyridine-3-boronic acid and pyridine-3-boronic acid |

TABLE 8-continued

| Ex. | Compound | $^1$H NMR (δ ppm) | G1 (Ar$^1$-B(OR)$_2$) and G3 (Ar$^2$-B(OH)$_2$) |
|---|---|---|---|
| 101 | 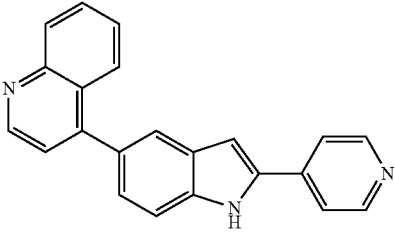<br>4-(2-(pyridin-4-yl)-1H-indol-5-yl)quinoline | (DMSO-d$_6$) δ = 11.85 (1H, s), 9.15 (1H, s), 8.55-8.51 (2H, m), 8.29-8.24 (2H, m), 7.95 (1H, s), 7.64 (1H, dd, J = 2.2, 2.2 Hz), 7.55-7.49 (3H, m), 7.14 (1H, s), 3.94 (3H, s) | quinolone-4-boronic acid and pyridine-4-boronic acid |
| 102 | 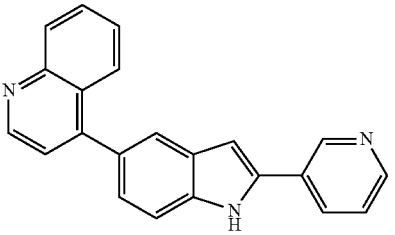<br>4-(2-(pyridin-3-yl)-1H-indol-5-yl)quinoline | (DMSO-d$_6$) δ = 12.07 (1H, s), 8.95 (1H, d, J = 4.5 Hz), 8.66 (2H, d, J = 6.1 Hz), 8.16 (2H, s), 8.12 (1H, d, J = 8.2 Hz), 8.02 (1H, d, J = 8.2 Hz), 7.89 (2H, d, J = 6.1 Hz), 7.83-7.76 (2H, m), 7.65 (1H, d, J = 8.4 Hz), 7.60 (1H, ddd, J = 1.3, 6.9, 8.3 Hz), 7.52 (1H, d, J = 4.4 Hz), 7.38 (1H, dd, J = 1.6, 8.4 Hz), 7.33 (1H, d, J = 1.4 Hz) | quinoline-4-boronic acid and pyridine-3-boronic acid |
| 103 | 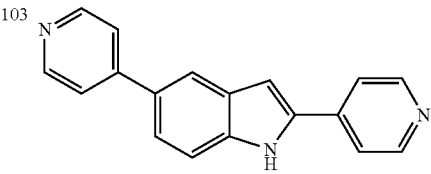<br>2,5-di(pyridin-4-yl)-1H-indole | (DMSO-d$_6$) δ = 11.96 (1H, s), 9.17 (1H, d, J = 1.9 Hz), 8.95 (1H, d, J = 4.4 Hz), 8.55 (1H, dd, J = 1.4, 4.6 Hz), 8.29 (1H, d, J = 8.2 Hz), 8.12 (1H, d, J = 8.2 Hz), 8.03 (1H, d, J = 8.0 Hz), 7.80 (1H, d, J = 6.9 Hz), 7.77 (1H, s), 7.62 (2H, dd, J = 7.7, 14.5 Hz), 7.56-7.50 (2H, m), 7.34 (1H, dd, J = 1.6, 8.4 Hz), 7.18 (1H, s) | pyridine-4-boronic acid and pyridine-4-boronic acid |
| 104 | 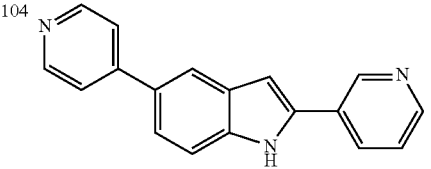<br>2-(pyridin-3-yl)-5-(pyridin-4-yl)-1H-indole | (DMSO-d$_6$) δ = 12.01-12.01 (1H, m), 8.65 (2H, d, J = 6.1 Hz), 8.62-8.60 (2H, m), 8.08 (1H, d, J = 1.3 Hz), 7.88-7.86 (2H, m), 7.76-7.74 (2H, m), 7.65 (1H, dd, J = 1.8, 8.7 Hz), 7.58 (1H, d, J = 8.5 Hz), 7.31 (1H, s) | pyridine-4-boronic acid and pyridine-3-boronic acid |
| 105 | 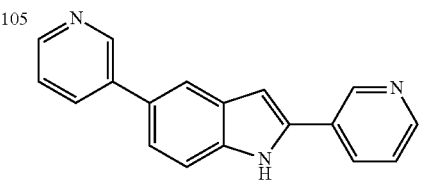<br>2,5-di(pyridin-3-yl)-1H-indole | (DMSO-d$_6$) δ = 11.94 (1H, s), 9.15 (1H, d, J = 2.0 Hz), 8.60 (2H, d, J = 6.1 Hz), 8.54 (1H, dd, J = 1.5, 4.8 Hz), 8.29-8.25 (1H, m), 8.05 (1H, s), 7.76-7.74 (2H, m), 7.61 (1H, dd, J = 1.7, 8.5 Hz), 7.56 (1H, d, J = 8.5 Hz), 7.52 (1H, ddt, J = 0.7, 4.3, 4.0 Hz), 7.16 (1H, d, J = 1.5 Hz) | pyridine-3-boronic acid and pyridine-3-boronic acid |

TABLE 8-continued

| Ex. | Compound | ¹H NMR (δ ppm) | G1 (Ar¹-B(OR)₂) and G3 (Ar²-B(OH)₂) |
|---|---|---|---|
| 106 | 2-(1-methyl-1H-pyrazol-5-yl)-5-(pyridin-4-yl)-1H-indole | (DMSO-d₆) δ = 11.89 (1H, s), 9.15 (1H, d, J = 1.9 Hz), 8.93 (1H, d, J = 2.0 Hz), 8.53 (2H, d, J = 4.6 Hz), 8.29-8.25 (1H, m), 8.12-8.08 (1H, m), 7.92 (1H, s), 7.58-7.46 (4H, m), 7.14 (1H, d, J = 1.5 Hz) | pyridine-4-boronic acid and (2-methylpyrazol-3-yl)boronic acid |
| 107 | 5-(2-(4-methylpiperazin-1-yl)pyridin-4-yl)-2-(pyridin-4-yl)-1H-indole | (DMSO-d₆) δ = 11.78 (1H, s), 8.61 (2H, d, J = 6.0 Hz), 8.31 (1H, d, J = 8.0 Hz), 8.15-8.09 (3H, m), 7.76 (2H, d, J = 6.1 Hz), 7.62 (1H, dd, J = 1.6, 8.4 Hz), 7.59-7.54 (2H, m), 7.50 (1H, dd, J = 7.4, 7.4 Hz), 7.05 (1H, s) | 2-(4-methylpiperazino)-pyridine-4-boronic acid and pyridine-4-boronic acid pinacol ester |

Example 108: 5-(5-methoxypyridin-3-yl)-2-(pyridin-2-yl)-1H-indole

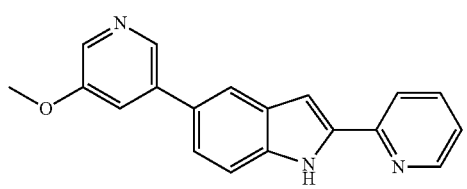

(108)

4-(5-methoxypyridin-3-yl)aniline (108.1)

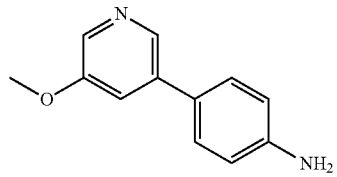

According to Scheme 9, step i: to a solution of (5-methoxypyridin-3-yl)boronic acid (15 g, 98 mmol) in dioxane (100 mL) was added 4-bromo aniline (25.3 g, 147 mmol), then a solution of Na₂CO₃ (20.8 g, 196 mmol) in H₂O (20 mL) was added, the reaction mixture was degassed and purged with N₂ for 3 times. Then Pd(dppf)Cl₂ (7.18 g, 9.81 mmol) was added under N₂ and the mixture was stirred at 80° C. for 2 hours. The reaction mixture was concentrated in vacuum to give a residue. The residue was purified by flash chromatography on a silica gel (PE/EtOAc: 30/1 to 1/1) to give compound (108.1) (7 g, yield: 36%) as a yellow solid.

3-(4-hydrazineylphenyl)-5-methoxypyridine (108.2)

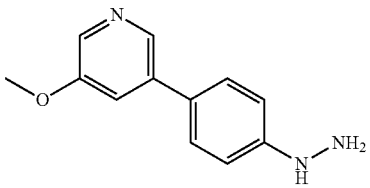 [SMILES: COc1cncc(-c2ccc(NN)cc2)c1]

According to Scheme 9, step ii: a solution of compound (108.1) (7.8 g, 38.9 mmol) in conc. HCl (50 mL) was cooled to 0° C., then a solution of NaNO₂ (5.38 g, 77.9 mmol) in H₂O (20 mL) was added dropwise at 0° C. and stirred at 0° C. for 30 minutes. A solution of SnCl₂.2H₂O (26.4 g, 117 mmol) in conc. HCl (40 mL) was added dropwise and stirred at 0° C. for 4 hours. The reaction mixture was adjusted to pH=14 with NaOH (12 M), and then extracted with EtOAc (20 mL×3). The organic phase was combined and concentrated in vacuum to give compound (108.2) (5 g, crude) as a yellow solid, which was used without further purification in the next step.

(E)-3-methoxy-5-(4-(2-(1-(pyridin-2-yl)ethylidene)hydrazineyl)phenyl)pyridine (108.3)

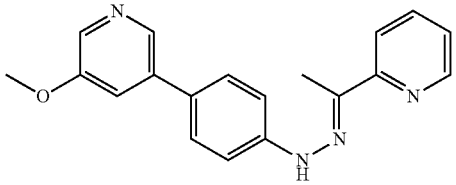 [SMILES: COc1cncc(-c2ccc(N/N=C(\C)c3ccccn3)cc2)c1]

According to Scheme 9, step iii: A mixture of intermediate (108.2) (0.2 g, 929 μmol) and 1-(pyridin-2-yl)ethan-1-one (112 mg, 929 μmol, 104 uL) in toluene (2 mL) was stirred at 80° C. for 12 hours. The reaction mixture was concentrated in vacuum to give a residue. The residue was purified by prep-TLC (PE:EtOAc=0:1) to give compound (108.3) (0.12 g, yield: 41%) as a yellow solid. $^1$H NMR (MeOD) δ ppm=8.50 (s, 1H), 8.37 (s, 1H), 8.20 (d, J=8 Hz, 1H), 8.13 (d, J=2.8 Hz, 1H), 7.75-7.79 (m, 1H), 7.58-7.61 (m, 2H), 7.40-7.43 (m, 2H), 7.28-7.29 (m, 1H), 3.96 (s, 3H), 2.39 (s, 3H).

Example 108: 5-(5-methoxypyridin-3-yl)-2-(pyridin-2-yl)-1H-indole

According to Scheme 9, step iv: a mixture of compound (108.3) (0.05 g, 157 μmol) in toluene (0.5 mL) was added to PPA (0.5 g, 157 μmol) at 100° C. and stirred at 100° C. for 12 hours. The reaction mixture was adjusted to pH=8 with sat. Na$_2$CO$_3$, and extracted with EtOAc (5 mL×3). The organic phase was combined and concentrated in vacuum to give a residue. The residue was dealed with HCl (g)/EtOAc (5 mL, 4M) and filtered, the filter cake was washed with EtOAc (2 mL) and dried to give Example 108 (53.1 mg, 88.5% purity, yield: 80%, 2HCl) as a brown solid. $^1$H NMR (DMSO-d$_6$) δ=12.12 (s, 1H), 8.85 (s, 1H), 8.68-8.69 (m, 1H), 8.56 (s, H), 8.37 (s, 1H), 8.15-8.18 (m, 2H), 7.99-8.01 (m, 1H), 7.64-7.67 (m, 1H), 7.62-7.64 (m, 1H), 7.41-7.43 (m, 1H), 7.38 (s, 1H), 4.07 (s, 3H).

The compounds of the invention under Table 9 were prepared according to similar experimental conditions described for Example 108, starting from Intermediate (108.1) and reacting with ketone Ar$^2$—CO-Me (Scheme 9, step iii), followed by cyclisatino using Eaton's reagent (Scheme 9, step iv):

TABLE 9

| Ex. | Compound | $^1$H NMR (δ ppm) | ketone |
|---|---|---|---|
| 109 | -2-(pyrimidin-4-yl)-1H-indole) 5-(5-methoxypyridin-3-yl)-2-(pyrimidin-4-yl)-1H-indole | (DMSO-d$_6$) δ = 12.11 (s, 1H), 9.22 (s, 1H), 8.83 (d, J = 5.2 Hz, 1H), 8.62 (s, H), 8.34 (d, J = 2.0 Hz, 1H), 8.07-8.10 (m, 2H), 7.84 (s, 1H), 7.62 (s, 2H), 7.52 (s, 1H), 3.96 (s, 3H) | |
| 110 | -5-(5-methoxypyridin-3-yl)-1H-indole) 2-(3-fluoropyridin-4-yl)-5-(5-methoxypyridin-3-yl)-1H-indole | (DMSO-d$_6$) δ = 11.91 (s, 1H), 8.69 (d, J = 3.2 Hz, 1H), 8.52-8.54 (m, 2H), 8.25 (d, J = 2.8 Hz, 1H), 8.04 (s, 1H), 7.95-7.98 (m, 1H), 7.63 (s, 1H), 7.61 (s, 2H), 7.25 (s, 1H), 3.92 (s, 3H) | |

Example 111: 1-isopropyl-5-(5-methoxypyridin-3-yl)-2-(2-methylpyridin-4-yl)-1H-indole

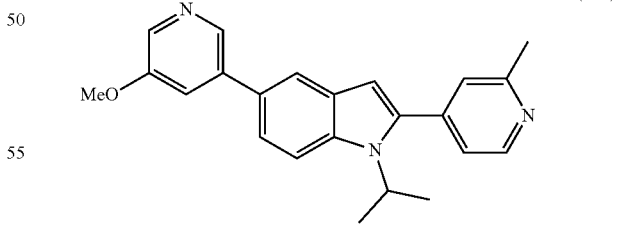

(111)

According to Scheme 10, step ia: a solution of Example 98 (400 mg, 1.27 mmol), isopropyl bromide (468 mg, 3.81 mmol) and Cs$_2$CO$_3$ (1.24 g, 3.81 mmol) were taken up into a microwave tube in ACN (3 mL). The sealed tube was heated at 80° C. for 3 hr under microwave. The reaction mixture was washed with MeOH (0.5 mL×3), filtered and concentrated under reduced pressure to give a residue. The residue was purified by prep-HPLC (TFA column: Luna C18

100*30 5 u; mobile phase: [water (0.1% TFA)-ACN]; B %: 20%-25%, 10 min) to afford Example 111 (21.1 mg, 42.7 μmol, yield: 3%, 95.3% purity) as a yellow solid: $^1$H NMR (DMSO-d6) δ ppm=8.77 (d, J=6.0 Hz, 1H), 8.64 (d, J=1.6 Hz, 1H), 8.36 (d, J=2.8 Hz, 1H), 8.10 (s, 1H), 7.91 (t, J=19.6 Hz, 1H), 7.87 (s, 1H), 7.82 (s, 1H), 7.60 (d, J=32 Hz, 1H), 7.66 (d, J=46.8 Hz, 1H), 6.95 (s, 1H), 4.70 (t, J=14 Hz, 1H), 3.97 (d, J=6.8 Hz, 3H), 2.74 (d, J=10.8 Hz, 3H), 1.64 (d, J=6.8 Hz, 6H).

The compound of the invention under Table 10 was prepared according to similar experimental conditions, starting from Example 72, reacting with the appropriate halide R$^1$-Hal (Scheme 10, step ia):

TABLE 10

| Ex. | Compound | $^1$H NMR (δ ppm) | Halide R$^1$-Hal |
|---|---|---|---|
| 112 | 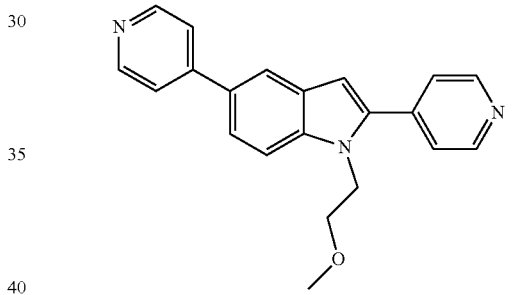<br>4-(5-(6-chloro-5-(5-methoxypyridin-3-yl)-1-methyl-1H-indol-2-yl)pyridin-2-yl)morpholine | 8.37 (d, J = 2.4 Hz, 1H), 8.30 (d, J = 2.4 Hz, 1H), 8.23 (s, 1H), 7.82 (d, J = 2.4 Hz, 1H), 7.79 (t, J = 8.0 Hz, 1H), 7.62 (s, 1H), 7.43 (s, 1H), 6.97 (d, J = 8.8 Hz, 1H), 6.59 (s, 1H), 3.88 (s, 3H), 3.76 (s, 3H), 3.72 (t, J = 9.6 Hz, 4H), 3.54 (t, J = 10 Hz, 4H) | Methyl iodide |

Example 113: 1-(2-methoxyethyl)-2,5-di(pyridin-4-yl)-1H-indole (113)

Example 113 was prepared according to similar experimental conditions used as described above, starting from Example 103 and reacting with 2-bromoethyl methyl ether (Scheme 10, step ia). $^1$HNMR (CDCl$_3$): δ ppm δ=8.73 (2H, d, J=6.0 Hz), 8.65 (2H, d, J=6.0 Hz), 7.95 (1H, s), 7.61-7.52 (6H, m), 6.75 (1H, s), 4.41 (2H, dd, J=5.7, 5.7 Hz), 3.71 (2H, dd, J=5.7, 5.7 Hz), 3.24 (3H, s).

Example 114: 1-(2-methoxyethyl)-5-(5-methoxypyridin-3-yl)-2-(2-methylpyridin-4-yl)-1H-indole

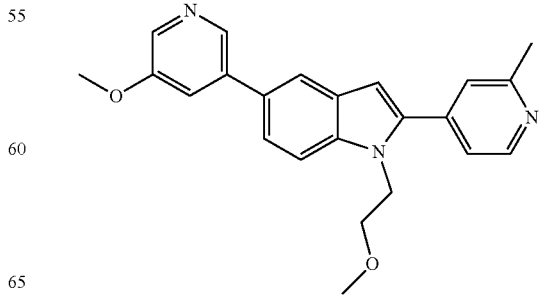

(114)

5-bromo-1-(2-methoxyethyl)-2-(2-methylpyridin-4-yl)-1H-indole (114.1)

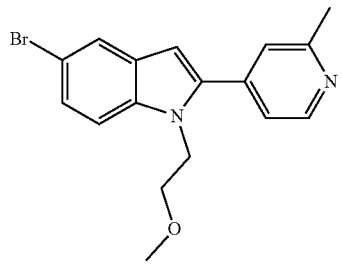 [SMILES: COCCn1c(-c2ccnc(C)c2)cc2cc(Br)ccc21]

According to Scheme 11, step ia: to a solution of intermediate (U1) (250 mg, 871 μmol) in DMF (1.00 mL) was added NaH (34.8 mg, 871 μmol, 60% purity) at 0° C. After addition, the mixture was stirred at this temperature for 30 mins, and then 2-bromoethyl methyl ether (121 mg, 871 μmol, 81.8 uL) was added at 0° C. The resulting mixture was stirred at 20° C. for 12 hrs. After 12 h, 2-bromoethyl methyl ether (60.5 mg, 435 μmol, 40.9 uL) was added, and then stirred at 20° C. for 2 hrs. After 2 h, NaH (34.8 mg, 60% purity) was added, and then stirred at 50° C. for 12 hrs. The reaction mixture was washed with MeOH (2.00 mL×3), filtered and concentrated under reduced pressure to give a residue. The residue was purified by prep-TLC (SiO$_2$, Petroleum ether/Ethyl acetate=3/1) to give compound (114.1) (280 mg, 93.2% yield) as a yellow solid. $^1$HNMR (CDCl$_3$): δ ppm 8.59 (d, J=5.2 Hz, 1H), 8.77 (d, J=1.6 Hz, 1H), 7.34-7.36 (m, 3H), 7.31 (t, J=16.8 Hz, 3H), 6.58 (s, 1H), 4.33 (t, J=11.2 Hz, 2H), 3.64 (t, J=11.6 Hz, 2H), 3.22 (s, 3H), 2.64 (s, 3H).

Example 114: 1-(2-methoxyethyl)-5-(5-methoxypyridin-3-yl)-2-(2-methylpyridin-4-yl)-1H-indole According to Scheme 11, step ii: a mixture of compound (114.1) (290 mg, 840 μmol), (5-methoxypyridin-3-yl)boronic acid (128 mg, 840 μmol), Cs$_2$CO$_3$ (547 mg, 1.68 mmol), Pd(dppf)Cl$_2$·CH$_2$Cl$_2$ (68.6 mg, 84.0 μmol) in dioxane (3.00 ML) and H$_2$O (0.300 mL) was degassed and purged with N$_2$ for 3 times, and then the mixture was stirred at 120° C. for 12 hrs under N$_2$ atmosphere. The reaction mixture was washed with MeOH (2.00 mL×3), filtered and concentrated under reduced pressure to give a residue. The residue was purified by prep-TLC (SiO$_2$, PE:EtOAc=0/1), Followed by prep-HPLC (HCl column: Waters Xbridge 150*25 5 u; mobile phase: [water (0.05% HCl)-ACN]; B %: 1%-20%, 12 min) to give compound Example 114 (87.2 mg, 25.3% yield, 100% purity) as a yellow solid: $^1$H NMR (CDCl$_3$) δ pm=8.65 (d, J=8 Hz, 2H), 8.31 (d, J=2.4 Hz, 1H), 7.96-8.05 (m, 4H), 7.57-7.62 (m, 2H), 7.04 (s, 1H), 4.45 (t, J=9.2 Hz, 2H), 4.08 (s, 3H), 3.85-3.89 (m, 2H), 3.29 (s, 3H), 3.04 (s, 3H).

The compound of the invention under Table 12 were prepared according to similar experimental conditions, starting from intermediate (U1), reacting with the appropriate halide R$^1$-Hal (Scheme 11, step ia), followed by the reaction with (5-methoxypyridin-3-yl)boronic acid (Scheme 11, step ii):

TABLE 12

| Ex. | Compound | $^1$H NMR (δ ppm) | Halide R$^1$-Hal |
|---|---|---|---|
| 115 | 1-methyl-5-(5-methoxypyridin-3-yl)-2-(2-methylpyridin-4-yl)-1H-indole | (MeOD) δ = 8.44 (d, J = 5.2 Hz, 1H), 8.23 (s, 1H), 7.74 (s, 1H), 7.66 (d, J = 5.6 Hz, 1H), 7.52 (t, J = 4.4 Hz, 1H), 7.49 (d, J = 8.4 Hz, 1H), 7.26 (s, 1H), 7.23 (d, J = 8.4 Hz, 1H), 4.58 (s, 1H), 3.92 (d, J = 4.4 Hz, 3H), 2.60 (s, 3H). | Methyl iodide |
| 116 | 1-ethyl-5-(5-methoxypyridin-3-yl)-2-(2-methylpyridin-4-yl)-1H-indole | (CDCl$_3$) δ = 8.61 (d, J = 5.2 Hz, 1H), 8.54 (d, J = 2 Hz, 1H), 8.28 (d, J = 2.8 Hz, 1H), 7.86 (s, 1H), 7.51 (d, J = 1.2 Hz, 1H), 7.45 (d, J = 2 Hz, 1H), 7.44 (s, 1H), 7.32 (s, 1H), 6.71 (s, 1H), 4.26-4.31 (m, 2H), 3.95 (s, 3H), 2.66 (s, 3H) 1.38 (d, J = 14.4 Hz, 3H) | Ethyl bromide |

TABLE 12-continued

| Ex. | Compound | $^1$H NMR (δ ppm) | Halide R$^1$-Hal |
|---|---|---|---|
| 117 | 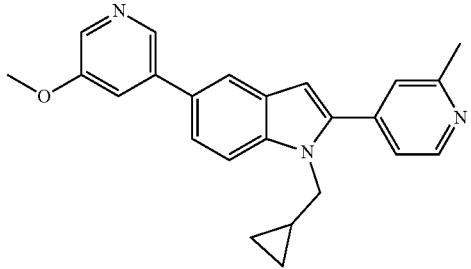<br>1-(cyclopropylmethyl)-5-(5-methoxypyridin-3-yl)-2-(2-methylpyridin-4-yl)-1H-indole | (CDCl$_3$) δ = 8.65 (d, J = 5.2 Hz, 1H), 8.58 (s, 1H), 8.29 (d, J = 2.8 Hz, 1H), 7.91 (s, 1H), 7.71 (s, 1H), 7.55-7.63 (m, 4H), 6.94 (s, 1H), 4.21 (d, J = 6.4 Hz, 2H), 4.01 (s, 3H), 2.91 (s, 3H), 1.05 (s, 1H), 0.51 (d, J = 8.4 Hz, 2H), 0.15 (d, J = 10.8 Hz, 2H) | Cyclopropyl-methyl bromide |
| 118 | 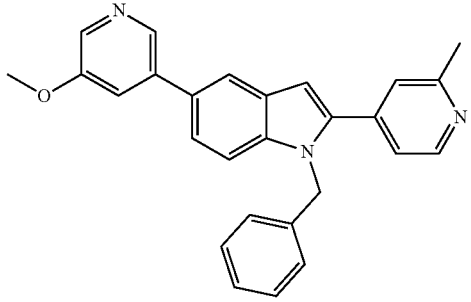<br>1-(benzyl)-5-(5-methoxypyridin-3-yl)-2-(2-methylpyridin-4-yl)-1H-indole | (CDCl$_3$) δ = 8.51-8.53 (m, 2H) 8.28 (d, J = 2.4 Hz, 1H), 7.90 (d, J = 1.2 Hz, 1H), 7.44 (d, J = 2 Hz, 2H), 7.43 (d, J = 3.6 Hz, 2H), 7.32 (d, J = 8 Hz, 2H), 7.30 (s, 1H), 7.23 (s, 1H), 7.06 (d, J = 6.8 Hz, 2H), 6.84 (s, 1H), 5.43 (s, 2H), 3.94 (d, J = 3.2 Hz, 3H), 2.55 (d, J = 7.6 Hz, 3H) | Benzyl bromide |

The compound of the invention under Table 13 were prepared according to similar experimental conditions, starting from a mixture of 7-(5-bromo-4-chloro-1H-indol-2-yl)-3,4-dihydro-2H-pyrido[3,2-b][1,4]oxazine and 7-(5-bromo-6-chloro-1H-indol-2-yl)-3,4-dihydro-2H-pyrido[3,2-b][1,4]oxazine (prepared according to Scheme 4 (step i-iii) from 3-chloro-4-bromo aniline and 1-(3,4-dihydro-2H-pyrido[3,2-b][1,4]oxazin-7-yl)ethan-1-one) reacting with methyl iodide (Scheme 11, step ia), followed by the reaction with (5-methoxypyridin-3-yl)boronic acid (Scheme 11, step ii) and separated by column chromatography:

TABLE 13

| Ex. | Compound | $^1$H NMR (δ ppm) |
|---|---|---|
| 119 | 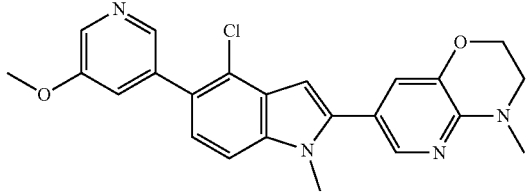<br>7-(4-chloro-5-(5-methoxypyridin-3-yl)-1-methyl-1H-indol-2-yl)-4-methyl-3,4-dihydro-2H-pyrido[3,2-b][1,4]oxazine | 8.31 (d, J = 2.4 Hz, 1H), 8.26 (s, 1H), 7.94 (d, J = 1.6 Hz, 1H), 7.60 (s, 1H), 7.58 (s, 1H), 7.45 (t, J = 4.4 Hz, 1H), 7.23 (t, J = 11.2 Hz, 1H), 6.58 (s, 1H), 4.28 (t, J = 8.8 Hz, 2H), 3.89 (s, 3H), 3.78 (s, 3H), 3.52 (t, J = 8.8 Hz, 2H), 3.10 (s, 3H) |

TABLE 13-continued

| Ex. | Compound | $^1$H NMR (δ ppm) |
|---|---|---|
| 120 | 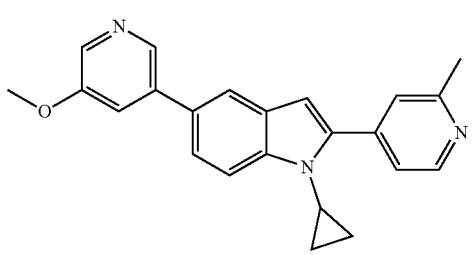<br>7-(6-chloro-5-(5-methoxypyridin-3-yl)-1-methyl-1H-indol-2-yl)-4-methyl-3,4-dihydro-2H-pyrido[3,2-b][1,4]oxazine | 8.30 (s, 1H), 8.23 (s, 1H), 7.91 (s, 1H), 7.76 (s, 1H), 7.60 (s, 1H), 7.42 (s, 1H), 7.18 (s, 1H), 6.65 (s, 1H), 4.27 (s, 2H), 3.88 (s, 3H), 3.75 (s, 3H), 3.51 (s, 2H), 3.09 (s, 3H) |

Example 121: 1-cyclopropyl-5-(5-methoxypyridin-3-yl)-2-(2-methylpyridin-4-yl)-1H-indole

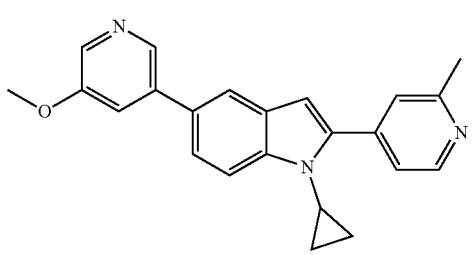

(121)

5-bromo-1-cyclopropyl-2-(2-methylpyridin-4-yl)-1H-indole (121.1)

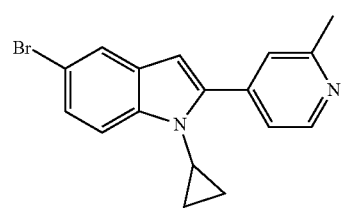 [SMILES: Cc1cc(-c2cc3cc(Br)ccc3n2C2CC2)ccn1]

According to Scheme 11, step ib: a mixture of intermediate (U1) (400 mg, 1.39 mmol), cyclopropyl boronic acid (479 mg, 5.57 mmol), Cu(OAc)$_2$ (253 mg, 1.39 mmol), 2-(2-pyridyl)pyridine (218 mg, 1.39 mmol) and Na$_2$CO$_3$ (295 mg, 2.79 mmol) in DME (5.00 mL) was degassed and purged with O$_2$ for 3 times, and then the mixture was stirred at 70° C. for 12 hrs under O$_2$ atmosphere. The reaction mixture was washed with MeOH (5.00 mL×3), filtered and concentrated under reduced pressure to give a residue. The residue was purified by prep-TLC (SiO$_2$, PE/EtOAc=0/1) to give compound (121.1) (130 mg, 28.5% yield) as a yellow oil. $^1$HNMR (CDCl$_3$): δ ppm 8.56 (d, J=5.2 Hz, 2H), 7.74 (s, 1H), 7.03 (d, J=8.4 Hz, 2H), 7.73 (d, J=1.6 Hz, 1H), 7.50 (s, 1H), 7.37-7.47 (m, 1H), 7.27-7.36 (m, 1H), 6.58 (s, 1H), 3.47-3.52 (m, 1H), 2.64 (s, 3H), 1.03-1.08 (m, 2H), 0.66-0.70 (m, 2H), 0.68-0.73 (m, 2H), 0.39-0.43 (m, 2H).

Example 121: 1-cyclopropyl-5-(5-methoxypyridin-3-yl)-2-(2-methylpyridin-4-yl)-1H-indole hydrochloride According to Scheme 11, step ii: a mixture of compound (121.1) (130 mg, 397 μmol), (5-methoxypyridin-3-yl)boronic acid (60.8 mg, 397 μmol), Cs$_2$CO$_3$ (259 mg, 795 μmol), Pd(dppf)Cl$_2$·CH$_2$Cl$_2$ (32.4 mg, 39.7 μmol) in dioxane (5.00 ML) and H$_2$O (0.500 mL) was degassed and purged with N$_2$ for 3 times, and then the mixture was stirred at 120° C. for 12 hrs under N$_2$ atmosphere. The reaction mixture was washed with MeOH (2.00 mL×3), filtered and concentrated under reduced pressure to give a residue. The residue was purified by prep-TLC (SiO$_2$, PE/EtOAc=0/1). The residue was purified by prep-HPLC (HCl column: Waters Xbridge 150*25 5 u; mobile phase: [water (0.05% HCl)-ACN]; B %: 1%-20%, 12 min) to give Example 121 (54.9 mg, 35.3% yield, 100% purity) as a yellow solid: $^1$H NMR (CDCl$_3$): δ ppm=8.66 (t, J=16 Hz, 2H), 8.31 (d, J=2.4 Hz, 1H), 7.98 (s, 2H), 7.92 (d, J=14.8 Hz, 2H), 7.82 (d, J=8.4 Hz, 1H), 7.60 (d, J=5.2 Hz, 1H), 7.08 (s, 1H), 4.08 (s, 3H), 3.69 (s, 1H), 3.05 (s, 3H), 1.26 (d, J=6.4 Hz, 2H), 0.794 (s, 2H).

Example 122: 1-methyl-2,5-di(pyridin-4-yl)-1H-indole

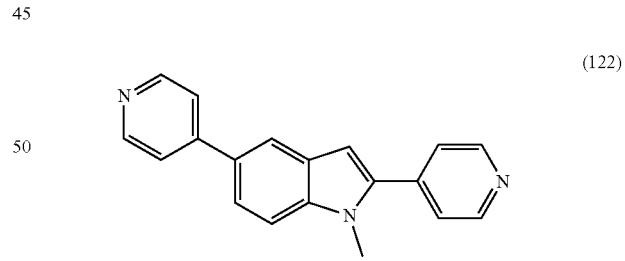

(122)

2,5-dibromo-1-methyl-1H-indole (122.1)

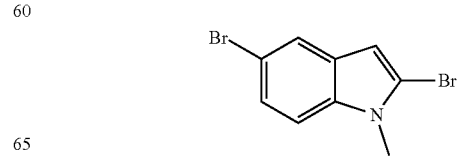

According to Scheme 12, step i: to a solution of intermediate (U9) (0.250 g, 0.7 mmol, 1 eq.) in dioxane (6 mL) was added was added 2M sodium hydroxide solution (0.7 mL, 2.12 mmol, 3 eq.) and the reaction heated to 100° C. for 150 minutes. A further portion of 2M sodium hydroxide solution (0.7 mL, 2.12 mmol, 3 eq.) was added and heating continued for a further 2 hours. The solvent was removed in vacuo, water (5 mL) was added and the pH was adjusted to 5 using 2M hydrochloric acid. The mixture was extracted with ethyl acetate (50 mL). The organic solution was dried over magnesium sulfate and the solvent removed in vacuo to afford 2,5-dibromo-1H-indole which was used directly in the next step.

According to Scheme 12, step iia: to a solution of 2,5-dibromo-1H-indole (029 g, 1.05 mmol, 1 eq.) in DMF (7 mL) was added NaH (0.063 g, 1.58 mmol, 1.5 eq) at 0° C. and the reaction stirred for 15 minutes before dropwise addition of methyl iodide (0.08 mL, 1.27 mmol, 1.2 eq.). The reaction was warmed to room temperature and stirred for 90 minutes. Ethyl acetate (75 mL) and water (15 mL) were added and the organic layer was separated and washed with water (6×15 mL) and brine (15 mL). The organic solution was dried over magnesium sulfate and the solvent removed in vacuo. The residue was purified by silica gel column chromatography using 10% ethyl acetate in iso-hexane to afford compound (122.1) (0.177 g, 58% yield). $^1$HNMR (CDCl$_3$): δ ppm 7.65 (1H, d, J=1.6 Hz), 7.28 (1H, dd, J=1.9, 8.7 Hz), 7.14 (1H, d, J=8.7 Hz), 6.52 (1H, s), 3.74 (3H, s).

Example 122:
1-methyl-2,5-di(pyridin-4-yl)-1H-indole

According to Scheme 12, step iii: To a solution of compound (122.1) (0.08 g, 0.28 mmol, 1 eq.) in DME (2 mL) was added 2M aqueous sodium carbonate (0.42 mL, 0.83 mmol, 3 eq.), pyridine-4-boronic acid (0.82 g, 0.66 mmol, 2.4 eq.) and Pd(dppf)Cl$_2$.DCM (0.011 g, 0.014 mmol, 0.05 eq.) and the reaction mixture heated to 100° C. in a microwave for 90 minutes. Ethyl acetate (20 mL) and water (5 mL) were added and the mixture filtered through celite. The organic solution was dried over magnesium sulfate and the solvent removed in vacuo. The residue was purified by preparative HPLC (conditions) to afford Example 122 (0.034 g, 43% yield): $^1$H NMR (DMSO-d$_6$): δ ppm 8.73-8.71 (2H, m), 8.62-8.60 (2H, m), 8.11 (1H, s), 7.79-7.76 (2H, m), 7.72 (2H, d, J=1.1 Hz), 7.69 (2H, dd, J=1.7, 4.5 Hz), 6.93 (1H, s), 3.89 (3H, s).

Example 123: Measurement of NOX Inhibitory Activities

The activity of the compounds according to the invention is tested in the inhibition or reduction of NOX activity in the following assays:
Fluorescence Assay Reactive oxygen species (ROS) production generated by hNOX enzymes was measured by fluorescence in both cellular and membrane-based assays using the Amplex® Red reagent. In the presence of horseradish peroxidase (HRP), the Amplex® Red reagent (10-acetyl-3,7-dihydroxyphenoxazine, AR), which is a colorless and nonfluorescent derivative of dihydroresorufin, reacts with H$_2$O$_2$ with a 1:1 stoichiometry to produce highly fluorescent resorufin at an excitation and emission wavelengths of 544 nm and 590 nm, respectively.

Materials

Membranes from CHO or HEK cells overexpressing hNox enzymes were prepared as previously described (Palicz et al., 2001, *J. Biol. Chem*, 76, 3090). After resuspension in sonication buffer (11% sucrose, 120 mM NaCl, 1 mM EGTA in PBS, pH 7.4), cells were broken by sonication and centrifuged (200 g, 10 min). The supernatant was layered onto a 17/40% (w/v) discontinuous sucrose gradient and centrifuged (150,000 g for 30 min). Membrane fractions were collected from the 17/40% interface, aliquoted in 10 μl samples and were stored at −80° C. Protein concentration was determined with Bradford reagent. Flavin Adenine Dinucleotide (FAD) (catalog #F6625-500MG), MgCl$_2$ (catalog #M8266-100G), Phosphatidic Acid (PA) (catalog #P3591-50MG) were purchased from Sigma-Aldrich. Horseradish peroxidase (HRP) (catalog #10108090001) was purchased from Roche. NADPH (catalog #A1395, 0500) was purchased from Applichem. Amplex red (AR) (catalog #A22177) was purchased from Invitrogen. 96 well polypropylene and black plates were purchased from Milian (catalog #055529 and #055218, respectively). FLUOstar OPTIMA microplate reader was supplied by BMG Labtech (Germany). Zephyr® Compact Liquid Handling Workstation was supplied by PerkinElmer (Germany).
Assay 1: ROS Production Measurement on hNOX Membranes
hNOX Membrane Assay Buffer All Solutions were placed on ice and protected from light. The final concentration in the 1× hNOX membrane fluorescent assay buffer were PBS pH7, 6 μM FAD, 15 μM PA, 1 mM MgCl$_2$, 12.5 μM AR, 0.02 u/ml, 125 ng membranes, 1.5 μg of cofactors and 30 μM NADPH. The NADPH was dissolved in water at a concentration of 12 mM and was transferred in a metal transfer plate kept at 4° C. The NADPH was added to the assay plate to initiate the reaction just before the measurement.
Compound Dilution Serial dilution (1:3, 10 serial dilution) of the compounds was performed in 100% DMSO in 96 well polypropylene plate—Row B—H Column 1-10, Row A, Column 1-10 contained reference compound. Starting concentration was $10^{-2}$ M (10 mM). Final concentration in assay was $10^{-4}$ M (100 μM). Compounds were diluted twice in PBS buffer by transferring 30 μl/well of PBS into 30 μl/well compounds sample in DMSO using Zephyr® Compact Liquid Handling Workstation. Control wells-columns 1 and 12-contained 60 μl DMSO in 50% PBS pH7.
Reaction Mixture and Assays Reaction mixture is dispensed using Zephyr® Compact Liquid Handling Workstation. 90 μl of mix with membrane were dispensed into 96 well black plates—Column 2-11, Column 1 Row A-D, Column 12 Row E-H. 90 μl of control mix were dispensed into assay plate—Column 1 Row E-H, Column 12 Row A-D, which are wells for measuring background signal. 2 μl of compounds were dispensed into each well of assay plate using Zephyr® Compact Liquid Handling Workstation. The reaction mixture with compounds was incubated in assay plates for 20 min at 37° C. in a Titramax microplate incubator with gentle agitation. 10 μl of NADPH is dispensed to the assay plate. Fluorescence reading was recorded with the FLUOstar OPTIMA microplate reader for 10 min at 37° C. (8 cycles, 1 cycle duration 55 sec).
Assay 2: ROS Production Measurement on hNOX Cells For the cell based-assay, NOX expression is induced with tetracycline and the phorbol 12-myristate 13-actetate (PMA)

was used for PMA-dependent hydrogen peroxide production in cells expressing hNOX isoforms.

Cell Buffer

Buffer to be used for cells consisted of HBSS buffer with 1% glucose. 24 hours before the assay, the compounds are incubated with tetracycline (1 mg/ml) in DMEM/F12 supplemented with 10% serum and 1% penicillin and streptomycin. The day of the assay, cells are detached with trypsin and then centrifuged at 1200 rpm for 5 min. Media is aspirated and the cells are resuspended in cell buffer. The cells are counted and resuspended to $2.5.10^6$ cells/ml. The cell pellet is kept on ice hNOX Cell Fluorescence Assay Buffer All Solutions were placed on ice and protected from light. The final concentration in the 1× hNOX cellular fluorescent assay buffer are HBSS/1% Glc pH7, 25 µM AR, 0.45 u/ml HRP, 100 nM PMA and 50'000 cells/100 µl reaction mixture. HRP is transferred in a metal transfer plate kept at 4° C. HRP is added to the assay plate to initiate the reaction just before the measurement. AR reagent is added in the mixes just before the dispensing of mixes in the black 96 microplates.

Compound Dilution

Same as described in the ROS production measurement on hNOX membranes above.

Reaction Mixture and Assays

Same as described above with the following exceptions:

- Mix with cells induced by tetracycline and stimulated or not by PMA, are in column 2-11, Column 1 Row A-D, Column 12 Row E-H which are wells for measuring full signal.
- Mix with non induced cells and stimulated or not by PMA Column 1 Row E-H, Column 12 Row A-D, which are wells for measuring background signal
- Incubation of the reaction mixture with compounds 10 min
- 10 µl of HRP are added to the entire assay plate to initiate the reaction
- Fluorescence reading is recorded during 12 cycles and obtained and used for calculations and the slope from data points read time 1 min to 12 minutes are determined and used for angiogenic modulating factors using a FITC-Lectin detection system. Mice are treated with a compound of the invention by oral gavage (10 ml/kg) from D0 to D14.

The Table 14 below summarizes the inhibition of NOX activity as measured by the above described assay 1 and expressed by their inhibitory constant calculated by non linear regression analysis using GraphPad Prism Software (GraphPad Software Co., San Diego, CA):

TABLE 14

| Example | Nox inhibitory constant Ki (µM) |
|---------|--------------------------------|
| 1 | 0.486 |
| 5 | 0.348 |
| 6 | 0.750 |
| 9 | 0.805 |
| 12 | 0.590 |
| 13 | 0.315 |
| 14 | 0.041 |
| 16 | 0.666 |
| 18 | 0.958 |
| 19 | 0.231 |
| 20 | 0.158 |
| 22 | 0.113 |
| 23 | 0.296 |
| 24 | 0.311 |

TABLE 14-continued

| Example | Nox inhibitory constant Ki (µM) |
|---------|--------------------------------|
| 26 | 0.221 |
| 27 | 0.147 |
| 29 | 0.206 |
| 32 | 0.027 |
| 33 | 0.036 |
| 34 | 0.094 |
| 39 | 0.345 |
| 49 | 0.105 |
| 52 | 0.215 |
| 53 | 0.023 |
| 54 | 0.415 |
| 57 | 0.142 |
| 59 | 0.552 |
| 62 | 0.136 |
| 64 | 0.132 |
| 65 | 0.122 |
| 68 | 0.406 |
| 69 | 0.601 |
| 81 | 0.289 |
| 83 | 0.657 |
| 89 | 0.103 |
| 90 | 0.205 |
| 92 | 0.770 |
| 93 | 0.026 |
| 101 | 0.300 |
| 109 | 0.806 |
| 111 | 0.533 |
| 112 | 0.170 |
| 113 | 0.969 |
| 119 | 0.226 |

Example 125: In Vivo NASH Model

Non alcoholic steatohepatitis (NASH) was assessed in male C57BL/6 mice (20-22 g) ordered from Elevage Janvier (France). After 7 days of acclimation, mice were then placed under High fat Diet (Western diet type diet; from Safe, France) and High Fructose Corn Syrup in drinking water (42 g/L) for a minimum of 16 weeks. Mice are treated with a compound of the invention by oral gavage (10 ml/kg) from week 8 once the NASH was already established until the end. At the end of the treatment period (at least a minimum of 8 weeks) the animals were sacrificed and liver and blood samples were collected to assess the effect of the compound on NASH and metabolic parameters. Fibrosis deposition (Sirius Red), Inflammation and Non-Alcoholic F Liver Disease (NAFLD) score were assessed by histology. Markers of liver function and metabolic markers were assessed in blood samples.

Figure 1B:
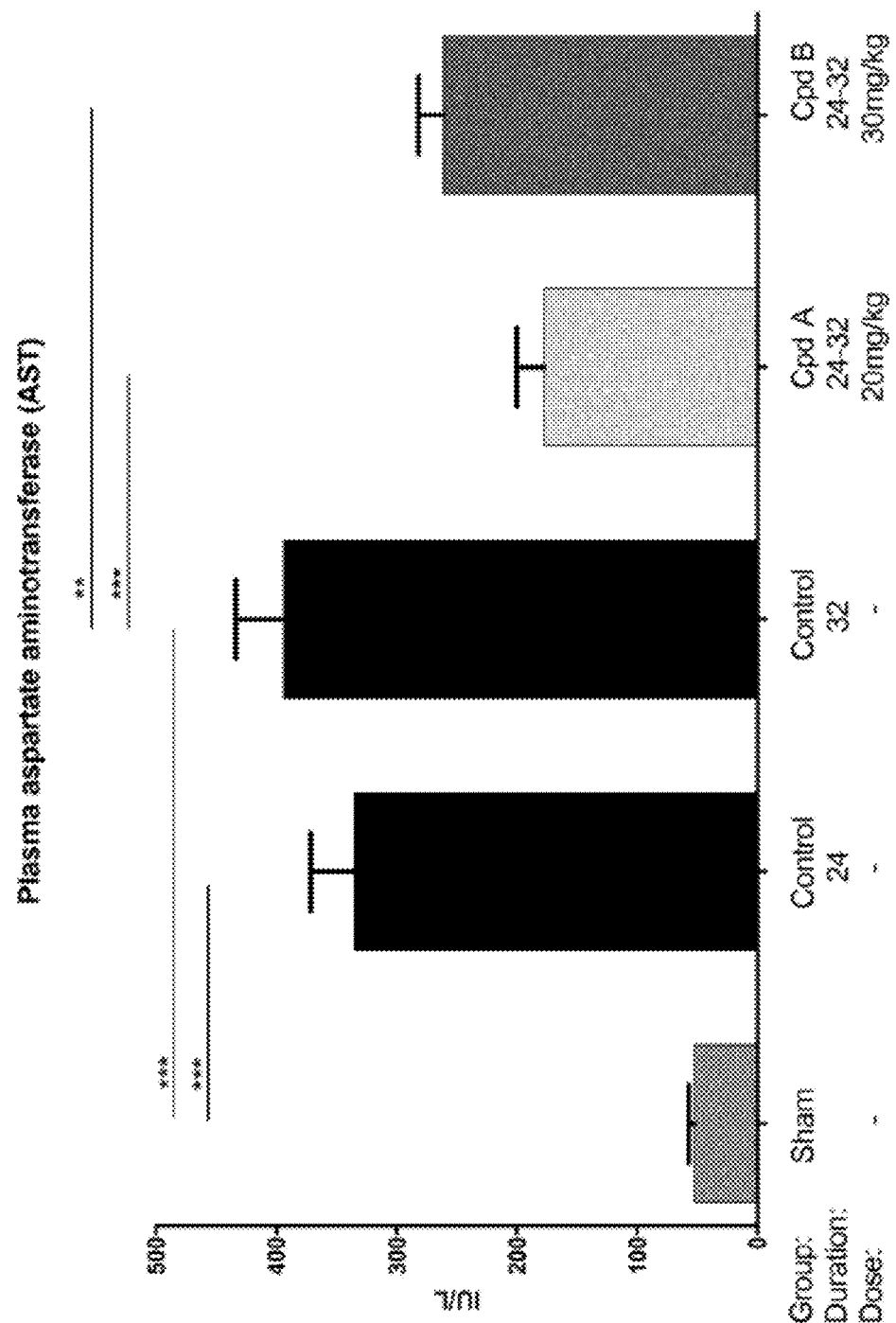

Two compounds of the invention have been tested in this model at 20 mg/kg per day. In this experiment, mice were placed under High Fat Diet and High Fructose Syrup for 32 weeks. Compounds of the invention were given from week 24 to week 32 at 20 mg/kg and 30 mg/kg respectively, and mice were then sacrificed. Presented are the NAFLD score (FIG. 1A) and the metabolic marker plasma aspartate aminotransferase (AST) (FIG. 1B). As can be seen, both compounds significantly reduced both the NAFLD score and the AST levels, showing the potential of compounds of the invention to cure NASH.

Example 126: Capsaicin Model of Inflammatory Pain in the Rat

Inflammatory pain was assessed in SD (Sprague Dawley) rats (Charles Rivers, US) in this study. Naïve mechanical hyperalgesia (eVF) paw withdrawal thresholds were determined using an electronic von Frey device (eVF, IITC Life Sciences©; Woodland Hills, CA) and animals were divided and randomized into groups with 10 per group based on baseline eVF value. On day 0, groups of the animals were received an oral dose of either vehicle or a compound of the invention in a dose volume of 5 mL/kg. Approximately one hour post dosing, 10 µg of Capsaicin was injected into the left hind paw. Mechanical hyperalgesia (eVF) paw withdrawal thresholds were then determined 30, 60, and 90 minutes after capsaicin injection. Three eVF thresholds are measured for each hind paw per time point. The mean of the 3 values is taken as the paw withdrawal threshold for that time point. The mean and standard error of the mean (SEM) are determined for each paw for each treatment group at each time point.

Figure 2:
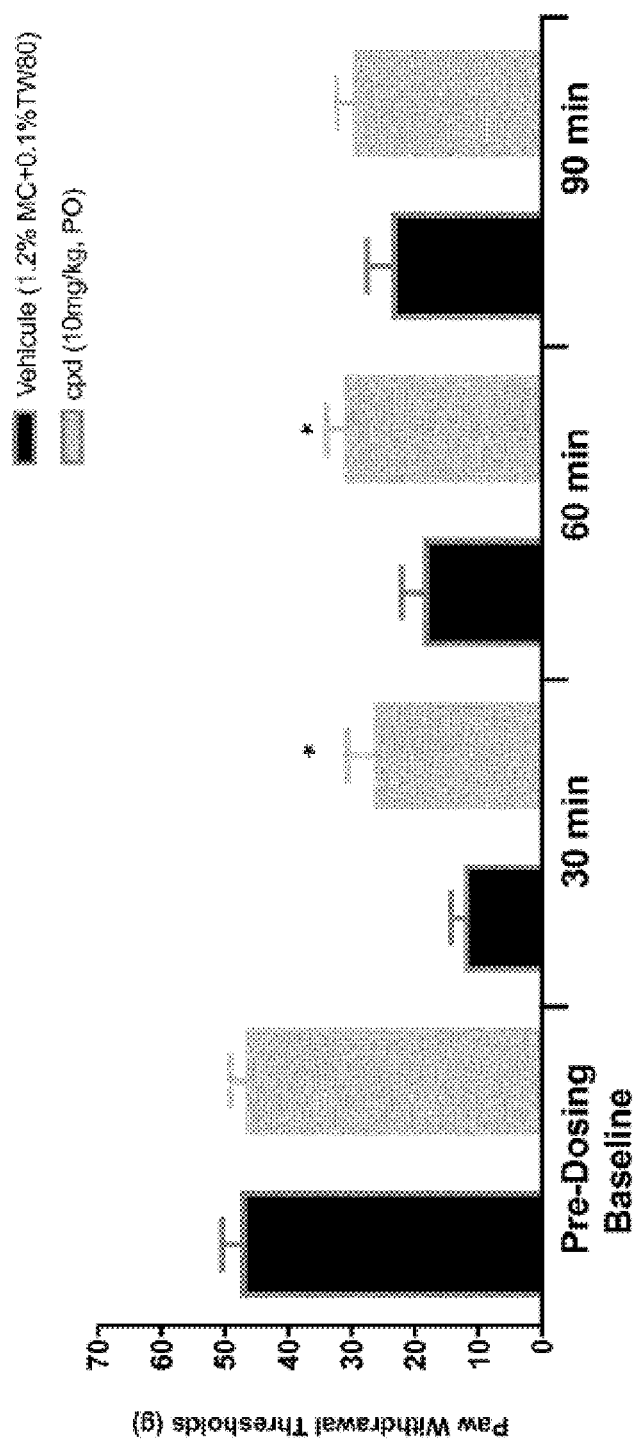
FIG. 2 shows the effect of a compound of the invention on inflammatory pain compared to vehicle in a capsaicin model in rat as measured by mechanical hyperalgesia (eVF), i.e. paw withdrawal thresholds as described in Example 126.

A compound of the invention has been tested in this model at 10 mg/kg. As can be seen on FIG. 2, a significant decrease in mechanical hyperalgesia has been observed when measured 30 min. and 60 min. after capsaicin challenge, indicating the potential use of such compound to reduce inflammatory pain.

Example 127: LPA Model of Neuropathic Pain in the Mouse

Neuropathic pain was assessed in C57BL/6 mice (Charles Rivers, US) in this study. Neuropathic pain was induced by intrathecal administration of 1 nmol lysophosphatidic acid (LPA), and mechanical allodynia was assessed using von Frey filaments (eVF, IITC Life Sciences©; Woodland Hills, CA). After 7 days, neuropathy has developed and treatment with vehicle or compound of the invention can start orally on Days 0 (7 days after LPA injection) to 7. Mechanical allodynia was then measured on days 0 and 7, mechanical allodynia was assessed prior to dosing with the test article and approximately 1,2 and 4 hours post-dosing.

Example 128: Models of Parkinson's Disease (PD)

Parkinson's disease was assessed using a mouse MPTP (1-methyl-4-phenyl-1,2,3,6-tetrahydropyridine) toxin model of PD. C57BL/6J mice were subcutaneously injected with MPTP-HCl in saline. Control mice received saline, plus 250 mg/kg intraperitoneal probenicid. Following the onset of the disease, mice were given either a compound of the invention or vehicle. Mice were treated for up to two months. After sacrifice of the mice, their brains have been processed for immunohistochemistry, histology, and biochemical analyses. Read-outs included assessment of total numbers tyrosine hydroxylase (TH)+ neurons in substantia nigra, quantification of dopamine and its metabolites.

Example 129: In Vivo Angiogenesis Assay

Angiogenesis was assessed in male C57BL/6 mice (20-22 g) ordered from Elevage Janvier (France). Angioreactors ordered from Amsbio (Directed in vivo angiogenesis Assay ref 3450-048-K) were prepared according to kit instructions. Briefly, implant grade silicone cylinders closed at one end, called angioreactors, are filled with 20 µl of Trevigen's PathClear® basement membrane extract (BME) premixed with or without angiogenic-modulating factors. A mix of VEGF (10 µg) and FGF (50 µg) ordered from Peprotech was used. Two angioreactors per mouse are then implanted subcutaneously in the dorsal flank of the mice. Accompanied with the onset of angiogenesis, vascular endothelial cells proceed to grow into the BME and form vessels in the angioreactor. As early as 15 days post-implantation, there are enough cells to determine an effective dose response to angiogenic modulating factors using a FITC-Lectin detection system. Mice are treated with a compound of the invention by oral gavage (10 ml/kg) from D0 to D14.

The invention claimed is:
1. A compound according to Formula (I):

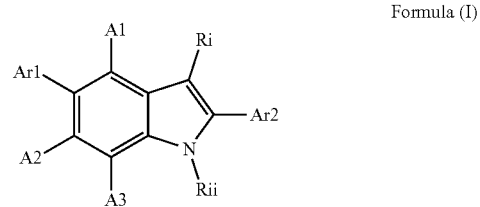

Formula (I)

wherein $A_1$ and $A_2$ groups are independently selected from hydrogen, halogen, CN, $CF_3$, $CHF_2$, an optionally substituted radical selected from $C_1$-$C_6$ alkyl, $C_3$-$C_8$ cycloalkyl, heteroalkyl, heterocycloalkyl, alkoxy, amino, carboxy, alkoxycarbonyl; $A_3$ is selected from hydrogen and halogen; $R^i$ is selected from the group of hydrogen, halogen, CN, $CF_3$, $CHF_2$, an optionally substituted radical selected from $C_1$-$C_6$ alkyl, $C_3$-$C_8$ cycloalkyl, heteroalkyl, heterocycloalkyl, carboxy; $R^{ii}$ is hydrogen or an optionally substituted $C_1$-$C_6$ alkyl, an optionally substituted $C_3$-$C_8$ cycloalkyl, an optionally substituted halo $C_1$-$C_6$ alkyl, an optionally substituted halo $C_3$-$C_8$ cycloalkyl, an optionally substituted aryl $C_1$-$C_6$ alkyl, an optionally substituted hereroaryl $C_1$-$C_6$ alkyl, an optionally substituted heteroalkyl, an optionally substituted heterocycloalkyl, an optionally substituted heterocycloalkyl $C_1$-$C_6$ alkyl, an optionally substituted hydroxy $C_1$-$C_6$ alkyl, an optionally substituted alkoxy $C_1$-$C_6$ alkyl, an optionally substituted alkoxycarbonyl $C_1$-$C_6$ alkyl, an optionally substituted aminocarbonyl $C_1$-$C_6$ alkyl, an optionally substituted aryl $C_3$-$C_8$ cycloalkyl, an optionally substituted hereroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted halo $C_3$-$C_8$ cycloalkyl; $Ar^1$ is selected from:

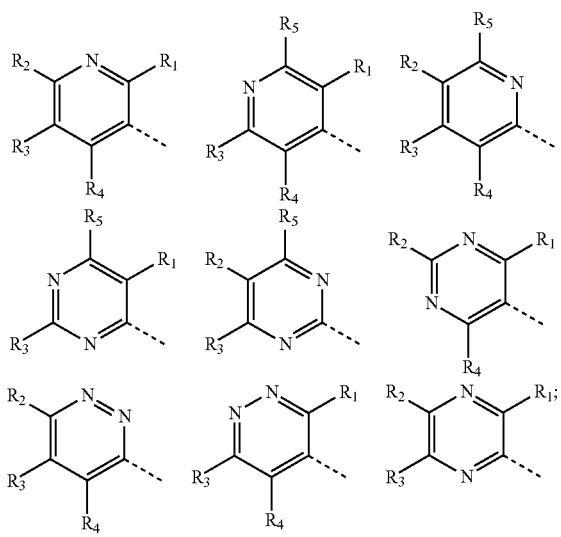

$R^1$ and $R^4$ are independently hydrogen, halogen, CN, $CF_3$, $CHF_2$, $NH_2$, an optionally substituted $C_1$-$C_6$ alkyl, an optionally substituted $C_3$-$C_8$ cycloalkyl, alkoxy, amino, an optionally substituted heterocycloalkyl, carboxy, an optionally substituted alkoxy $C_1$-$C_6$ alkyl, an optionally substituted alkoxy $C_3$-$C_8$ cycloalkyl, an optionally substituted amino $C_1$-$C_6$ alkyl, an optionally substituted amino $C_3$-$C_8$ cycloalkyl, an optionally substituted amino heterocycloalkyl $C_1$-$C_6$ alkyl, an optionally substituted carboxy $C_3$-$C_8$ cycloalkyl, an optionally substituted aminocarbonyl $C_1$-$C_6$ alkyl; $R^2$ is selected from hydrogen, halogen, $CF_3$, $CHF_2$, $NH_2$, an optionally substituted $C_1$-$C_6$ alkyl, an optionally substituted $C_3$-$C_8$ cycloalkyl, an optionally substituted alkoxy, amino, an optionally substituted heterocycloalkyl, carboxy, an optionally substituted alkoxy $C_1$-$C_6$ alkyl, an optionally substituted alkoxy $C_3$-$C_8$ cycloalkyl, an optionally substituted amino $C_1$-$C_6$ alkyl, an optionally substituted amino $C_3$-$C_8$ cycloalkyl, an optionally substituted amino heterocycloalkyl $C_1$-$C_6$ alkyl, an optionally substituted $C_3$-$C_8$ carboxy cycloalkyl, an optionally substituted aminocarbonyl $C_1$-$C_6$ alkyl; $R^3$ is selected from hydrogen, halogen, $CF_3$, $CHF_2$, $NH_2$, an optionally substituted $C_1$-$C_6$ alkyl, an optionally substituted $C_3$-$C_8$ cycloalkyl, an optionally substituted alkoxy, amino, an optionally substituted heterocycloalkyl, carboxy, an optionally substituted alkoxy $C_1$-$C_6$ alkyl, an optionally substituted alkoxy $C_3$-$C_8$ cycloalkyl, an optionally substituted amino $C_1$-$C_6$ alkyl, an optionally substituted amino $C_3$-$C_8$ cycloalkyl, an optionally substituted amino heterocycloalkyl $C_1$-$C_6$ alkyl, an optionally substituted $C_3$-$C_8$ carboxy cycloalkyl, an optionally substituted aminocarbonyl $C_1$-$C_6$ alkyl; $R^5$ is selected from hydrogen, halogen, $CF_3$, $CHF_2$, $NH_2$, an optionally substituted $C_1$-$C_6$ alkyl, an optionally substituted $C_3$-$C_8$ cycloalkyl, an optionally substituted alkoxy, amino, an optionally substituted heterocycloalkyl, carboxy, an optionally substituted alkoxy $C_1$-$C_6$ alkyl, an optionally substituted alkoxy $C_3$-$C_8$ cycloalkyl, an optionally substituted amino $C_1$-$C_6$ alkyl, an optionally substituted amino $C_3$-$C_8$ cycloalkyl, an optionally substituted amino heterocycloalkyl $C_1$-$C_6$ alkyl, an optionally substituted $C_3$-$C_8$ carboxy cycloalkyl, an optionally substituted aminocarbonyl $C_1$-$C_6$ alkyl; wherein when one from $R^1$, $R^2$, $R^3$ and $R^4$ is not H, the other from this group are H or any of $R^1$, $R^2$, $R^3$, $R^4$ and $R^5$ can be linked together to form an optionally substituted bicyclic heteroaryl; $Ar^1$ is also selected from an optionally substituted bicyclic heteroaryl, in particular from the group consisting of:

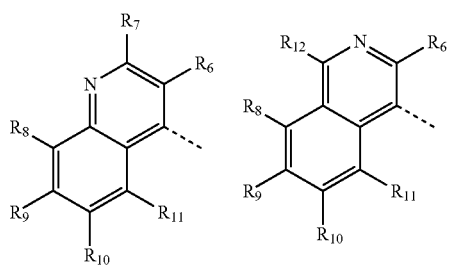

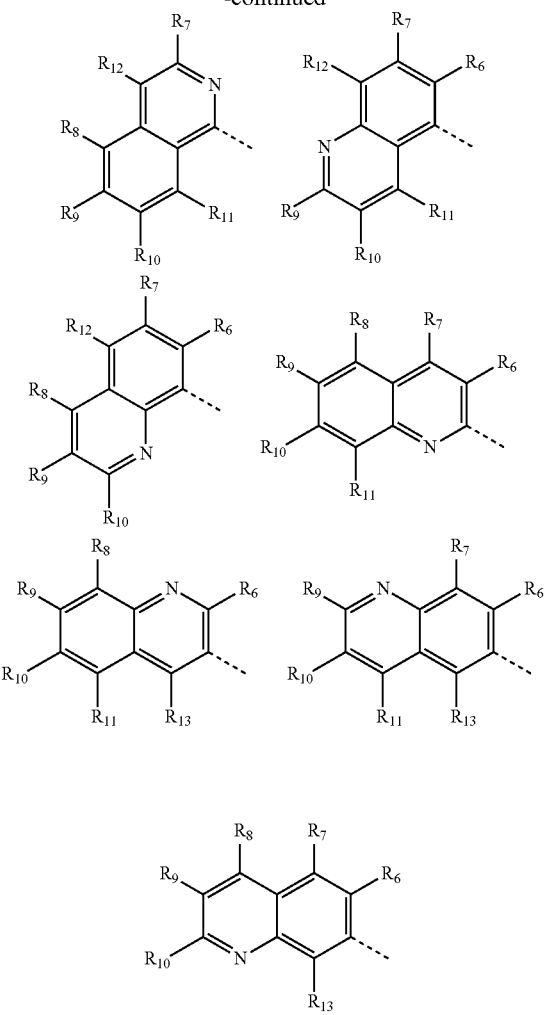

wherein $R^6$, $R^7$, $R^8$, $R^9$, $R^{10}$, $R^{11}$, $R^{12}$ and $R^{13}$ are each independently selected from hydrogen, halogen, hydroxy, CN, $CF_3$, $CHF_2$, $NH_2$, alkoxy, amino, carboxy, aminocarbonyl, alkoxy carbonyl, or an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl, acylamino, ureido, sulfonyl, sulfonylamino; $Ar^2$ is selected from the following group:

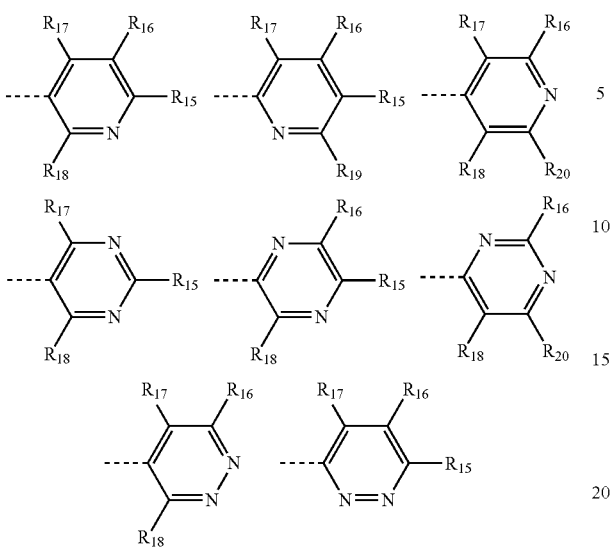

or from the following group:

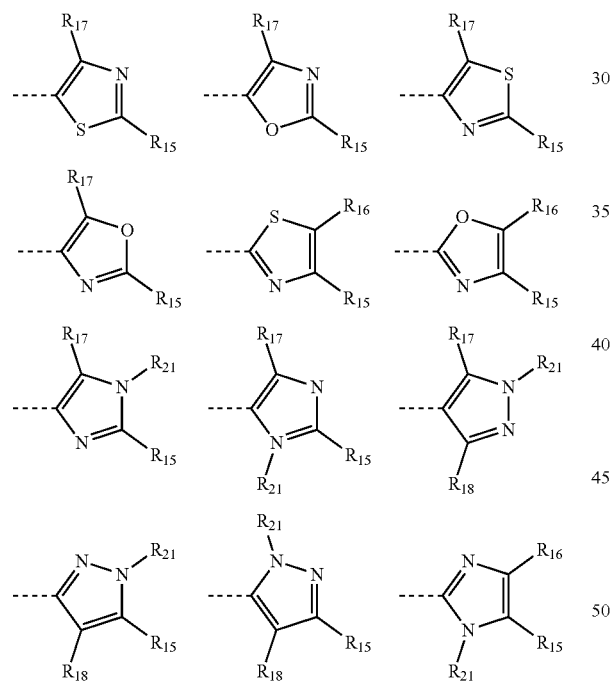

or from the following group:

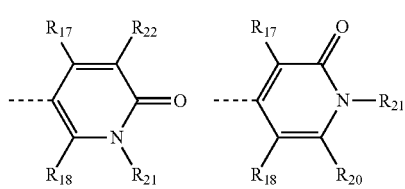

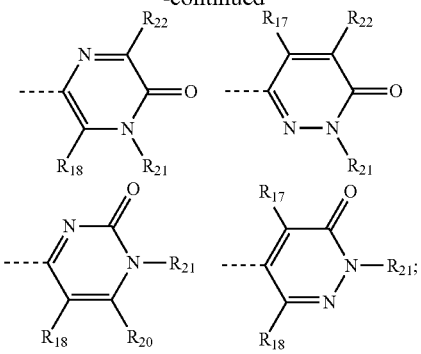

wherein $R^{15}$, $R^{16}$ and $R^{19}$ are independently selected from hydrogen, halogen, hydroxy, CN, $CF_3$, $CHF_2$, $NH_2$, alkoxy, amino, carboxy, aminocarbonyl, alkoxy carbonyl, an optionally substituted $C_1$-$C_6$ alkyl, an optionally substituted $C_3$-$C_8$ cycloalkyl, an optionally substituted alkenyl, alkynyl, an optionally substituted haloalkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl, acylamino, ureido and sulfonyl, or selected from the groups listed below:

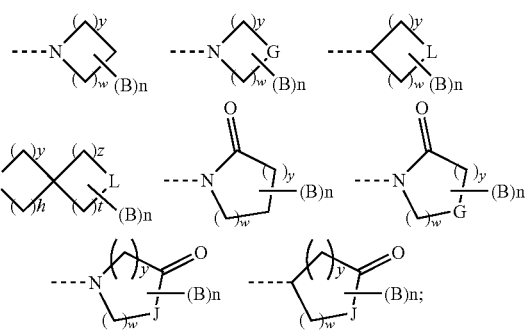

Wherein y, w, z and t are independently an integer ranging from 1 to 3; h is an integer ranging from 0 to 3; n is an integer ranging from 0 to 4; G is selected from N—$R^{23}$, O, S and $SO_2$; J is selected from C(B)n and N—$R^{23}$; L is C—(B) n, N—$R^{23}$, O, S, $SO_2$; $R^{23}$ is selected from hydrogen, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, alkoxy $C_1$-$C_6$ alkyl, an optionally substituted amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl and aminosulfonyl; B is selected from hydrogen, halogen, hydroxy, CN, $CF_3$, $CHF_2$, $NH_2$, alkoxy, amino, carboxy, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl, acylamino, ureido, sulfonyl and sulfonylamino; $R^{17}$ and $R^{18}$ are independently selected from hydrogen, halogen, CN, $CF_3$, $CHF_2$, alkoxy, amino, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted $C_3$-$C_8$ cycloalkyl $C_1$-$C_6$ alkyl, an optionally substituted heterocycloalkyl $C_1$-$C_6$ alkyl, an optionally substituted alkoxy $C_1$-$C_6$ alkyl, an optionally substituted amino $C_1$-$C_6$ alkyl, an optionally substituted heterocycloalkyl $C_3$-$C_8$ cycloalkyl, an optionally substituted alkoxy $C_3$-$C_8$ cycloalkyl, an optionally substituted amino $C_3$-$C_8$ cycloalkyl, acylamino, ureido, sulfonyl, aminosulfonyl and sulfonylamino; $R^{20}$ and $R^{22}$ are independently selected from hydrogen, halogen, CN, $CF_3$, $CHF_2$, alkoxy, amino, an optionally substituted $C_1$-$C_6$ alkyl, an optionally substituted $C_3$-$C_8$ cycloalkyl, an optionally substituted haloalkyl, an optionally substituted heteroalkyl, an optionally substituted heterocycloalkyl, an optionally substituted $C_3$-$C_8$ cycloalkyl $C_1$-$C_6$ alkyl, an optionally substituted heterocycloalkyl $C_1$-$C_6$ alkyl, an optionally substituted alkoxy $C_1$-$C_6$ alkyl, an optionally substituted amino $C_1$-$C_6$ alkyl, an optionally substituted heterocycloalkyl $C_3$-$C_8$ cycloalkyl, an optionally substituted alkoxy $C_3$-$C_8$ cycloalkyl and an optionally substituted amino $C_3$-$C_8$ cycloalkyl; $R^{21}$ is selected from hydrogen, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl and an optionally substituted aminocarbonyl $C_3$-$C_8$ cycloalkyl; $R^{15}$ and $R^{16}$ can be linked together to form an optionally substituted bicyclic heteroaryl of formula

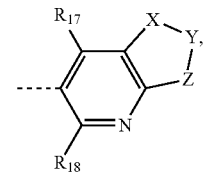

wherein X, Y and Z and each independently $C(R^{24}R^{25})$, $CH_2C(R^{24}R^{25})$, $C(=O)$, O and N—$R^{26}$; or
$R^{15}$ and $R^{16}$ can be linked together to form an optionally substituted bicyclic heteroaryl of formula

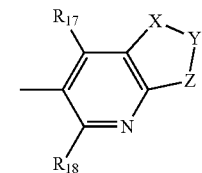

to form 3,4-dihydro-2H-pyrido [3,2-b][1,4]oxazine, wherein the nitrogen in the Z position is N—$R^{26}$; $R^{24}$ and $R^{25}$ are each independently selected from hydrogen, halogen, hydroxy, CN, $CF_3$, $CHF_2$, $NH_2$, alkoxy, amino, carboxy, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, an optionally substituted amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl, an optionally substituted aminocarbonyl $C_3$-$C_8$ cycloalkyl, acylamino, ureido, sulfonyl and sulfonylamino; $R^{24}$ and $R^{25}$ can be linked together to form an optionally substituted $C_3$-$C_8$ cycloalkyl or an optionally substituted heterocycloalkyl; $R^{26}$ is selected from hydrogen, aminocarbonyl, alkoxy carbonyl, an optionally substituted $C_1$-$C_6$ alkyl, an optionally substituted $C_3$-$C_8$ cycloalkyl, an optionally substituted halo alkyl, an optionally substituted heteroalkyl, an optionally substituted heterocycloalkyl, an optionally substituted aryl, an optionally substituted heteroaryl, an optionally substituted $C_3$-$C_8$ cycloalkyl $C_1$-$C_6$ alkyl, an optionally substituted heterocycloalkyl $C_1$-$C_6$ alkyl, an optionally substituted aryl $C_1$-$C_6$ alkyl, an optionally substituted heteroaryl $C_1$-$C_6$ alkyl, an optionally substituted alkoxy $C_1$-$C_6$ alkyl, amino $C_1$-$C_6$ alkyl, an optionally substituted carboxy $C_1$-$C_6$ alkyl, an optionally substituted aminocarbonyl $C_1$-$C_6$ alkyl, an optionally substituted heterocycloalkyl $C_3$-$C_8$ cycloalkyl, an optionally substituted aryl $C_3$-$C_8$ cycloalkyl, an optionally substituted heteroaryl $C_3$-$C_8$ cycloalkyl, an optionally substituted alkoxy $C_3$-$C_8$ cycloalkyl, an optionally substituted amino $C_3$-$C_8$ cycloalkyl, an optionally substituted carboxy $C_3$-$C_8$ cycloalkyl and an optionally substituted aminocarbonyl $C_3$-$C_8$ cycloalkyl, aminosulfonyl; $R^{15}$ and $R^{19}$ can be linked together to form an optionally substituted bicyclic heteroaryl; $R^{15}$ and $R^{21}$ can be linked together to form an optionally substituted bicyclic heteroaryl; $R^{17}$ and $R^{21}$ can be linked together to form an optionally substituted bicyclic heteroaryl; $R^{20}$ and $R^{21}$ can be linked together to form an optionally substituted bicyclic heteroaryl, wherein when $A_3$ is hydrogen at least one of $A_1$ and $A_2$ is not hydrogen, as well as a tautomer, a geometrical isomer, an optically active form, and a pharmaceutically acceptable salt thereof.

2. The compound of claim 1, wherein said compound is not 2,5-di(pyridin-4-yl)-1H-indole-3-carbonitrile or 5-(pyridin-3-yl)-2-(pyridin-4-yl)-1H-indole-3-carbonitrile or 2,5-di(pyridin-3-yl)-1H-indole-3-carbonitrile.

3. The compound according to claim 2, wherein $R^i$ is H.

4. The compound according to claim 2, wherein $R^i$ is halogen, in particular chloro.

5. The compound according to claim 2, wherein $R^{ii}$ is H.

6. The compound according to claim 2, wherein $R^{ii}$ is optionally substituted $C_1$-$C_6$ alkyl such as optionally substituted methyl, optionally substituted ethyl, optionally substituted isopropyl, $C_1$-$C_6$ alkyl optionally substituted with alkoxy such as methoxy ethyl or with optionally substituted $C_2$-$C_8$ heterocycloalkyl such as oxetan methyl or with optionally substituted $C_3$-$C_8$ cycloalkyl or with optionally substituted aryl $C_1$-$C_6$ alkyl, or with an optionally substituted amide $C_1$-$C_6$ alkyl or with optionally substituted acyl.

7. The compound according to claim 2, wherein $R^{ii}$ is optionally substituted $C_3$-$C_8$ cycloalkyl, such as an optionally substituted cyclopropyl.

8. The compound according to claim 2, wherein $A^1$ and $A^2$-groups are independently selected from hydrogen, halogen and optionally substituted $C_1$-$C_6$ alkyl.

9. The compound according to claim 2, wherein the compound is selected from the group consisting of:

1-(5-(6-chloro-5-(5-methoxypyridin-3-yl)-1H-indol-2-yl) pyridin-2-yl)-6-oxa-1-azaspiro [3.3]heptane;
1-(4-(6-chloro-5-(5-methoxypyridin-3-yl)-1H-indol-2-yl) pyridin-2-yl)-6-oxa-1-azaspiro [3.3]heptane;
1-(4-(6-chloro-5-(2-methylpyridin-4-yl)-1H-indol-2-yl) pyridin-2-yl)-6-oxa-1-azaspiro [3.3]heptane;
6-(5-(6-chloro-5-(5-methoxypyridin-3-yl)-1H-indol-2-yl) pyridin-2-yl)-2-oxa-6-azaspiro [3.3]heptane;
2-(5-(6-chloro-5-(5-methoxypyridin-3-yl)-1H-indol-2-yl) pyridin-2-yl)-7-oxa-2-azaspiro [3.5]nonane;
1-(5-(6-chloro-5-(5-methoxypyridin-3-yl)-1H-indol-2-yl) pyridin-2-yl)-3-methylazetidin-3-ol;
6-chloro-2-(6-(3,3-difluoroazetidin-1-yl) pyridin-3-yl)-5-(5-methoxypyridin-3-yl)-1H-indole
1-(5-(6-chloro-5-(5-methoxypyridin-3-yl)-1H-indol-2-yl) pyridin-2-yl) azetidine-3-carboxylic acid;
1-(5-(6-chloro-5-(5-methoxypyridin-3-yl)-1H-indol-2-yl) pyridin-2-yl) azetidine-3-carboxamide;
(1-(5-(6-chloro-5-(5-methoxypyridin-3-yl)-1H-indol-2-yl) pyridin-2-yl) azetidin-3-yl) methanol;
6-chloro-5-(5-methoxypyridin-3-yl)-2-(6-(3-methoxypyrrolidin-1-yl) pyridin-3-yl)-1H-indole;
N-(1-(5-(6-chloro-5-(5-methoxypyridin-3-yl)-1H-indol-2-yl) pyridin-2-yl) pyrrolidin-3-yl) methanesulfonamide;
(1-(5-(6-chloro-5-(5-methoxypyridin-3-yl)-1H-indol-2-yl) pyridin-2-yl) pyrrolidin-2-yl) methanol;
1-(5-(6-chloro-5-(5-methoxypyridin-3-yl)-1H-indol-2-yl) pyridin-2-yl)-5-(hydroxymethyl) pyrrolidin-2-one;
4-(5-(6-chloro-5-(5-methoxypyridin-3-yl)-1H-indol-2-yl)-3-fluoropyridin-2-yl) morpholine;
6-chloro-5-(5-methoxypyridin-3-yl)-2-(6-(4-(oxetan-3-yl) piperazin-1-yl) pyridin-3-yl)-1H-indole;
6-chloro-2-(6-(4-ethylpiperazin-1-yl) pyridin-3-yl)-5-(5-methoxypyridin-3-yl)-1H-indole;
4-(5-(6-chloro-5-(5-methoxypyridin-3-yl)-1H-indol-2-yl) pyridin-2-yl)thiomorpholine 1,1-dioxide;
6-chloro-2-(6-(4,4-difluoropiperidin-1-yl) pyridin-3-yl)-5-(5-methoxypyridin-3-yl)-1H-indole;
4-(5-(6-chloro-5-(5-methoxypyridin-3-yl)-1H-indol-2-yl) pyridin-2-yl)-1-methylpiperazin-2-one;
3'-(6-chloro-5-(5-methoxypyridin-3-yl)-1H-indol-2-yl)-1-methyl-5'H-spiro[azetidine-3,7'-furo[3,4-b]pyridine];
7-(6-chloro-5-(5-methoxypyridin-3-yl)-1H-indol-2-yl)-4-methyl-3,4-dihydro-2H-pyrido [3,2-b][1,4]oxazine;
(5-(6-chloro-5-(5-methoxypyridin-3-yl)-1H-indol-2-yl) pyridin-2-yl) (oxetan-3-yl) methanol;
6-chloro-2-(6-(methoxy (oxetan-3-yl)methyl) pyridin-3-yl)-5-(5-methoxypyridin-3-yl)-1H-indole;
2-(5-(6-chloro-5-(5-methoxypyridin-3-yl)-1H-indol-2-yl) pyridin-2-yl) propan-1-ol;
5-(6-chloro-5-(5-methoxypyridin-3-yl)-1H-indol-2-yl)-1-methylpyridin-2 (1H)-one;
4-(6-chloro-5-(5-methoxypyridin-3-yl)-1H-indol-2-yl)-1-(cyclopropylmethyl) pyridin-2 (1H)-one;
4-(5-(7-chloro-5-(5-methoxypyridin-3-yl)-1H-indol-2-yl) pyridin-2-yl) morpholine;
4-(5-(4,6-difluoro-5-(5-methoxypyridin-3-yl)-1H-indol-2-yl) pyridin-2-yl) morpholine;
4-(5-(6-chloro-5-(quinolin-5-yl)-1H-indol-2-yl) pyridin-2-yl) morpholine;
4-(5-(6-chloro-5-(5-chloropyridin-3-yl)-1H-indol-2-yl) pyridin-2-yl) morpholine;
4-fluoro-5-(5-methoxypyridin-3-yl)-2-(2-methylpyridin-4-yl)-1H-indole;
6-fluoro-5-(5-methoxypyridin-3-yl)-2-(2-methylpyridin-4-yl)-1H-indole;
4-chloro-5-(5-methoxypyridin-3-yl)-2-(2-methylpyridin-4-yl)-1H-indole;
6-chloro-5-(5-methoxypyridin-3-yl)-2-(2-methylpyridin-4-yl)-1H-indole;
5-(5-methoxypyridin-3-yl)-4-methyl-2-(2-methylpyridin-4-yl)-1H-indole;

5-(5-methoxypyridin-3-yl)-6-methyl-2-(2-methylpyridin-4-yl)-1H-indole;
4-methyl-2,5-di(pyridin-4-yl)-1H-indole;
6-methyl-2,5-di(pyridin-4-yl)-1H-indole;
4-(5-(4-chloro-5-(5-methoxypyridin-3-yl)-1H-indol-2-yl) pyridin-2-yl) morpholine;
4-(5-(6-chloro-5-(5-methoxypyridin-3-yl)-1H-indol-2-yl) pyridin-2-yl) morpholine;
4-chloro-2,5-di(pyridin-4-yl)-1H-indole
6-chloro-2,5-di(pyridin-4-yl)-1H-indole;
N,N dimethyl 4 (2 (2 methylpyridin 4 yl) 1H indol 5 yl)pyridin 2 amine;
5-(6-chloro-2-(6-morpholinopyridin-3-yl)-1H-indol-5-yl) quinolin-2-ol;
4-(5-(6-chloro-5-(thieno[2,3-c]pyridin-4-yl)-1H-indol-2-yl) pyridin-2-yl) morpholine;
4-(5-(6-chloro-5-(6-fluoroquinolin-4-yl)-1H-indol-2-yl) pyridin-2-yl) morpholine;
4-(5-(6-chloro-5-(2-methoxyquinolin-5-yl)-1H-indol-2-yl) pyridin-2-yl) morpholine;
4-(5-(6-chloro-5-(5-methoxypyridin-3-yl)-1-methyl-1H-indol-2-yl) pyridin-2-yl) morpholine;
7-(4-chloro-5-(5-methoxypyridin-3-yl)-1-methyl-1H-indol-2-yl)-4-methyl-3,4-dihydro-2H-pyrido[3,2-b][1,4]oxazine; and
7-(6-chloro-5-(5-methoxypyridin-3-yl)-1-methyl-1H-indol-2-yl)-4-methyl-3,4-dihydro-2H-pyrido[3,2-b][1,4]oxazine.

10. A pharmaceutical composition comprising a compound of claim 1 and a pharmaceutically acceptable carrier, diluent or excipient thereof.

11. A method for treating a disorder, a disease, or condition selected from a cardiovascular disorder, a respiratory disorder, a metabolic disorder, a skin disorder, a bone disorder, a neuroinflammatory and/or neurodegenerative disorder, a kidney disorder, a reproduction disorder, a disease affecting the eye and/or the lens and/or a condition affecting the inner ear, an inflammatory disorder, a liver disease, pain, a cancer, a fibrotic disorder, a psychotic disorder, an infectious disease, an allergic disorder, traumatism, septic, hemorrhagic and anaphylactic shock, a disease or a disorder of the gastrointestinal system, angiogenesis and angiogenesis-dependent and other disease and/or disorder associated with Nicotinamide adenine dinucleotide phosphate oxidase (NADPH Oxidase) in a subject in need thereof, said method comprising administering to the subject a compound of claim 1.

12. The method of claim 11, wherein the disease or condition is selected from an inflammatory disorder, a fibrotic disorder, a pain condition, or an angiogenic disorder.

13. The method of claim 12, wherein the disease or condition is an inflammatory disorder, and wherein the inflammatory disorder is selected from skin inflammation, liver inflammation, and central nervous system inflammation.

14. The method of claim 12, wherein the disease or condition is a fibrotic disorder, wherein the fibrotic disorder is selected from pulmonary fibrosis, kidney fibrosis, liver fibrosis, corneal fibrosis, skin fibrosis, and in a cancer with a fibrotic stromal component.

15. The method of claim 11, wherein the disease or condition is a cancer, wherein the cancer is selected from head and neck cancer, breast cancer, colorectal cancer, melanoma, lung cancer and glioblastoma.

16. The method of claim 11, wherein the disease or condition is a pain disorder, wherein the pain disorder is selected from neuropathic pain in particular diabetic neuropathy, spinal or nerve injury related pain, amputation, drug induced pain, multiple sclerosis, multiple myeloma, shingles, Lyme disease, Herpes Zoster infection, cancer related pain, HIV-related pain, trigeminal neuralgia and inflammatory pain.

17. The method of claim 11, wherein the disease or condition is an angiogenic disorder, wherein the angiogenic disorder is selected from a cancer with solid tumors or benign and malignant vascular tumors endometriosis and proliferative retinopathies.

18. The method of claim 11, wherein said compound is to be administered to the subject in combination with a co-agent useful in the treatment of cancer.

19. The method of claim 11, wherein said compound is to be administered to the subject in combination with an agent targeting cell-surface proteins.

20. The method of claim 11, wherein said compound is to be administered to the subject in combination with radiation therapy.

21. A compound selected from the group consisting of:
5-(2-methoxypyridin-4-yl)-2-(2-methylpyridin-4-yl)-1H-indole;
2,5-bis(2-methylpyridin-4-yl)-1H-indole;
4-(2-(2-methylpyridin-4-yl)-1H-indol-5-yl) pyridin-2-amine;
5-(5-fluoropyridin-3-yl)-2-(2-methylpyridin-4-yl)-1H-indole;
5-(5-chloropyridin-3-yl)-2-(2-methylpyridin-4-yl)-1H-indole;
5-(5-isopropoxypyridin-3-yl)-2-(2-methylpyridin-4-yl)-1H-indole;
N,N-dimethyl-5-(2-(2-methylpyridin-4-yl)-1H-indol-5-yl) pyridin-3-amine;
5-(6-methylpyridin-3-yl)-2-(2-methylpyridin-4-yl)-1H-indole;
2-(2-methylpyridin-4-yl)-5-(pyrimidin-5-yl)-1H-indole;
2-methyl-5-(2-(2-methylpyridin-4-yl)-1H-indol-5-yl)-1H-benzo[d]imidazole;
2-(2-(azetidin-1-yl) pyridin-4-yl)-5-(5-methoxypyridin-3-yl)-1H-indole;
5-(5-methoxypyridin-3-yl)-2-(2-methoxypyridin-4-yl)-1H-indole;
2-(2,6-dimethylpyridin-4-yl)-5-(5-methoxypyridin-3-yl)-1H-indole;
5-(5-methoxypyridin-3-yl)-2-(2-methylpyrimidin-4-yl)-1H-indole;
5-(5-methoxypyridin-3-yl)-2-(1-methyl-1H-imidazol-5-yl)-1H-indole;
4-(5-(5-methoxypyridin-3-yl)-1H-indol-2-yl)-2-methylthiazole;
2-(2-cyclopropylpyridin-4-yl)-5-(5-methoxypyridin-3-yl)-1H-indole;
1-(4-(5-(5-methoxypyridin-3-yl)-1H-indol-2-yl) pyridin-2-yl) azetidin-3-ol;
1-(4-(5-(5-methoxypyridin-3-yl)-1H-indol-2-yl) pyridin-2-yl)-6-oxa-1-azaspiro[3.3] heptane;
2-(2-(4,4-difluoropiperidin-1-yl) pyridin-4-yl)-5-(5-methoxypyridin-3-yl)-1H-indole;
4-(4-(5-(5-methoxypyridin-3-yl)-1H-indol-2-yl) pyridin-2-yl) morpholine;
2-(5-fluoropyridin-3-yl)-5-(5-methoxypyridin-3-yl)-1H-indole;
5-(5-methoxypyridin-3-yl)-2-(6-methoxypyridin-3-yl)-1H-indole;
4-(5-(5-(5-methoxypyridin-3-yl)-1H-indol-2-yl) pyridin-2-yl) morpholine;

5-(5-methoxypyridin-3-yl)-2-(6-(oxetan-3-yl) pyridin-3-yl)-1H-indole;
1-(5-(5-(5-methoxypyridin-3-yl)-1H-indol-2-yl) pyridin-2-yl)-6-oxa-1-azaspiro[3.3] heptane;
N,N-dimethyl-5-(5-(2-methylpyridin-4-yl)-1H-indol-2-yl) pyridin-2-amine;
4-(5-(5-methoxypyridin-3-yl)-1H-indol-2-yl)-N,N-dimethylpyridin-2-amine;
N,N-dimethyl-4-(5-(quinolin-4-yl)-1H-indol-2-yl) pyridin-2-amine;
N,N-dimethyl-4-(2-(2-methylpyridin-4-yl)-1H-indol-5-yl) pyridin-2-amine;
5-(6-cyclopropylpyridin-3-yl)-2-(2-methylpyridin-4-yl)-1H-indole;
5-(6-methoxypyridin-3-yl)-2-(2-methylpyridin-4-yl)-1H-indole;
5-(6-(methoxymethyl) pyridin-3-yl)-2-(2-methylpyridin-4-yl)-1H-indole;
5-(5-ethoxypyridin-3-yl)-2-(2-methylpyridin-4-yl)-1H-indole;
5-(5-cyclopropoxypyridin-3-yl)-2-(2-methylpyridin-4-yl)-1H-indole;
5-(5-(cyclopropylmethoxy)pyridin-3-yl)-2-(2-methylpyridin-4-yl)-1H-indole;
5-(5-cyclopropylpyridin-3-yl)-2-(2-methylpyridin-4-yl)-1H-indole;
7-(2-(2-methylpyridin-4-yl)-1H-indol-5-yl)-3,4-dihydro-2H-pyrido[3,2-b][1,4]oxazine;
3-(2-(2-methylpyridin-4-yl)-1H-indol-5-yl) quinoline;
N-methyl-4-(2-(2-methylpyridin-4-yl)-1H-indol-5-yl) pyridin-2-amine;
4-(4-(2-(2-methylpyridin-4-yl)-1H-indol-5-yl) pyridin-2-yl) morpholine;
4-(5-(6-fluoroquinolin-4-yl)-1H-indol-2-yl)-N,N-dimethylpyridin-2-amine;
4-(5-(isoquinolin-4-yl)-1H-indol-2-yl)-N,N-dimethylpyridin-2-amine;
N,N-dimethyl-4-(5-(quinolin-5-yl)-1H-indol-2-yl) pyridin-2-amine;
3-chloro-2,5-di(pyridin-4-yl)-1H-indole;
2-(2-methylpyridin-4-yl)-5-(pyridin-4-yl)-1H-indole;
5-(5-methoxypyridin-3-yl)-2-(2-methylpyridin-4-yl)-1H-indole;
5-(5-methoxypyridin-3-yl)-2-(pyridin-4-yl)-1H-indole;
5-(5-methoxypyridin-3-yl)-2-(pyridin-3-yl)-1H-indole;
4-(2-(pyridin-4-yl)-1H-indol-5-yl) quinoline;
4-(2-(pyridin-3-yl)-1H-indol-5-yl) quinoline;
2,5-di(pyridin-4-yl)-1H-indole;
2-(pyridin-3-yl)-5-(pyridin-4-yl)-1H-indole;
2,5-di(pyridin-3-yl)-1H-indole;
2-(1-methyl-1H-pyrazol-5-yl)-5-(pyridin-4-yl)-1H-indole;
5-(2-(4-methylpiperazin-1-yl) pyridin-4-yl)-2-(pyridin-4-yl)-1H-indole;
5-(5-methoxypyridin-3-yl)-2-(pyridin-2-yl)-1H-indole;
5-(5-methoxypyridin-3-yl)-2-(pyrimidin-4-yl)-1H-indole;
2-(3-fluoropyridin-4-yl)-5-(5-methoxypyridin-3-yl)-1H-indole;
1-isopropyl-5-(5-methoxypyridin-3-yl)-2-(2-methylpyridin-4-yl)-1H-indole;
1-(2-methoxyethyl)-2,5-di(pyridin-4-yl)-1H-indole;
1-(2-methoxyethyl)-5-(5-methoxypyridin-3-yl)-2-(2-methylpyridin-4-yl)-1H-indole;
1-methyl-5-(5-methoxypyridin-3-yl)-2-(2-methylpyridin-4-yl)-1H-indole;
1-ethyl-5-(5-methoxypyridin-3-yl)-2-(2-methylpyridin-4-yl)-1H-indole;
1-(cyclopropylmethyl)-5-(5-methoxypyridin-3-yl)-2-(2-methylpyridin-4-yl)-1H-indole;
1-(benzyl)-5-(5-methoxypyridin-3-yl)-2-(2-methylpyridin-4-yl)-1H-indole;
1-cyclopropyl-5-(5-methoxypyridin-3-yl)-2-(2-methylpyridin-4-yl)-1H-indole;
1-methyl-2,5-di(pyridin-4-yl)-1H-indole; and
5-(5-methoxypyridin-3-yl)-2-(3-methylpyridin-4-yl)-1H-indole;
or a pharmaceutically acceptable salt thereof.

\* \* \* \* \*